(12) United States Patent
Nakajima et al.

(10) Patent No.: US 7,632,507 B2
(45) Date of Patent: Dec. 15, 2009

(54) SYNOVIAL CELL PROTEIN

(75) Inventors: Toshihiro Nakajima, Kanagawa (JP); Tetsuya Amano, Kanagawa (JP)

(73) Assignee: St. Marianna University School of Medicine, Kanagawa (JP)

( * ) Notice: Subject to any disclaimer, the term of this patent is extended or adjusted under 35 U.S.C. 154(b) by 547 days.

(21) Appl. No.: 10/275,602

(22) PCT Filed: Dec. 21, 2001

(86) PCT No.: PCT/JP01/11289

§ 371 (c)(1), (2), (4) Date: Mar. 23, 2004

(87) PCT Pub. No.: WO02/052007

PCT Pub. Date: Jul. 4, 2002

(65) Prior Publication Data

US 2004/0152871 A1 Aug. 5, 2004

(30) Foreign Application Priority Data

Dec. 22, 2000 (JP) .............................. 2000-405082
Jun. 27, 2001 (JP) .............................. 2001-266492

(51) Int. Cl.
*A61K 39/00* (2006.01)
*A61K 38/00* (2006.01)
*A01N 37/18* (2006.01)
*C07K 1/00* (2006.01)
*C07K 14/00* (2006.01)
*C07K 17/00* (2006.01)

(52) U.S. Cl. .................. 424/185.1; 514/2; 530/350

(58) Field of Classification Search ............. None
See application file for complete search history.

(56) References Cited

U.S. PATENT DOCUMENTS

| 2007/0059294 A1 | 3/2007 | Nakajima et al. |
| 2007/0134720 A1 | 6/2007 | Nakajima et al. |

FOREIGN PATENT DOCUMENTS

| WO | WO-98/45436 | 10/1998 |
| WO | WO 98/45437 | 10/1998 |
| WO | WO-99/64576 | 12/1999 |
| WO | WO-00/55351 | 9/2000 |
| WO | WO 01/34629 | * 5/2001 |

OTHER PUBLICATIONS

Metzler et al. 'Solution structure of human CTLA-4 and delineation of a CD80/CD86 binding site conserved in CD28.' Nature Structural Biol. 4:527-531, 1997.*
Bork et al. 'Powers and Pitfalls in Sequence Analysis: The 70% Hurdle.' Genome Research. 10:398-400, 2000.*
Doerks et al. 'Protein annotation: detective work for function prediction.' Trends in Genetics. 14:248-250, 1998.*
Smith et al. The challenges of genome sequence annotation or "the devil is in the details". Nat. Biotech.15:1222-1223, 1997.*
Brenner S. 'Errors in genome annotation.' Trends in Genetics 15:132-133, 1999.*
Bowie et al. Decipering the Message in Protein Sequences: Tolerance to Amino Acid Substitutions. Science 247:1306-1310, 1990.*
Lerner et al. Nature. 299:592-596, 1982.*
Amano et al., Genes Dev, 17(19):2436-2449 (2003).
Bays et al., Nat Cell Biol, 3(1):24-29 (2001).
EMBL Accession No. AP000449 (Jul. 14, 1999).
EMBL Accession No. AC051660 (Apr. 17, 2000).
European Search Report (Supplementary Partial) mailed on May 6, 2004 for EP application No. 01272293,6 pages.
GENESEQ Accession No. AAE01355 (Jul. 18, 2001).
UNIPROT Accession No. Q20798 (Nov. 1, 1996).
Båvik et al., Proc. Natl. Acad. Sol. USA (1996) 93:3110-3114.
Ho and Mocarski, Virology (1988) 167:279-283.
Steinmayr et al., Proc. Natl. Acad. Sci. USA (1998) 95:3960-3965.
Tsuchimochi, K., "Identification of a Crucial Site for Synoviolin Expression," Mol. Cell. Biol., vol. 25, No. 16 (2005) p. 7344-7356.
Héon et al., Arch. Ophthalmol. (1996) 114(2):193-198.
Ikegawa et al., Genomics (1996) 35(3):590-592.
Lecka-Czernik et al., Molecular and Cellular Biology (1995) 15(1):120-128.
Nakazawa et al., Rinshou Meneki (2000) 33(2):261-264.
Allen et al., The Journal of Experimental Medicine (1990) 171:231-247.
Davis et al., American Journal of Pathology (2002) 160(1):357-367.
Folliard and Terlain, Agents and Actions (1988) 25(1/2)139-145.

* cited by examiner

*Primary Examiner*—Maher M Haddad
*Assistant Examiner*—Nora M Rooney
(74) *Attorney, Agent, or Firm*—Morrison & Foerster LLP

(57) ABSTRACT

The present invention discloses a novel protein called Synoviolin and a gene that encodes it. This protein is expressed specifically by synovial tissue and also accompanies the presence of an auto-antibody that recognizes this protein in rheumatoid arthritis (RA) patients. The protein according to the present invention and its antibody can be expected to be used as specific diagnostic markers for RA. In addition, the gene or protein according to the present invention may be used to permit the screening of drugs to treat RA. Moreover, the present invention provides synoviolin gene transgenic animals. The transgenic animals according to the present invention can be used as RA model animals in the development of pharmaceuticals to treat RA.

2 Claims, 46 Drawing Sheets

+GST    +GST-partial Synoviolin ( ← shows the absorbed band )

Pre-immune; Rabbit anti-serum prior to immunization of synovial cell
Post-immune; Synovial cell anti-serum A Fluorescent immunostaining on synovial cell with anti-synovial cell anti-serum Anti-synovial cell anti-serum +GST-partial Synoviolin B Fluorescent immunostaining with purified anti-synovial cell antibodies GST-column-eluted fraction GST-partial Synoviolin column-eluted fraction Anti-synovial cell anti-serum Anti-synovial cell anti-serum +GST Anti-synovial cell anti-serum +GST-partial synoviolin Purification through GST-GS column Purification through GST-partial Synoviolin-GS column Probe; [$^{35}$S]HA-Synoviolin-HAHA

Mab 10Db

Mab 7Bc

HE staining

| | | | | | | | |
|---|---|---|---|---|---|---|---|
| GST | − | − | − | + | − | − | − |
| GST-HA-Ub | − | − | + | − | + | + | + |
| ATP | − | − | + | + | − | + | + |
| E1 | − | − | + | + | + | − | + |
| E2(UbcH5c) | − | − | + | + | + | + | − |
| FLAG-Synoviolin | CE | IP | IP | IP | IP | IP | IP |

Anti-HA antibody staining

Anti-FLAG antibody staining

SYNOVIAL CELL PROTEIN

TECHNICAL FIELD

The present invention relates to a novel protein pertaining to rheumatoid arthritis (RA), a polynucleotide that encodes this protein and applications for said protein or polynucleotide. More specifically, it relates to a novel protein that can be expected to serve as a specific diagnostic marker for RA. In addition, it also relates to a novel gene that provides new approaches to the development of drugs for the treatment of RA.

BACKGROUND ART

RA is a chronic inflammatory disease of the entire body wherein hyperplasia is seen in the synovial tissue of joints. Synovial cells are fibroblastoid cells that form the one to six epithelioid layers of the synovial membranes of joints, and are thought to supply proteoglycan and hyaluronic acid to the synovial fluid. Hyperplasia of the synovial tissue is seen in the joints of RA patients along with the resulting symptoms of multilayer structures and infiltration of synovial cells into other tissue caused thereby. In addition, the blood serum of an RA patient contains autoantibodies to the Fc domain of its own IgG. Accordingly, this is thought to be an autoimmune disease, but its cause has yet to be elucidated.

The aforementioned presence of autoantibodies that recognize self-IgG has been long utilized as a characteristic diagnostic indicator of RA. Autoantibody detection kits containing modified human IgG as the main component have recently become commercially available. This autoantibody is also called the RA factor. The diagnosis of RA based on the detection of the RA factor has problems with respect to specificity to the disease and that the relationship to the cause is unclear since the system by which antibodies occur has not been elucidated.

When the pathology of RA is examined from the two aspects of that of the various immune reactions in the body and that of a hyperplastic disease of the joint synovial membrane accompanying bone disruption, much research has been performed regarding the former immune reactions and the molecular mechanism thereof is about to be clarified. However, regarding study of the latter joint synovial cells, even though this is a principal aspect of RA, even their cytobiological characteristics have to be clarified at present. Elucidating the molecular mechanism behind the onset and progress of RA and other chronic and intractable diseases is indispensable for the diagnosis, prevention and cure of the diseases. Moreover, in the current situation in which the aging of society does not show signs of halting, elucidating the pathology of the aging disease RA is an important problem from a societal standpoint also.

DISCLOSURE OF THE INVENTION

An objective of the present invention is to provide a novel protein that provides new approaches to the diagnosis and treatment of RA and a novel gene that encodes this protein. The protein provided by the present invention and the polynucleotide that encodes it are closely related to the cause of RA and will provide useful information for diagnosis, and also lead to the creation of new drugs in the development of treatment techniques. Moreover, further objective of the present invention is to provide transgenic animals wherein the genes that encode said proteins are expressed, along with knockout animals that lack said gene. These animals will be useful in analyzing the functions of the gene according to the present invention and also in the development of RA treatment methods and treatment drugs as model animals.

The present inventors used anti-human synovial cell antibodies obtained using cultured human synovial cells from RA patients as the immunogen to perform immunoscreening of a cDNA library of synovial cells of RA patients, and thus succeeded in isolating a new gene expressed in the synovial tissue of RA patients. The protein encoded by this gene was named Synoviolin after the synovial cells which are the tissues in which this gene is expressed.

The present inventors have confirmed that the reactivity of anti-human synovial cell antibodies to about 80-kDa, 140-kDa, and 220-kDa molecular weight fractions of the aforementioned cultured synovial membrane cells is absorbed by the expression products of the aforementioned synoviolin gene. In addition, the present inventors found that these bands and the expression products of the aforementioned synoviolin gene exhibit reactivity to antibodies present in the blood of RA patients. Moreover, the inventors confirmed that anti-human synovial cell antibodies exhibit strong reactivity to the synovial tissue of RA patients.

In addition, the present inventors used biochemical linkage experiments to demonstrate the presence of the Synoviolin ligand (SL), which is a natural ligand of Synoviolin. SL is a protein that the present inventors for the first time isolated as a ligand of Synoviolin. However, when an attempt was made to perform a search based on nucleotide sequences for the DNA that encodes SL, a known gene called S1-5 was found to include a common nucleotide sequence in the 5' terminal domain and 3' terminal domain. The SL isolated by the present inventors and S1-5 are nearly identical not only in the DNA partial sequence but also the size of the gene, the molecular weight of the expression product and other aspects, and thus there is a good probability that they are the same protein. S1-5 [also called "FBNL" (fibrillin-like) or "EFEMP1" (EGF-containing fibrillin-like extracellular matrix protein 1)] has been isolated as a gene that is overexpressed in a human diploid fibroblast (Lecka-Czernik, B., et al., *Molecular and Cellular Biology* (1995) 15:120-128). Structurally, it has an epidermal growth factor (EGF)-like domain that promotes DNA synthesis. The structure and nucleic acid synthesis promotion activity (hyperplastic activity) of S1-5 have been found. In addition, mutations of S1-5 have recently been reported to be associated with Malattia Leventinese (ML) and Doyne honeycomb retinal dystrophy (DHRD) (Stone, E. M., et al., *Nature Genetics* (1999) 22:199-202), but no association with RA was known. In addition, it is needless to say that the affinity with Synoviolin is completely new knowledge acquired by the present inventors.

Moreover, the present inventors have prepared a transgenic mouse by introducing the synoviolin gene and a knockout mouse that lacks the synoviolin gene and observed their phenotypes. When the Synoviolin molecule is excessively expressed in the mouse, hyperplasia of synovial membranes in joints and bone and cartilage disruption were found, thus exhibiting symptoms resembling those of rheumatoid arthritis. On the other hand, when the synoviolin gene was completely (homozygously) knocked out, incomplete limb bud and skeletal formation were found in the mouse during the fetal stage. These phenotypes suggest the contribution of Synoviolin not only to synovial tissue but also to the generation, differentiation, regeneration and metabolism of cartilage and bone tissue. In addition, in the arthropathic lesions of Synoviolin overexpression mice, metabolism and regeneration are actively induced in the synovial membrane, cartilage and bone tissue. These results clearly demonstrate that the Synoviolin molecule contributes to RA and other forms of arthropathy. Moreover, it has been confirmed that Synoviolin overexpression mice are useful as arthropathic model animals.

Based on this new knowledge, the present inventors have clarified the utility of Synoviolin and its gene, its antibodies or ligands in medical treatment or diagnosis, thereby completing the present invention. Moreover, the present inventors prepared a transgenic animal by introducing the synoviolin gene, and have demonstrated its utility as a disease model for RA. In addition, the present inventors prepared a knock-in animal by substituting the lacZ gene for the synoviolin gene. The synoviolin gene knock-out and lacZ gene knock-in animal makes it possible to analyze the effects of the lack of the synoviolin gene and also allows the activity of the synoviolin gene promoter to be easily detected by the detection of LacZ (as β-galactosidase activity) expressed by an endogenous promoter of the synoviolin gene. Using this knock-in animal, it is possible to perform screening for compounds that regulate the expression of the synoviolin gene. It is thought that it should be also possible to prevent hyperplasia of synovial membranes and to remit the disease by suppressing the overexpression of the synoviolin gene in the joints of rheumatism patients.

The gene discovered by the present inventors is closely related to the hyperplasia of synovial tissue, which is the main component of the disease of RA, and provides extremely important information for diagnosis. In addition, in contributing to the hyperplasia of synovial tissue, which is the cause of RA, the present invention's gene, its expression product, autoantibodies to the expression product, and also ligands of the expression product are thought to be material that is indispensable in the explanation of the pathology of RA. In particular, the discovery of autoantibodies that recognize Synoviolin in the blood of RA patients gives a completely new approach in the diagnosis of RA. In addition, these substances will lead to brand-new approaches in the development of RA treatment methods also.

In addition, the mutations of S1-5 identified as Synoviolin ligands are associated with ML and DHRD, and thus it is possible that Synoviolin contributes to these diseases also. Accordingly, Synoviolin may be used in the diagnosis of these diseases, while compounds that regulate the binding of Synoviolin ligands to Synoviolin or compounds that act as ligands of Synoviolin or the like become candidates as medicines for these diseases.

In addition, Synoviolin is expressed in undifferentiated mesenchymal cells during development. Accordingly, it is possible to use Synoviolin as a cell marker to isolate undifferentiated mesenchymal cells in a cell sorter or the like. The undifferentiated mesenchymal cells thus isolated can be utilized for in vitro tissue regeneration. If the in vitro reconstruction of joints is possible, then this would be useful for the reconstructive medical treatment of not only rheumatoid arthritis patients but also many patients suffering from joint damage.

To wit, the present invention relates to the following Synoviolin protein, an antibody thereof, a polynucleotide that encodes this protein, applications thereof, Synoviolin ligands and their applications, along with transgenic animals wherein the expression of the synoviolin gene is modified and applications thereof.

[1] A polynucleotide selected from the group consisting of (a) through (e) below:
 (a) a polynucleotide that encodes a protein comprising the amino acid sequence shown in SEQ ID NO: 2,
 (b) a polynucleotide comprising a protein coding domain of the nucleotide sequence shown in SEQ ID NO: 1,
 (c) a polynucleotide encoding a protein that comprises the amino acid sequence shown in SEQ ID NO: 2 in which one or more amino acids are substituted, deleted, inserted and/or added and that is functionally equivalent to the protein consisting of the amino acid sequence shown in SEQ ID NO: 2,
 (d) a polynucleotide that hybridizes under stringent conditions with a polynucleotide consisting of the nucleotide sequence shown in SEQ ID NO: 1 and that encodes a protein functionally equivalent to the protein consisting of the amino acid sequence shown in SEQ ID NO: 2, and
 (e) a polynucleotide that comprises a nucleotide sequence having at least 70% or greater identity to the nucleotide sequence shown in SEQ ID NO: 1 and that encodes a protein functionally equivalent to the protein consisting of the amino acid sequence shown in SEQ ID NO: 2.

[2] A polynucleotide that encodes a partial peptide of a protein consisting of the amino acid sequence shown in SEQ ID NO: 2.

[3] A protein or peptide encoded by the polynucleotide according to [1] or [2].

[4] The protein or peptide according to [3] that has at least one activity selected from the group consisting of the following (1) through (3):
 (1) binds to antibodies found in the blood of rheumatoid arthritis patients,
 (2) binds to the Synoviolin ligand S1-5, and
 (3) promotes synovial membrane hyperplasia.

[5] A vector into which the polynucleotide according to [1] or [2] is inserted.

[6] A transformed cell that carries the polynucleotide according to [1] or the vector according to [5].

[7] A method of manufacturing the protein or peptide according to [3], said method comprising the steps of culturing the transformed cell according to [6] and recovering the expressed protein or peptide from said transformed cell or the culture supernatant.

[8] An antibody that binds to the protein or peptide according to [3].

[9] An immunological analysis reagent for analyzing antibodies that recognize the protein or peptide according to [3], said reagent comprising the protein or peptide according to [3].

[10] The immunological analysis reagent according to [9], wherein the reagent is used to diagnose rheumatoid arthritis or to judge effectiveness of treating it.

[11] An immunological analysis reagent for analyzing the protein according to [3], said reagent comprising an antibody that reacts with the protein or peptide according to [3].

[12] The immunological analysis reagent according to [11], wherein the reagent is used to diagnose rheumatoid arthritis or to judge effectiveness of treating it.

[13] The immunological analysis reagent according to [12], wherein the protein according to [3] is present in synovial cells.

[14] A method of measuring antibodies in a biological specimen, wherein said antibodies bind to the protein according to [3] and/or a partial peptide thereof, said method comprising the following steps of:
 (1) contacting the biological specimen with the protein according to [3] and/or a partial peptide thereof, and
 (2) detecting the antibodies that bind to the protein according to [3] and/or a partial peptide thereof.

[15] A method of measuring the protein according to [3] and/or a partial peptide thereof in a biological specimen, said method comprising the following steps of:
(1) contacting the biological specimen with the antibody according to [8], and
(2) detecting the antibody according to [8], wherein said antibody binds to the protein according to [3] and/or a partial peptide thereof.

[16] A polynucleotide that comprises at least 15 nucleotides and that is complementary to a polynucleotide consisting of the nucleotide sequence shown in SEQ ID NO: 1 or to a complementary strand thereof.

[17] A method of measuring the polynucleotide according to [1] or [2] in a biological specimen, said method comprising the following steps of:
(1) contacting the biological specimen with the polynucleotide according to [16], and
(2) detecting the polynucleotide according to [16], wherein said polynucleotide hybridizes with the polynucleotide according to [1] or [2].

[18] A kit for measuring the polynucleotide according to [1] or [2], said kit comprising the polynucleotide according to [16].

[19] A method of detecting or isolating cells that express the protein according to [3], said method comprising the step of using, as an index, said protein or the expression of a gene that encodes said protein.

[20] The method according to [19], wherein said cells are rheumatoid synovial cells.

[21] The method according to [19], wherein said cells are undifferentiated mesenchymal cells.

[22] A reagent for the detection or isolation of cells that express the protein according to [3], said reagent comprising the antibody according to [8].

[23] A method of detecting rheumatoid arthritis, wherein the marker for rheumatoid arthritis is at least one selected from the group consisting of the polynucleotide according to [1], the protein according to [3], the peptide according to [3], antibodies that bind to the protein according to [3], and antibodies that bind to the peptide according to [3], the method comprising the following steps of:
i) detecting the markers for rheumatoid arthritis present in a biological specimen from a subject, and
ii) associating the results of detection of step i) with rheumatoid arthritis.

[24] The method according to [23], wherein the biological specimen is blood from a subject and the marker for rheumatoid arthritis comprises antibodies that bind to the protein according to [3] and/or antibodies that bind to the peptide according to [3].

[25] The method according to [23], wherein the biological specimen comprises synovial tissue or synovial cells from a subject and the marker for rheumatoid arthritis comprises the polynucleotide according to [1] and/or the protein according to [3].

[26] A method of detecting the binding activity of a test compound to the protein or peptide according to [3], said method comprising the following steps of:
a) contacting the test compound with the protein or peptide according to [3], and
b) observing the binding of the test compound to said protein or peptide.

[27] A method of screening compounds that have the activity of binding to the protein or peptide according to [3], said method comprising the following steps of:
a) detecting the binding activity of test compounds to the protein or peptide according to [3] by the method according to [26], and
b) selecting the test compounds the binding activity of which is higher than a control.

[28] A method of detecting the activity of blocking the binding of the protein according to [3] to its ligand, said method comprising the following steps of:
a) contacting the protein or peptide according to [3] with its ligand in the presence of a test compound, and
b) detecting the ligand and/or test compound that bind to said protein or peptide.

[29] The method according to [28], wherein the ligand is the Synoviolin ligand S1-5.

[30] A method of screening compounds that have the activity of blocking the binding of the protein according to [3] to its ligand, said method comprising the following steps of:
a) detecting the activity of test compounds to block the binding of the protein according to [3] to its ligand by the method according to [28], and
b) selecting the test compounds said blocking activity of which is higher than a control.

[31] A method of detecting the activity of a test compound to regulate signal transduction via the protein according to [3], said method comprising the following steps of:
a) contacting the test compound with said protein either in the presence of, or in the absence of, the ligand of said protein, and
b) detecting signal transduction via said protein.

[32] A method of screening compounds that have the activity of regulating signal transduction via the protein according to [3], said method comprising the following steps of:
a) detecting the activity of test compounds to regulate signal transduction via the protein by the method according to [31], and
b) selecting the test compounds said regulation activity of which is higher than a control.

[33] A method of detecting the activity of regulating the expression of the polynucleotide according to [1], said method comprising the following steps of:
a) culturing cells that express the polynucleotide according to [1] in the presence of a test compound, and
b) measuring the expression level of said polynucleotide.

[34] A method of screening compounds that regulate the expression of the polynucleotide according to [1], said method comprising the following steps of:
a) detecting the activity of test compounds to regulate the expression of the polynucleotide according to [1] by the method according to [33], and
b) selecting the test compounds that have a difference in said activity in comparison to a control.

[35] An agent that stimulates Synoviolin, said agent comprising as an active ingredient a compound that is obtainable by the screening method according to [27].

[36] An agent that blocks the binding between Synoviolin and Synoviolin ligand, said agent comprising as an active ingredient a compound that is obtainable by the screening method according to [30].

[37] An agent that blocks synovial hyperplasia, said agent comprising as an active ingredient a compound that is obtainable by the screening method according to [30] or [32].

[38] A pharmaceutical composition that comprises as an active ingredient a component selected from the group consisting of the polynucleotide according to [1] or [2], the protein or peptide according to [3], and the vector according to [5].

[39] A transgenic non-human vertebrate in which the expression of the polynucleotide according to [1] or [2] is modified or said modification is inducible.

[40] The transgenic non-human vertebrate according to [39], wherein the polynucleotide according to [1] or [2] is exogenously transformed.

[41] The transgenic non-human vertebrate according to [40], wherein said vertebrate is a rheumatoid arthritis model animal.

[42] A transgenic non-human vertebrate in which the expression of the endogenous polynucleotide according to [1] or [2] is suppressed.

[43] The transgenic non-human vertebrate according to [42], wherein another gene is knocked in.

[44] A cell derived from the transgenic non-human vertebrate according to [40] or [42].

[45] A method of detecting the activity of regulating the activity of an endogenous promoter of the polynucleotide according to [1] or [2], said method comprising the following steps of:
  a) contacting a test compound with an expression system that expresses a reporter gene under the control of the endogenous promoter of the polynucleotide according to [1] or [2], and
  b) measuring the expression level of the reporter gene.

[46] The method according to [45], wherein said expression system is the transgenic non-human vertebrate according to [43] or cells derived from the vertebrate.

[47] A method of screening compounds that regulate the activity of the endogenous promoter of the polynucleotide according to [1] or [2], said method comprising the following steps of:
  a) measuring the activity of test compounds to regulate the activity of the endogenous promoter of the polynucleotide according to [1] or [2] by the method according to [45], and
  b) selecting the test compounds that have a difference in said activity in comparison to a control.

[48] A pharmaceutical composition for regulating the expression of the polynucleotide according to [1], said pharmaceutical composition comprising as an active ingredient a compound that is obtainable by the screening method according to [34] or [47].

In addition, the present invention relates to a method of stimulating Synoviolin comprising a step of administering a compound that is obtainable by the screening method according to [27]. Alternatively, the present invention relates to a method of blocking the binding of Synoviolin to Synoviolin ligand comprising a step of administering a compound that is obtainable by the screening method according to [30]. Furthermore, the present invention relates to a method of blocking synovial hyperplasia comprising a step of administering a compound that is obtainable by the screening method according to [30] or [32]. In addition, the present invention relates to a method of promoting synovial hyperplasia comprising a step of administering a component selected from the group consisting of the polynucleotide according to [1] or [2], the protein or peptide according to [3], and the vector according to [5]. Moreover, the present invention relates to a method of regulating the expression of the polynucleotide according to [1] comprising a step of administering a compound that is obtainable by the screening method according to [34] or [47].

In addition, the present invention relates to use of a compound that is obtainable by the screening method according to [27] for the manufacture of an agent that stimulates Synoviolin. Alternatively, the present invention relates to use of a compound that is obtainable by the screening method according to [30] for the manufacture of an agent that blocks the binding between Synoviolin and Synoviolin ligand. Moreover, the present invention relates to use of a compound that is obtainable by the screening method according to [30] or [32] for the manufacture of an agent that blocks synovial hyperplasia. In addition, the present invention relates to use of a component selected from the group consisting of the polynucleotide according to [1] or [2], the protein or peptide according to [3], and the vector according to [5] for the manufacture of an agent that promotes synovial hyperplasia. Moreover, the present invention relates to use of a compound that is obtainable by the screening method according to [34] or [47] for the manufacture of a pharmaceutical composition for regulating the expression of the polynucleotide according to [1].

The present invention provides a polynucleotide that encodes Synoviolin containing a protein coding domain of the nucleotide sequence shown in SEQ ID NO: 1. The polynucleotide in the present invention may be either DNA or RNA. In addition, it may also include a modified nucleotide. The polynucleotide that encodes the Synoviolin according to the present invention can be cloned from said synovial cells from a RA patient by known methods (*Nucleic Acid Res.* (1988) 16:7583-7600). Specifically, a cDNA library is obtained based on mRNA extracted from synovial cells derived from tissue in which the onset of arthritis has occurred, where the tissue is recovered from an RA patient as synovial tissue or cultured cells (*Nucleic Acid Research* (1988) 16:7583). A probe designed based on the nucleotide sequence shown in SEQ ID NO: 1 can be used to isolate, from this library, the synoviolin gene by the screening of clones to which the probe hybridizes.

The present invention also encompasses any polynucleotide that encodes a protein that is functionally equivalent to the aforementioned Synoviolin. In the present invention, a polynucleotide that encodes a protein that is functionally equivalent to the Synoviolin is referred to as a polynucleotide functionally equivalent to Synoviolin. First, a functionally equivalent protein is defined as a protein that is immunologically equivalent to Synoviolin. To wit, in the present invention, a protein functionally equivalent to Synoviolin can be a domain of Synoviolin as long as it reacts with antibodies that specifically recognize Synoviolin and are present in the blood serum of an RA patient. Alternatively, it can also be a fragment of a protein that contains this immunologically active domain. Mutants thereof can be easily selected by a person skilled in the art by screening for fragments of Synoviolin using an RA patient blood serum panel and the blood serum of non-afflicted controls.

A protein functionally equivalent to the Synoviolin according to the present invention is defined not only based on immunological characteristics but also based on the characteristic of binding to SL (S1-5). To wit, the present invention encompasses fragments of Synoviolin that have affinity to SL (S1-5). Mutants thereof can be easily selected by a person skilled in the art by screening for candidate proteins using SL (S1-5). For example, as shown in Examples, the SL (S1-5) discovered by the present inventors demands, for the binding to Synoviolin, 120 amino acid residues corresponding to numbers 1233-1592 in the cDNA of Synoviolin. Accordingly, the protein consisting of the amino acid sequence that constitutes this domain, or the protein including this amino acid sequence constitutes a protein functionally equivalent to the Synoviolin according to the present invention. A protein that can be used as SL may be the S1-5 protein identified by accession number AAA65590 (nucleotide accession U03877), I38449, NP_061489 (nucleotide accession NM_018894), NP_004096 (nucleotide accession NM_004105), or Q12805, or a similar protein that binds to the human Synoviolin protein (SEQ ID NO: 2) (Lecka-Czernik, B. et al., Mol. Cell. Biol. 15, 120-128, 1995; Heon, E. et al., Arch. Ophthalmol. 114, 193-198, 1996; Ikegawa, S. et al., Genomics 35, 590-592, 1996; Katsanis, N. et al., Hum. Genet. 106, 66-72, 2000; Giltay, R. et al., Matrix Biol. 18, 469-480, 1999; Stone, E. M. et al., Nat. Genet. 22, 199-202, 1999).

In addition, examples of proteins functionally equivalent to human Synoviolin include proteins that have the activity of promoting synovial hyperplasia. Transgenic mice into which the human synoviolin gene was overexpressed were found to exhibit the swelling of toes that accompanies arthritis with a significant frequency. Histologically, bone disruption with synovial hyperplasia and abnormal osteogenesis were observed in their toe joints. A protein functionally equivalent to the human Synoviolin protein may also be defined based on the activity of promoting synovial hyperplasia. The promotion of synovial hyperplasia can be verified by the creation of transgenic animals, or also by the local introduction of genes into joints, or by the expression of proteins in in vitro cultured synovial cells. The method of obtaining transgenic animals using the polynucleotide according to the present invention is described later.

Examples of proteins that are functionally equivalent to human Synoviolin include proteins that have activity contributing to the formation of normal bones and the development of limbs. In development, Synoviolin was expressed strongly in the parietal bone, limbs, ears and other regions where bone and cartilage are formed, and in the limb formation stage, strong expression was observed in the apical ectodermal ridge (AER) and the anlage of cartilage and bone. Knock-out mouse embryos that have the endogenous synoviolin gene knocked out by targeting have a short length from the parietal region to the buttocks, and a trend for the formation of the skull and limbs to be premature was found. The homozygote exhibited abnormal formation in limb buds, the upper and lower jawbones and ears, leading to fetal death with a high probability. The synoviolin gene homozygous knock-out mouse exhibited abnormalities in the formation of limb buds in the fetal stage; formation of cartilage and bone was not found; and the expression of Synoviolin was found in the limb buds and regions of generation of cartilage and bone, thus demonstrating that the Synoviolin molecule contributes to skeletal formation and the development of limbs.

In an analysis using a culture system based on the explant method, the expression of LacZ in cells derived from the limb buds of a synoviolin knock-out (lacZ gene knock-in) mouse embryo was found only in undifferentiated mesenchymal cells that are thought to be the anlage of cartilage, bone and limbs. Moreover, by the alkaline phosphatase stain, von Kossa stain or other methods, it was confirmed that the capacity to form bone and cartilage was delayed in homozygous knockout mouse-derived cells. The contribution to normal bone formation and limb development is thought to be verifiable by the creation of knock-out animals, and also, by using analysis of the expression of marker genes of bone and cartilaginous cells in in vitro culture and analysis of the capacity of bone formation. In addition, the fact that a certain protein has activity contributing to normal bone formation and limb development can also be confirmed in a knock-out animal or cultured cells in which the expression of the polynucleotide according to the present invention has been suppressed, by administering a protein encoded by said polynucleotide, or by the fact that the lost functions are restored by the expression of DNA or RNA that encodes said protein.

In addition, the protein functionally equivalent to the Synoviolin according to the present invention may also be defined based on the biochemical activity of Synoviolin. The biochemical activity of Synoviolin can be defined as tyrosine kinase or ubiquitin ligase activity, for example. These biochemical activities are corroborated by various motifs discovered in Synoviolin and the results of Examples. To wit, the present invention encompasses fragments of Synoviolin that maintain at least one biochemical activity that Synoviolin has. The method of confirming the biochemical activity of Synoviolin and the domains where the respective biochemical activities are kept are specifically described later.

These proteins that are functionally equivalent to Synoviolin can be combined with other proteins to form fusion proteins. For example, a protein to which a FLAG tag, HA tag, histidine tag or other additional amino acid sequence is added but which maintains at least one of the properties of the aforementioned proteins that are functionally equivalent to Synoviolin is also included in said functionally equivalent proteins. Even in the event that the added protein has activities different from those of Synoviolin, that fusion protein is included in the functionally equivalent proteins according to the present invention, as long as it keeps at least one of the functions of Synoviolin.

Polynucleotides comprising nucleotide sequences that contain mutations in the aforementioned polynucleotide according to the present invention may also be isolated by persons skilled in the art using known methods (*Jikken Igaku Bessatsu•Idenshi Kōgaku Handobukku* [Experimental Medicine, Supplement—Genetic Engineering Handbook], (1991) pp. 246-251, Yodosha Co., Ltd.). For example, if screening is performed on a library containing similar genes using the nucleotide sequence shown in SEQ ID NO: 1 (or a fragment thereof) as a probe, then it is possible to clone DNA having a nucleotide sequence with a high degree of homology. As such a library, it is possible to use one that includes random mutations in the nucleotide sequences of SEQ ID NO: 1, a cDNA library of synovial tissue derived from non-human species, etc.

Examples of known methods of randomly adding mutations to a given nucleotide sequence include the substitution of base pairs by the nitrous acid treatment of DNA (*Proc. Natl. Acad. Sci. USA*, (1982) 79:7258-7260). With this method, it is possible to introduce the random substitution of base pairs within a specific segment by treating the segment in which mutations are to be introduced with nitrous acid. As techniques for inducing intended mutations at arbitrary locations, there are also the gapped duplex and other methods (*Methods in Enzymol.* (1987) 154:350-367). A circular double-stranded vector into which the gene to be mutated has been cloned is made into a single strand and hybridized with a synthetic oligonucleotide that has a mutation at the target location. Complementary single-stranded DNA derived from a linearized vector cut by restriction enzymes is annealed to the aforementioned circular single-stranded vector. The gap between the aforementioned synthetic nucleotide and the complementary single-stranded DNA is filled with DNA polymerase and ligation is performed to form a complete double-stranded circular vector.

The number of modified amino acids is thought to be typically 50 amino acids or less, preferably 30 amino acids or less, and even more preferably 5 amino acids or less (e.g., 1 amino acid).

When amino acids are artificially substituted, if they are substituted for amino acids with similar properties, the original activity of the protein is thought to be more easily maintained. The proteins according to the present invention include proteins to which conservative substitutions are added in the aforementioned amino acid substitution, and functionally equivalent to the human Synoviolin protein (SEQ ID NO: 2). Conservative substitutions are thought to be important in the case of substituting the amino acids in domains that are important to the activity of the protein, etc. Such conservative substitutions of amino acids are well known to persons skilled in the art.

Examples of amino acid groups for conservative substitution include basic amino acids (e.g., lysine, arginine, and histidine), acidic amino acids (e.g., aspartic acid and glutamic acid), uncharged polar amino acids (e.g., glycine, asparagine, glutamine, serine, threonine, tyrosine, and cysteine), nonpolar amino acids (e.g., alanine, valine, leucine, isoleucine, proline, phenylalanine, methionine, and tryptophan), β-branched amino acids (e.g., threonine, valine, and isoleucine), aromatic amino acids (e.g., tyrosine, phenylalanine, tryptophan, and histidine) and others.

In addition, non-conservative substitution is thought to increase the activity or the like of the protein (e.g., including constitutively active proteins and the like) or decrease same (e.g., including dominant negatives and the like).

A protein that has the amino acid sequence according to SEQ ID NO: 2 in which one or more amino acids are substituted, deleted, inserted and/or added, and that is functionally equivalent to the protein consisting of the amino acid sequence shown in SEQ ID NO: 2, also includes a natural protein. The genes of eukaryotes typically have polymorphism as seen in the interferon gene and the like. Changes in the nucleotide sequence arising due to this polymorphism may include cases where one or more amino acids are substituted, deleted, inserted and/or added. The present invention also encompasses a protein that is naturally present and that is a protein that has the amino acid sequence according to SEQ ID NO: 2 in which one or more amino acids are substituted, deleted, inserted and/or added, and that is functionally equivalent to the protein consisting of the amino acid sequence shown in SEQ ID NO: 2.

In fact, the present inventors have cloned the gene according to the present invention from a plurality of individuals and, by determining its nucleotide sequence, confirmed a clone from which one amino acid is deleted. The present invention encompasses a protein that includes such mutations in the amino sequence, and a polynucleotide comprising a nucleotide sequence that encodes it. The nucleotide sequence of the clone missing one amino acid confirmed by the present inventors is shown in SEQ ID NO: 6, and the amino acid sequence encoded by this nucleotide sequence is shown in SEQ ID NO: 7. The nucleotide sequence of SEQ ID NO: 6 lacks the gca corresponding to 1293-1295 in SEQ ID NO: 1. As a result, the amino acid sequence according to SEQ ID NO: 7 lacks the Ala in position 412 of SEQ ID NO: 2.

Alternatively, in some cases, even if there is a change in the nucleotide sequence due to polymorphism, the amino acid sequence may not change. Such mutations in the nucleotide sequence are called silent mutations. The present invention also encompasses genes comprising a nucleotide sequence that has silent mutations. Polymorphism as referred to herein means that a certain gene has different nucleotide sequences among individuals within a group. Polymorphism is unrelated to the ratios in which different genes are found.

In addition, methods by which a protein functionally equivalent to Synoviolin is obtained may include a method that utilizes hybridization, for example. To wit, this is a method wherein a polynucleotide or fragment thereof that encodes the Synoviolin according to the present invention as shown in SEQ ID NO: 1 is used as a probe and a polynucleotide that can be hybridized therewith is isolated. If hybridization is performed under stringent conditions, then a polynucleotide with high homology as the nucleotide sequence is selected, and consequently, the probability of a protein functionally equivalent to Synoviolin being contained in the protein to be isolated becomes higher. A nucleotide sequence with high homology is defined to be one that is 70% identical or greater, or preferably 90% identical or greater, for example.

Examples of the stringent conditions include conditions of, for example, hybridization at 6×SSC, 40% formamide and 25° C., and washing at 1×SSC and 55° C. While stringency is affected by the conditions such as salt concentration, formamide concentration or temperature, it is clear that a person skilled in the art may set these conditions so that the required stringency is obtained.

By using hybridization, it is possible to isolate a polynucleotide that encodes a homologue of Synoviolin in non-human animal species, for example. A homologue of Synoviolin encoded by a polynucleotide that can be obtained from a mouse, rat, rabbit, pig, goat or other non-human animal species constitutes a functionally equivalent protein in the present invention.

There are no limitations on the source of the polynucleotide of the present invention. To wit, it may be obtained from cDNA, genome DNA or synthesis. In addition, it may include a polynucleotide that has an arbitrary nucleotide sequence based on the degeneracy of genetic code, as long as it can encode the protein according to the present invention.

A protein obtained by introducing mutations into human Synoviolin (SEQ ID NO: 2) and a protein encoded by a polynucleotide isolated using the aforementioned hybridization technique and the like normally have high homology to human Synoviolin (SEQ ID NO: 2) in the amino acid sequence. High homology means that the sequence is 30% identical or greater, preferably 50% identical or greater, or more preferably 80% identical or greater (e.g., 95% or greater). The identity of nucleotide and amino acid sequences can be determined using a homology search site on the Internet [e.g., at the DNA Data Bank of Japan (DDBJ), the FASTA, BLAST, PSI-BLAST, SSEARCH or other homology searches can be used [e.g., the DNA Data Bank of Japan (DDBJ) http web site's homology search (Search and Analysis) page: www.ddbj.nig.ac.jp/E-mail/homology-j.html] and at the National Center for Biotechnology Information (NCBI), a search using BLAST can be performed (e.g., the NCBI home page http web site's BLAST page: www.ncbi.nlm.nih.gov/BLAST/; Altschul, S. F., et al., *J. Mol. Biol.* (1990) 215(3):403-410; Altschul, S. F. & Gish, W., *Meth. Enzymol.* (1996) 266:460-480; Altschul, S. F., et al., *Nucleic Acids Res.* (1997) 25:3389-3402)].

For example, calculation of the identity of the amino acid sequence can be performed in Advanced BLAST 2.1 by using blastp as the program, setting the Expect value to 10, setting all Filters to OFF, using BLOSUM62 as the Matrix, setting the Gap existence cost, Per residue gap cost and Lambda ratio to 11, 1 and 0.85, respectively, (default values) and performing a search. The value (%) of the identity can then be obtained (Karlin, S. and S. F. Altschul, *Proc. Natl. Acad. Sci. USA* (1990) 87:2264-2268; Karlin, S. and S. F. Altschul *Proc. Natl. Acad. Sci. USA* (1993) 90:5873-5877).

The present invention provides applications of these polynucleotides besides the production of proteins. To wit, the present invention encompasses anti-sense polynucleotides against polynucleotides and portions thereof that encode Synoviolin provided by the present invention. The anti-sense polynucleotide preferably has a chain length of roughly 15-20 nucleotides in order to block the transcription of genes effectively. If Synoviolin supports the abnormal hyperplasia of synovial cells, then Synoviolin anti-sense polynucleotide has a major role in the treatment of RA. From the standpoint of the control of gene expression, it is also possible to design not only anti-sense polynucleotide but a ribozyme also. To wit, it is possible to design a ribozyme that recognizes and cuts RNA transcribed from the coding region of DNA shown in SEQ ID NO: 1.

The present invention also relates to polynucleotides with a chain length of at least 15 nucleotides which are complementary to the polynucleotide according to the present invention or a complementary strand thereof. These polynucleotides are those with a chain length of preferably 20 nucleotides or more, more preferably 25 nucleotides or more, or even more preferably 30 nucleotides or more which are complementary to the polynucleotide according to the present invention or a complementary strand thereof. Herein, a "complementary strand" indicates the other strand corresponding to one strand of a double-stranded nucleic acid consisting of the base pairs A:T (or U in the case of RNA) and G:C. In addition, "complementary" is defined not to be limited to the case where there is a completely complementary sequence in a domain of at least 15 consecutive nucleotides, but also includes nucleotide sequences that have homology in the nucleotide sequence of at least 70%, preferably at least 80%, more preferably 90% and even more preferably 95% or greater. The algorithm used for determining homology may be one recited herein. These include, for example, polynucleotides that hybridize with the aforementioned polynucleotides according to the present invention and that have a chain length of at least 15 nucleotides.

Hybridization is preferably specific to the polynucleotides according to the present invention. Herein, the term "specific" means that, under stringent hybridization conditions, significant cross-hybridization does not occur with polynucleotides that encode other proteins.

These polynucleotides are useful as probes and primers that permit the detection and amplification of synoviolin genes. It is preferable that the probes and primers according to the present invention have a chain length of at least roughly 15 mer and have a nucleotide sequence that can hybridize to a sequence specific to synoviolin within the nucleotide sequence of SEQ ID NO: 1 so that specific hybridization will be possible under a given stringency. It is obvious for a person skilled in the art to design a useful nucleotide sequence for the probe or primer based on a given nucleotide sequence. Using the synoviolin gene-specific probes or primers provided based on the present invention, in situ hybridization and PCR of synovial cell sample become possible. Because Synoviolin is overexpressed in the synovial tissues of RA patients, an understanding of the state of expression in the cells is thought to give important information for understanding RA arthritic symptoms.

Synoviolin, which is the novel protein according to the present invention, can be obtained from the synovial tissue of RA patients. Because synovial cells can be cultured in vitro, it is possible to recover Synoviolin from this culture. Specifically, synovial cells are isolated from synovial tissue or the like surgically removed from RA patients in a synovectomy. By culturing the isolated cells, it is possible to recover synovial cells as adhesive cells (*J. Clin. Invest.* (1993) 92:186-193). Synoviolin is extracted and purified from the recovered cells by a combination of known protein purification techniques.

The present invention encompasses not only human Synoviolin extracted from synovial cells but also proteins that are functionally equivalent to Synoviolin. To wit, the protein according to the present invention may be produced either artificially or naturally, and encompasses a mutant protein that has the amino acid sequence of human Synoviolin (SEQ ID NO: 2) in which one or more amino acids are substituted, deleted, inserted and/or added and that is functionally equivalent to human Synoviolin. There is no limitation on the number or locations of amino acid mutations in these proteins as long as the functions of Synoviolin are preserved.

Fragments of Synoviolin can be obtained by digestion using protease. In addition, they can also be obtained by randomly cutting the DNA that encodes the Synoviolin shown in SEQ ID NO: 1, and inserting them into phage vectors to create a phage library that presents domain peptides. If this library is subjected to immunoscreening with antibodies that recognize Synoviolin, it is possible to determine the immunologically active domain. The technique for determining the immunologically active domain can also be used without modification as a technique for determining the domain of binding activity with the ligand. Regarding the cloned phages, if the nucleotide sequence of the inserted fragment is determined, then the amino acid sequence of the active domain can also be clarified.

The protein according to the present invention or a protein functionally equivalent thereto can be a protein to which various modifications are added, such as the physiological modification of sugar chains, labeling with fluorescent, radioactive or other substances, or fusion with other proteins. In particular, in the recombinants described hereinafter, there is a possibility of differences in modifications arising due to the sugar chains depending on the host in which it is expressed. Yet even if they have differences in the modification of sugar chains for example, as long as they exhibit properties similar to the Synoviolin protein disclosed in this specification, any of them are still the Synoviolin according to the present invention or functionally equivalent proteins.

Synoviolin can be obtained not only from biological materials, but also from recombinants wherein a gene that encodes it is incorporated into an appropriate expression system. Synoviolin can be obtained by genetic engineering techniques if the aforementioned polynucleotides that encode Synoviolin is incorporated into an appropriate expression system and expressed. An example of a host/vector system to which the present invention applies includes the expression vector pGEX-5X-3 and *E. coli*. pGEX-5X-3 can express a foreign gene as a fusion protein with glutathione S-transferase (GST) (*Gene* (1988) 67:31-40). Accordingly, when pGEX-5X-3 containing a gene that encodes Synoviolin is transformed into an *E. coli* strain such as BL21 under heat shock and cultured for an appropriate length of time, and then isopropylthio-β-D-galactoside (IPTG) is added, the expression of GST-fusion Synoviolin is induced. A gene that encodes Synoviolin can be obtained by amplification by PCR or the like with a cDNA library of synovial cells or the like as a template. Because the GST according to the present invention is adsorbed to Glutathione Sepharose 4B, the expression product can be easily isolated and purified by affinity chromatography.

Other examples of host/vector systems used to obtain recombinants of Synoviolin include the following. First, when a bacterium is to be as the host, expression vectors of fusion proteins using a histidine tag, HA tag, Flag tag or the like are commercially available. As for yeast, yeast of the genus Pichia is known to be effective in the expression of protein with sugar chains. From point of the addition of sugar chains, expression systems that utilize a baculovirus vector with an insect cell as the host are also useful (*Bio/Technology*, (1988) 6:47-55). Moreover, transfection of vectors using CMV, RSV or SV40 or other promoters is performed using cells of mammals, and these host/vector systems can each be used as an expression system for Synoviolin. In addition, genes can also be introduced using retrovirus vectors, adenovirus vectors, adeno-associated virus vectors or other virus vectors.

The novel protein Synoviolin provided by the present invention, and immunologically equivalent proteins are useful in the diagnosis of RA by utilizing its immunological characteristics. Antibodies that recognize Synoviolin are detected with a high frequency in the blood of RA patients, and are substantially not detected in the blood of healthy persons. Accordingly, performing an immunological analysis of the antibodies of a subject using the Synoviolin according to the present invention as an antigen gives useful information for the diagnosis of RA. To wit, if antibodies that react with Synoviolin are detected in the body fluids of a subject, then the subject may be diagnosed to have RA.

Many methods of performing the immunological analysis of antibodies are generally used. The most popular method among the various methods of performing immunological analysis of antibodies is the method reacting an antigen sensitization plate with antibodies in the sample and detecting, using an antibody-specific labeled antibody, the antibodies that are trapped on the surface of the plate and that is subjected to detection (*Immunochemistry*, (1971) 8:871-879). A method that uses an enzyme as a labeling is called the ELISA method and is in broad use. In addition, there is also a known method of mixing the sample with latex particles to which antigens are adhered and detecting antibodies as an immunological agglutination reaction (*Am. J. Med.*, (1956) 21:888-892). The immunological agglutination reaction is a method that permits rapid analysis with a single reagent, and this is a preferable method for large-scale screening.

Moreover, immunochromatography has recently become widespread as a simple analytical method. In order to apply this method to a method of immunological analysis of antibodies, a reaction system is constructed where the reaction between labeled Synoviolin and anti-Synoviolin antibodies is blocked by the antibodies in the sample. Specifically, for example, this is arranged so that the labeled Synoviolin and the sample can first contact with each other and then this can contact with the reagent component of anti-Synoviolin antibodies by a chromatographic development. If Synoviolin antibodies are present in the sample, then the labeled Synoviolin has already reacted, and accordingly, it cannot react any more with the anti-Synoviolin antibodies, which are the reagent component. By fixing the anti-Synoviolin antibodies and observing the state of the reaction of labeled Synoviolin in the region where the antibodies have been fixed, it is possible to perform an immunoassay by merely dripping samples.

In many immunoassays, it is possible to analyze antibodies according to the class of the antibodies. If necessary, information regarding a specific class of antibodies can be obtained by combining antibodies that can recognize classes of immunoglobulin such as IgG and IgM. In infectious diseases, a transition is observed where the IgM antibody measurements increase in the first stage of infection, and thereafter, the IgM antibody measurements decrease while the IgG antibody measurements increase. Such class-by-class antibody measurements may be associated with clinical symptoms of RA in the present invention also. More specifically, class-by-class measurements of antibodies may be linked to the judgment of drug efficacy or the prediction of RA onset.

In the detection of antibodies, methods are often adopted that use not only the antigen molecule itself but also chemically synthesized oligopeptides as the antigen. This is because using an analysis system that is specific to a particularly superior epitope or an epitope that has some clinical meaning is less affected by non-specific reactions. This approach is effective for Synoviolin also. Specifically, it is possible to determine the domain that functions as an epitope, based on the aforementioned method of obtaining the immunologically active domain peptide. Epitopes are known to consist of at least three amino acid residues in some cases. In addition, immunological distinction from other proteins is said to be possible with at least 8 amino acid residues. Accordingly, fragments that consist of at least 8 consecutive amino acid residues, normally 9 amino acid residues, preferably 10 amino acid residues, and more preferably 11 amino acid residues selected from the amino acid sequence of Synoviolin and that react with antibodies in a patient's blood serum are preferable as the antigen for detecting antibodies in the present invention. Moreover, methods of increasing the immunological reactivity of epitope-forming oligopeptides by adding various modifications to the oligopeptides are also known to persons skilled in the art. For example, the modification of adding an inactive protein such as human blood serum albumin or a meaningless amino acid sequence contributes to improving the immunological reactivity.

The Synoviolin, which is useful in the method of detecting RA according to the present invention, functionally equivalent proteins thereto, or partial peptides thereof can be used as immunological analysis reagents for analyzing antibodies that recognize these molecules. The immunological analysis reagents according to the present invention are useful for the diagnosis of RA and the judgment of the effectiveness of treatment.

The Synoviolin according to the present invention also makes possible the development of vaccines for the purpose of curing or preventing RA. Since Synoviolin is thought to induce the hyperplasia of synovial cells by binding to its ligand, the treatment and prevention of RA can be achieved by providing a vaccine that gives an antibody that blocks the binding of Synoviolin to its ligand. Typical methods of obtaining a Synoviolin vaccine are methods for formulating by combining mainly the domain peptide serving as the epitope of Synoviolin, with an adjuvant or a carrier protein that gives an immune stimulus due to the domain peptides of Synoviolin, which originally a human protein.

Moreover, the present invention provides antibodies that recognize Synoviolin. Antibodies against Synoviolin can be obtained by known methods by taking as the immunogen the Synoviolin according to the present invention, its immunologically equivalent proteins or fragments thereof. Polyclonal antibodies may be obtained by ordinary immune manipulation (Harlow, E. & Lane, D.; *Antibodies: A Laboratory Manual*, Cold Spring Harbor, N.Y., 1988), while monoclonal antibodies may be obtained by cloning antibody-producing cells (Kohler, G. & Milstein, C., *Nature* (1975) 256:495-497). Monoclonal antibodies are important tools for achieving high sensitivity and specificity in immunoassays.

In immunization, an immune animal is immunized with the Synoviolin according to the present invention (or an immunologically equivalent protein thereto or fragment thereof) along with an appropriate adjuvant. Synoviolin fragments that are useful as an immunogen include peptides comprising the following amino acid sequences:

```
Syno-P3    (SLALTGAVVAHAYYC/SEQ ID NO: 3),

Syno-P2    (TCRMDVLRASLPAQS/SEQ ID NO: 4),
and

Syno-P1    (GAATTTAAGTSATAC/SEQ ID NO: 5).
```

The immunogens prepared by linking these peptides to a carrier protein are specific to Synoviolin and give antibodies that have adequate binding affinity. Keyhole lympet hemocyanin (KLH), bovine serum albumin (BSA) or the like can be used as the carrier protein used to obtain the immunogen. The immune animals typically used include a rabbit, mouse, rat, goat or sheep. The adjuvants typically used include Freund's complete adjuvant (FCA) and the like (*Adv. Tubercl. Res.*, (1956) 1:130-148). By adding immunity at appropriate intervals and drawing blood upon confirming the increase in the antibody titer, it is possible to obtain antiserum. Moreover, by purifying its antibody fractions, it is possible to obtain purified antibodies.

Alternatively, monoclonal antibodies can be obtained by collecting antibody-producing cells and cloning them by cell fusion or other methods. These antibody-producing cells include those derived from immune animals and also antibody-producing cells collected from RA patients that produce auto-antibodies against Synoviolin. Moreover, it is possible to construct chimeric antibodies or humanized antibodies based on the antibody genes of monoclonal antibody-producing cells derived from immune animals thus obtained. When antibodies are administered to humans, animal antibodies are not preferable because they will be eliminated as foreign matter. For this reason, chimeric antibodies wherein human antibodies are substituted for the constant regions of strongly antigenic antibodies, or humanized antibodies wherein human genes are substituted for not only the constant regions but also the framework of the variable regions are required. At this point, by using the variable regions of antibodies derived from antibody-producing cells of RA patients, it is possible to reconstruct human-type antibodies, and accordingly, it is possible to construct highly safe antibodies more easily.

The chimeric antibodies or humanized antibodies that recognize Synoviolin provided based on the present invention are useful in a drug delivery system (DDS) that targets the synovial cells of RA patients. In a DDS that uses antibodies that recognize Synoviolin according to the present invention, Fas ligands or anti-SL antibodies or the like can be shown to be substances expected to be useful by linking to antibodies.

Alternatively, the antibodies of the present invention are useful in the detection of Synoviolin. Synoviolin is overexpressed in the synovial tissue of RA patients. Accordingly, the detection of Synoviolin in synovial cells, synovial tissue or body fluids gives important information for the diagnosis of RA. Specifically, when Synoviolin is detected in synovial tissue or blood, RA is thought to be advanced. The antibodies of the present invention can be used as reagents for the immunological detection of Synoviolin. Methods of using antibodies to immunologically detect the proteins present in tissue or blood are known. Reagents for the immunological analysis that contain the antibodies according to the present invention are useful in the diagnosis of RA and the determination of the effectiveness of treatment.

In addition, the antibodies according to the present invention can be used for the separation or detection of cells that express Synoviolin. The Synoviolin protein according to the present invention is observed in AER in development, and is also expressed strongly in undifferentiated mesenchymal cells that become the anlage of synovial membrane, cartilage, bone and limbs. Accordingly, Synoviolin can be used as a marker of AER and undifferentiated mesenchymal cells. To wit, it is possible to detect and separate AER and undifferentiated mesenchymal cells using the expression of Synoviolin as an index. The antibodies are appropriately labeled by fluorescence or the like. For example, antibodies against Synoviolin can be used in cell sorting or the like to separate cells that express Synoviolin. The separated undifferentiated mesenchymal cells are useful in the in vitro formation of bone and cartilage, or the reconstruction of joints.

The stroma of bone, cartilage, muscle, tendons, fat, bone marrow and the like are formed from undifferentiated mesenchymal cells in vitro or in vivo (Kuznetsov, S. A., et al., *J. Bone Miner. Res*. (1997) 12:1335-1347; Prockop, D. J., *Science* (1997) 276:71-74; Thompson, C. M. and Young, R. A., *Proc. Natl. Acad. Sci. USA* (1995) 92:4587-4590; Caplan, A. I., *J. Orthop. Res*. (1991) 9:641-650; Friedenstein, A. J., *Int. Rev. Cytol*. (1976) 47:327-359; Owen, M. and Friedenstein, A. J., in "Cell and Molecular Biology of Vertebrate Hard Tissues," D. Evered and S. Harnett, Eds., Wiley, Chichester, UK, (1988) pp. 42-60; Friedenstein, A. J., et al., *Cell Tissue Kinet*. (1987) 20:263-272; Ashton, B. A., et al., Clin. Orthop. Relat. Res. (1980) 151:294-307; Bab, I, et al., *Clin. Orthop. Relat. Res*. (1984) 187:243-254; Haynesworth, S. E., et al., *Bone* (1992) 13:81-88; Caplan, A. I., *Clin. Plast. Surg*. (1994) 21:429-435; also see, for example, the http web site of Genzyme, www.genzymebiosurgery.com/).

For example, it is possible to differentiate undifferentiated mesenchymal cells in vitro and form cells of adipocytic lineage, chondrocytic lineage and osteocytic lineage (Pittenger, M. F., et al, *Science* (1999) 284:143-147).

Differentiation to adipocytes can be induced by, for example, treatment with 1-methyl-3-isobutylxanthine, dexamethasone, insulin and indomethacin (Pittenger, M. F., U.S. Pat. No. 5,827,740, 1998). Differentiation to chondrocytes can be performed by, for example, using centrifugation or the like to make the cells into minute clumps and then stimulating with transforming growth factor (TGF)-β3 in a culture medium that contains no blood serum (Mackay, A. M., et al., *Tissue Eng*. (1998) 4:415-428; Yoo, J. U., et al., *J. Bone Joint Surg. Am*. (1998) 80A: 1745-1757). Differentiation to osteocytes can be induced by dexamethasone, β-glycerophosphate and ascorbic acid in the presence of 10% fetal calf serum, for example (Kuznetsov, S. A., et al., *J. Bone Miner. Res*. (1997) 12:1335-1347; Prockop, D. J., *Science* (1997) 276:71-74; Thompson, C. M. and Young, R. A., *Proc. Natl. Acad. Sci. USA* (1995) 92:4587-4590; Caplan, A. I., *J. Orthop. Res*. (1991) 9:641-650; Friedenstein, A. J., *Int. Rev. Cytol*. (1976) 47:327-359; Owen, M. and Friedenstein, A. J., in "Cell and Molecular Biology of Vertebrate Hard Tissues," D. Evered and S. Harnett, Eds., Wiley, Chichester, UK, (1988) pp. 42-60; Bruder, S. P., et al., *J. Cell. Biochem*. (1997) 64:278-294; Jaiswal, N., et al., *J. Cell. Biochem*. (1997) 64:295-312; Bruder, S. P., et al., *J. Bone Miner. Res*. (1998) 13:655-663).

In addition, regarding the in vivo case also, for example, undifferentiated mesenchymal cells can be transplanted in utero and differentiated into cartilaginous cells, fat cells, muscle cells, cardiac muscle cells, bone marrow stromal cells and thymus stromal cells (Liechty, K. W., et al., *Nature Medicine* (2000) 6:1282-1286). By these methods, it is possible to reconstruct tissue in vitro or in vivo from the separated undifferentiated mesenchymal cells. The reconstructed tissue or organs is expected to have application in regenerative medicine.

In addition, because Synoviolin is overexpressed in rheumatoid synovial cells, it can be used as a cell marker for rheumatoid synovial cells. If the antibodies according to the present invention are used as reagents for the separation or detection of cells, then the antibodies can be combined with other solvents or solutes to form a composition. For example, it can be combined with distilled water, pH buffers, salts, proteins, surfactants and the like.

Synoviolin is overexpressed in the synovial tissue of RA patients. In addition, antibodies that recognize Synoviolin (auto-antibodies) are detected with a high frequency in the blood of RA patients. On the other hand, Synoviolin antibodies are substantially undetectable in the blood of healthy persons. Moreover, Synoviolin suppresses the growth of cultured synovial cells in vitro. This is thought to be because Synoviolin competes with ligands that promote synovial cell growth. Based on this information, the following mechanism can be expected. To wit, the overexpression of Synoviolin in synovial cells promotes the binding of Synoviolin, which has a growth-promoting action on synovial cells, to ligands, and as a result, growth of synovial cells is promoted. Moreover, the hyperplasia of these synovial cells itself is nothing other than the pathology of RA.

Based on the aforementioned knowledge, the present invention provides a method of detecting or method of diagnosing rheumatoid arthritis comprising the following steps of:

i) detecting markers for rheumatoid arthritis present in a biological specimen from a subject, and ii) associating the results of detection of step i) with rheumatoid arthritis.

The markers used in the method of detecting or method of diagnosing rheumatoid arthritis according to the present invention may be any of the following markers. The method of measuring these markers is as described previously.

Synoviolin or a polynucleotide functionally equivalent to Synoviolin,

Synoviolin or a protein functionally equivalent to Synoviolin,

Synoviolin or a peptide functionally equivalent to Synoviolin,

Antibodies that bind to Synoviolin or a protein functionally equivalent to Synoviolin, and Antibodies that bind to Synoviolin or a peptide functionally equivalent to Synoviolin.

For example, if antibodies that react with Synoviolin or a protein or peptide functionally equivalent to Synoviolin are detected in a blood sample taken from a patient, then the probability that the patient has RA is high. Alternatively, the expression of Synoviolin or a protein functionally equivalent to Synoviolin in synovial tissue taken from a patient indicates the hyperplasia of synovial tissue due to RA. The expression of a protein can be detected using the presence of the protein or mRNA as an index.

In addition, the Synoviolin according to the present invention and the gene therefor provide new approaches to the development of drugs for the treatment of RA, based on the above mechanism and such. First of all, with the Synoviolin according to the present invention, ligands of Synoviolin can be detected using the binding activity to Synoviolin as an index. To wit, the present invention relates to a method of detecting the binding activity to Synoviolin comprising the following steps of:

a) contacting a test compound with Synoviolin or a protein or peptide functionally equivalent to Synoviolin, and b) observing the binding of the test compound to said protein or peptide.

Moreover, it is possible to perform the screening of ligands for Synoviolin based upon the aforementioned detection method. The screening method according to the present invention specifically comprises the following steps of:

a) detecting the binding activity of test compounds to Synoviolin or a protein functionally equivalent to Synoviolin by the aforementioned method of detecting the binding activity to Synoviolin, and b) selecting the test compounds the binding activity of which is higher than a control.

Candidate compounds for ligands include not only natural substances and variants thereof but also low-molecular weight organic compounds. Binding between the aforementioned proteins and candidate compounds can be detected directly by labeling the candidate compounds. Alternatively, this can be confirmed using the blocking of binding with a known SL as an index. To wit, the candidate compound is contacted with the protein according to the present invention in the presence of molecules that clearly exhibit the binding activity to proteins according to the present invention, such as S1-5. Alternatively, after the candidate compound is contacted with the protein according to the present invention, it is possible, by further contacting with SL, to evaluate the binding activity of the candidate compound. In the case where the blocking of binding is used as an index, only SL, which is already known, has to be labeled. Accordingly, this enables a simple screening method.

As a control, it is preferable that the same manipulation as in step a) be performed in the absence of the test compound. Alternatively, this may be a control where the test compound is present at a concentration lower than that of step a). In addition, it is also possible to perform the same manipulation in step a) using a molecule that is known to bind to Synoviolin in place of the test compound, and thus select compounds that have a binding activity higher than that of that molecule.

In addition, screening methods for ligands based on the genes shown in Examples are also possible. For example, a commercial two-hybrid system may be used to screen a library containing genes that encode candidate ligands for genes that encode proteins that bind to Synoviolin. This method is an effective method of screening for natural ligands. Alternatively, it is possible to clone ligands by expression screening using a phage library into which cDNAs are incorporated and labeled Synoviolin. The present inventors used this screening method to discover the natural ligand of Synoviolin called SL. SL may possibly bind to Synoviolin on the surface of synovial cells and stimulate hyperplasia. Accordingly, the measurement of the level of SL in the blood may possibly be associated with the pathology of RA. SL can be measured based on the binding activity to Synoviolin. Naturally, an immunoassay can be performed with anti-SL antibodies, and SL can also be measured by a sandwich method that combines the two.

The present inventors confirmed that when Synoviolin is added to cultured synovial cells, it acts to suppress hyperplasia. This is explained in terms of the neutralization of SL in the culture medium as follows: the blocking of the binding of Synoviolin to its ligand conceivably leads to the suppression of hyperplasia of synovial cells, thereby conferring the effect of treating RA. Ligands that can be obtained by the screening method of the present invention competitively block the binding of Synoviolin to its natural ligand, and accordingly, they can be expected to have the activity of effectively suppressing the hyperplasia of RA synovial cells (as an antagonist).

In addition, the Synoviolin ligands that can be obtained by the screening method of the present invention can be expected to have the activity of stimulating the activity of Synoviolin (as an agonist) in the same manner as the aforementioned SL. Ligands that stimulate Synoviolin are useful as an agent that stimulates Synoviolin or an agent that promotes bone formation. More specifically, ligands that stimulate Synoviolin can be used as drugs to treat osteoporosis, bone disruption, sports injuries or the like.

These methods of detecting binding activity and screening methods can be expanded so that the present invention further provides a method of detecting the activity of blocking the binding of Synoviolin or a functionally equivalent protein to the Synoviolin ligand, and a method of screening compounds. The method of detecting the activity of blocking the binding of Synoviolin to the Synoviolin ligand based on the present invention comprises the following steps of:

a) contacting the Synoviolin or a protein or peptide functionally equivalent to Synoviolin with its ligand in the presence of a test compound, and b) detecting the ligand and/or test compound that binds to said protein or peptide.

Moreover, based on the above-mentioned detection method, the present invention provides a method of screening for compounds that block the binding of Synoviolin or a protein functionally equivalent thereto to the Synoviolin ligand. To wit the present invention relates to the following screening method comprising the steps of:

a) detecting the activity of test compounds to block the binding of Synoviolin or a protein functionally equivalent thereto to its ligand by the aforementioned detection method, and b) selecting the test compounds said blocking activity of which is higher than a control.

As a control, it is preferable that the same manipulation as in step a) be performed in the absence of the test compound. Alternatively, this may be a control where the test compound is present at a concentration lower than that of step a). In addition, for example, it is also possible to perform the same manipulation in step a) using a molecule that is known to block the binding between Synoviolin and its ligand in place of the test compound, and thus select compounds that have a binding activity higher than that of that molecule.

By this screening, it is possible to obtain compounds that act as an antagonist to Synoviolin or functionally equivalent proteins thereto. Examples of ligands of Synoviolin include the SL (S1-5) recited in Examples. Specifically, the S1-5 proteins identified by accession number AAA65590, 138449, NP_061489, NP_004096 or Q12805, or similar proteins can be used as long as they have the activity of binding to the Synoviolin protein (Lecka-Czernik, B., et al., *Mol. Cell. Biol.* (1995) 15:120-128; Heon, E., et al., *Arch. Ophthalmol.* (1996) 114:193-198; Ikegawa, S., et al., *Genomics* (1996) 35:590-592; Katsanis, N., et al., *Hum. Genet.* (2000) 106:66-72; Giltay, R., et al., *Matrix Biol.* (1999) 18:469-480; Stone, E. M., et al., *Nat. Genet.* (1999) 22:199-202). The contact between Synoviolin and Synoviolin ligand can be made before, after or at the same time that the candidate compound is applied.

The compounds to be screened here are those that are thought to bind to Synoviolin and block the binding of Synoviolin to the ligand, and those that block the ligand. Compounds that bind to Synoviolin can be screened by labeling the ligand and by making it compete with the candidate compound. If a compound that binds to the ligand is a candidate, then the opposite is performed. In each screening, it is preferable that radioactive isotopes are used for labeling, because their effect on activity is small. An antagonist of Synoviolin thus obtained is presumed to have the action of suppressing the hyperplasia of synovial cells, and can be expected to have the effect of treating RA.

In addition, the Synoviolin ligand S1-5 is suggested to be a causal gene for Malattia Leventinese (ML) and Doyne honeycomb retinal dystrophy (DHRD) (Stone, E. M., et al., *Nature Genetics* (1999) 22:199-202). These diseases have symptoms similar to age-related macular degeneration (AMD) wherein deposits known as drusen occur. Because of these, there is a possibility that Synoviolin contributes to ML and DHRD. Diagnosing ML and DHRD can be performed by investigating the mutations and polymorphism of synoviolin. In addition, compounds that act as ligands of Synoviolin obtainable by the screening according to the present invention, compounds that block the interaction between Synoviolin and S1-5 and the like are expected to have use as drugs that contribute to the prevention or treatment of these diseases.

In addition, it is possible to use the Synoviolin according to the present invention to evaluate the activity of a compound to regulate signal transduction via Synoviolin, or to screen for compounds that regulate signal transduction via Synoviolin. Specifically, the present invention provides a method of detecting the activity of a test compound to regulate signal transduction via Synoviolin, comprising the following steps of:

a) contacting the test compound with Synoviolin either in the presence of, or in the absence of, the Synoviolin ligand, and b) detecting signal transduction via Synoviolin.

In addition, the present invention relates to a method of screening for compounds that have the activity of regulating signal transduction via Synoviolin, comprising the following steps of:

a) detecting the activity of test compounds to regulate signal transduction via Synoviolin by the aforementioned method, and b) selecting the test compounds said regulation activity of which is higher than a control.

As a control, it is preferable that the same manipulation as in step a) be performed in the absence of the test compound. Alternatively, this may be a control where the test compound is present at a concentration lower than that of step a). In addition, for example, it is also possible to perform the same manipulation in step a) using a molecule that is known to have the activity of promoting or blocking the signal transduction via Synoviolin in place of the test compound, and thus select compounds that have a regulating activity higher than that of that molecule.

In the present invention, signal transduction via Synoviolin is defined to be that the stimulus applied to Synoviolin is transduced to different molecules. There is no limitation on the type of stimulus. Many modes of signal transduction are known to be present in the body. A representative example of signal transduction is the regulation of activity by the modification of proteins. For example, the activity of certain types of proteins is regulated by phosphorylation or acetylation. In addition, the activity of a protein is known to be controlled by its cleavage. In order for a protein to be cleaved in a more specific manner, the presence of ubiquitin or other molecules is important. Signal transduction can be detected by using as an index the change in the activity or structure of molecules that constitute signal transduction where the change is generated by the transduction of signals. Alternatively, signal transduction can be detected using as an index the formation of complexes for signal transduction.

Examples of signal transduction especially include phosphorylation or dephosphorylation signals. Many of cell proliferation signals are known to be transduced to downstream signal molecules via protein modification based on protein phosphorylation or dephosphorylation. Since the Synoviolin according to the present invention also has a cell proliferation action, this suggests that signal transduction via Synoviolin is also transduced by phosphorylation of protein. In fact, the present inventors discovered the phosphorylation action of Synoviolin expression. Accordingly, it is possible to measure signal transduction via Synoviolin by detecting the phosphorylation of protein.

Receptors involved in cell proliferation or differentiation have the following domains as enzyme active sites (*Jikken Igaku Bessatsu•Bioscience Yōgo Raiburari, Kaiteiban Saitokain Zōshoku Inshi* [Experimental Medicine, Supplement— Bioscience Terminology Library, Revised Version: Cytokines/Growth Factors], Yodosha Co., Ltd., 1998):

the tyrosine kinase domain (VEGF receptor, PDGF receptor, HGF receptor, EGF receptor, etc.), the tyrosine phosphatase domain (RPTP, etc.), and the serine/threonine kinase domain (TGFβ receptor, etc.).

Synoviolin is predicted to keep these enzyme activities either directly or indirectly. The phrase "having an enzyme activity indirectly" refers that there is no enzyme activity site in the Synoviolin molecule, but a molecule that is associated with Synoviolin has an enzyme activity. Known examples of such molecules include the TNF receptor, GM-CSF receptor and the like. Accordingly, by detecting the phosphorylation activity on tyrosine, serine and/or threonine, for example, it is possible to evaluate signal transduction via Synoviolin. At this time, by evaluating the action of the test compound in the presence of Synoviolin ligand, it is possible to evaluate the effect of the test compound on the signal transduction of Synoviolin triggered by a Synoviolin ligand. Specifically, it is possible to detect the activity of blocking or suppressing the signal transduction via a Synoviolin ligand to Synoviolin. As the Synoviolin ligand, the Synoviolin ligand S1-5 described herein can be used. Alternatively, by evaluating the action of the test compound in the absence of Synoviolin ligand, it is possible to evaluate the stimulation activity of the test compound to Synoviolin.

In order to detect the phosphorylation of protein, for example, Synoviolin-expressing cells together with the test compound and [$^{32}$P] orthophosphate are incubated both in the presence of, and in the absence of the Synoviolin ligand. Next, by immune precipitation, the phosphorylated protein is recovered from this cytolysis product. After fractionation by SDS-PAGE, the phosphorylation of the protein thus recovered can be detected by autoradiography. Phosphorylated amino acids can be identified by TLC or other known methods of peptide analysis.

Alternatively, phosphorylated tyrosine antibodies or other antibodies specific to phosphorylated protein can be used to detect the phosphorylation of specific amino acids.

Typically, the phosphorylation of signal-transduction factors in the cell is transduced sequentially to a plurality of molecules. To wit, a series of transduction paths constitutes a cascade. For this reason, by evaluating changes in the phosphorylation level of the entire protein in the cell, it is possible to compare the magnitude of the phosphorylation signal occurring in the cell. Methods of evaluating the phosphorylation level of the total protein in the cell are known. For example, after cells are stimulated with Synoviolin ligand or the like, the protein is fractionated by SDS-PAGE and blotted on a filter, and then the phosphorylation level of the entire protein can be evaluated by Western blot using anti-phosphorylated tyrosine antibodies or the like. In addition, for example, the cells are labeled with [$^{32}$P] orthophosphate, and the cells are stimulated with Synoviolin ligand or the like. Then, the cell protein is expanded with two-dimensional electrophoresis. The protein is stained with Coomassie blue and autoradiography is performed. By detecting the phosphorylated spot, it is possible to evaluate the phosphorylation level.

Alternatively, it is possible to specifically measure the change in the phosphorylation level in the phosphorylated protein that is the substrate of Synoviolin. The phosphorylated protein that is the substrate of Synoviolin is, for example, recovered from the phosphorylated spot in the aforementioned two-dimensional electrophoresis and can be identified by microsequencing or mass spectrometry. Changes in the phosphorylation level of the identified substrate protein is subjected to, for example, immune precipitation using antibodies specific to the substrate protein, and after fractionation by SDS-PAGE, the intake of [$^{32}$P] may be measured by autoradiography or evaluated by Western blotting using anti-phosphorylated tyrosine antibodies (*Baio Manyuaru Shirīzu—Bunshi Seibutsugaku Kenkyū no Tame no Tampaku Jikken Hō* [Bio Manual Series—Protein Experimental Methods for Molecular Biology Research], Tadaomi Takenawa, Masaki Inagaki eds.).

Examples of cells used in the aforementioned method include synovial cells (e.g. RTF) and cells into which the synoviolin gene is exogenously transferred. If the level of phosphorylation or dephosphorylation due to Synoviolin decreases for a certain test compound, then the compound is judged to be a compound that blocks signal transduction via Synoviolin. In addition, if the level of phosphorylation or dephosphorylation due to Synoviolin increases for a certain test compound, then the compound is judged to be a compound that promotes signal transduction via Synoviolin.

For example, in the case where Synoviolin functions as a receptor-type tyrosine kinase and the downstream molecule is activated via tyrosine phosphorylation to transduce a signal, if tyrosine phosphorylation is suppressed by the test compound, then this compound is judged to be a compound that blocks signal transduction via Synoviolin. In addition, the present invention relates to a method of blocking signal transduction via Synoviolin using, for example, tyrosine kinase, tyrosine phosphatase or serine/threonine kinase or other protein kinase or phosphatase blocker.

In addition, another good example of signal transduction via Synoviolin is ubiquitination signals. A protein structure prediction system (SMART: Simple Modular Architecture Research Tool (also see the http web site smart.embl-heidelberg.de/) Schultz et al., *Proc. Natl. Acad. Sci. USA* (1998) 95:5857-5864; Schultz, et al., *Nucleic Acids Res.* (2000) 28:231-234) demonstrated the presence of a ring finger motif in Synoviolin (Joazeiro, C. A., et al., *Science* (1999) 286:309-312). This motif is known to be present in the E3 ubiquitin-protein ligase related to the decomposition of protein. In addition, the ring finger motif is thought to be the binding site for E2 ubiquitin-conjugating enzymes.

Accordingly, by detecting the ubiquitination signal due to Synoviolin, it is possible to evaluate signal transduction via Synoviolin. The ubiquitination signal is evaluated, for example, by detecting ubiquitination of the substrate protein using anti-ubiquitin antibodies. In addition, the binding of Synoviolin to E2 ubiquitin-conjugating enzyme or substrate protein, or the Synoviolin-containing ubiquitin ligase complex may also be detected. Specifically, for example, cells transfected with a vector that expresses tagged Synoviolin are ruptured and [$^{32}$P]-labeled ubiquitin is added. After reaction is allowed to proceed, immunoprecipitation is performed with anti-tag antibodies. The ubiquitin ligase activity of Synoviolin can be detected by SDS-PAGE and performing autoradiography (Hashizume, R., et al., *J. Biol. Chem.* (2001) 276:14537-14540).

Changes in the level of ubiquitination in the substrate protein of Synoviolin can be measured specifically. The substrate protein of Synoviolin can be identified by, for example, yeast two-hybrid screening using Synoviolin as a bait. Changes in the ubiquitination level of the identified substrate protein can be evaluated as follows: the tagged substrate is purified, and purified E1, E2, E3 and ubiquitin are added thereto. After reaction is allowed to proceed, immune precipitation is performed with anti-tag antibodies, and staining is performed with anti-ubiquitin antibodies (Yokouchi, M., et al., *J. Biol. Chem.* (1999) 274:31707-31712).

If the activation of the ubiquitination signal by Synoviolin decreases for a certain test compound, then the compound is judged to be a compound that blocks signal transduction via Synoviolin. In addition, if the activation of the ubiquitination signal increases for a certain test compound, then the compound is judged to be a compound that promotes signal transduction via Synoviolin. For example, compounds that inhibit the interaction between Synoviolin and E2 ubiquitin activation enzyme can effectively inhibit the ubiquitination signal via Synoviolin. In addition, the present invention provides a method of using a inhibitor of enzymes related to the ubiquitination signal to shut off signal transduction via Synoviolin. For example, by applying the E2 ubiquitin conjugating enzyme or the E3 ubiquitin ligase inhibitor to cells, it is possible to block signal transduction via Synoviolin.

The method described above can be used to select compounds that have the activity of regulating signal transduction via Synoviolin. Compounds that block signal transduction via Synoviolin are useful as agents for the treatment of diseases caused by the activation of Synoviolin. For example, compounds that block signal transduction via Synoviolin are useful in synovial hyperplasia blocking. By administering these compounds, it is possible to suppress synovial hyperplasia and thus it is possible to prevent or treat diseases such as RA that involve synovial hyperplasia. In addition, these compounds may also be used as drugs for treating ML and DHRD. Alternatively, compounds that promote signal transduction can be used as an agent that stimulates Synoviolin, or agent that promotes bone formation, etc. For example, they can be used as drugs for treating osteoporosis, bone disruption, sports injuries or the like.

Based on the discovery of the synoviolin gene, the following new research becomes possible regarding RA and other diseases in which Synoviolin is involved. First, it is possible to determine the structure of the promoters or enhancers that control the expression of Synoviolin. To wit, it is possible to advance the cloning of the genome based on the nucleotide sequence of the synoviolin gene shown in SEQ ID NO: 1, and analyze the sequence of the expression control domain. The thus-obtained transcription regulation domain for synoviolin can be used in the search for a transcription regulating factor for synoviolin.

In addition, in the synoviolin knock-out animal according to the present invention, if a marker gene is knocked in and the marker gene is expressed under the control of the endogenous promoter of the synoviolin gene, it is possible to perform a screening for drugs that control the expression of the synoviolin gene, using this animal or the animal-derived cells with the expression of the marker gene as an index. For example, if the recognition sequence for the transcription regulating factor is given as a double strand, then it functions as a decoy nucleic acid drug.

In addition, the polynucleotide according to the present invention may be used to examine, in animals, the biological role of the protein according to the present invention. In order to do this, for example, the DNA according to the present invention is introduced and the protein according to the present invention is overexpressed or expressed at different locations (or expressed at different times). Thus, its role can be examined by verifying its effect. A gene can be transferred into the entire body by preparing a transgenic animal of the DNA according to the present invention. Alternatively, through gene targeting and the administration of antisense oligonucleotides, ribozymes and the like, loss-of-function experiments on the suppression of the expression and functions of the DNA of the present invention are also effective. To wit, the present invention provides transgenic non-human vertebrate in which the expression of the DNA of the present invention is modified or said modifications can be induced. Expression may be modified in comparison to that of the wild type or, in the case where modification is induced, expression may be modified in comparison to that before the induction.

The transgenic animals according to the present invention include animals wherein exogenous nucleic acids are transferred into the genome. In addition, the "expression of DNA" may be at the DNA transcription level or at the translation level of transcripts. In addition, the "induction of modifications" may include the induction of modification by external stimulus or modification of stage-specific expression, or that expression is modified in later generations due to crossbreeding. In addition, it includes the modification of expression in some cells or tissues. Examples of the transgenic non-human vertebrates according to the present invention preferably include mammals (e.g., mouse, rat, hamster, rabbit, pig, goat, sheep, horse and bovine), while rodents, e.g. mouse and rat and the like are particularly used.

The transgenic non-human vertebrates according to the present invention include transgenic non-human vertebrates into which DNA that encodes the protein according to the present invention is exogenously introduced. Such transgenic animals can be produced by, for example, injecting, into a fertilized egg, a vector that expresses the DNA that encodes the protein according to the present invention.

The transfer of vectors can be performed by treatment with calcium phosphate after the mixing of vector and egg, electroporation, or microinjection under an inverted microscope, etc. In addition, the transfection is also performed by transferring a vector according to the present invention into an embryonic stem cell (ES cell), and by performing the microinjection of a selected ES cell into a fertilized egg (blastocyst).

The fertilized egg thus obtained may be implanted into the fallopian tubes of a recipient in which a false pregnancy is induced through mating with a vasectomized male individual, thereby obtaining a newborn. DNA is prepared from the tail of the newborn or the like and PCR is used to confirm that the transferred DNA was kept (Brigid Hogan, et al., eds., "Manipulating the Mouse Embryo: A Laboratory Manual," Cold Spring Harbor Laboratory, 1994, Gordon, J. W., et al., Proc. Natl. Acad. Sci. USA (1980) 77:7380-7384; Jaenisch, R. and Mintz, B., Proc. Natl. Acad. Sci. USA (1974) 71:1250-1254). A heterozygote can be obtained from a chimeric animal into which the genes are transferred into the germ line by breeding with a normal animal. A homozygote can be obtained by the breeding of two heterozygotes. The transgenic non-human vertebrates according to the present invention include these and their descendents.

Examples of the promoters used for expressing the DNA of the present invention in vivo include whole body expression type promoters and tissue-specific and stage-specific promoters.

Examples of whole body expression type promoters include β-actin promoters and the like. For example, chicken β-actin promoter linked to a human cytomegalovirus enhancer contained in pCAGGS or the like may be used. In the case of preparing a transgenic animal wherein the DNA according to the present invention is expressed in a site-specific or stage-specific manner, a Cre-loxP system or the like can be used. For example, a transgenic animal having a Cre recombinase gene downstream of a site-specific or stage-specific promoter is prepared and separately a transgenic animal having a vector in which DNA that encodes the polypeptide of the present invention is linked downstream of a general-use promoter is prepared. At this time, a transcription termination signal or the like or a stop codon sandwiched between a loxP pair is inserted between the promoter and the DNA that encodes the polypeptide of the present invention. By mating two individuals, it is possible to express the polypeptide of the present invention with the expression of Cre.

In addition, the transgenic non-human vertebrates according to the present invention encompass transgenic non-human vertebrates wherein the expression of DNA that encodes the endogenous protein of the present invention is suppressed. Such transgenic animals can be prepared by gene targeting, for example. In order to produce such transgenic non-human vertebrates, for example, a targeting vector wherein some or all of the DNA according to the present invention is made defective by substitution, deletion, addition and/or insertion or the like is inserted into an embryonic stem (ES) cell, and cells wherein homologous recombination with chromosome DNA has occurred are selected. Known methods of positive and negative selection can be performed in order to select homologous recombinants. Examples of markers used for positive selection include the neomycin resistance gene or other drug resistance genes, while examples of markers used for negative selection include the diphtheria toxin (DT)-A gene, HSV-tk gene and the like. Southern blotting, PCR or the like can be used to select correctly recombined cells. The cells thus obtained are inserted into a fertilized ovum at roughly the eight-cell stage or into the blastocoel of a blastocyst or the like, and transferred to the uterus of a pseudopregnant female individual prepared by mating with a vasectomized male. Genomic DNA analysis of the newborn is performed in the same manner as above, and a heterozygote or homozygote can be obtained. Not only the target gene can be knocked out, but another gene can also be knocked in. There is no particular limitation on the knocked-in genes. Examples include the lacZ gene or other marker genes.

In addition, transgenic non-human vertebrates wherein the expression of the DNA that encodes the endogenous protein according to the present invention is suppressed may be prepared using the antisense method or ribozyme method. In the antisense method, a vector containing DNA that encodes RNA complementary to the DNA transcription product that encodes the protein according the present invention, or in the ribozyme method, for example, a vector containing DNA that encodes RNA that cuts the transcription product of DNA that encodes the protein according the present invention is inserted into a embryonic stem cell of a mammal in the same manner as above. This is injected into a mammal embryo and individuals are obtained from the embryo.

Since Synoviolin induces the synovial hyperplasia symptoms of RA, the following applications are conceivable for transgenic animals. To wit, after incorporating the synoviolin gene or SL gene into an appropriate animal to form a transgenic animal, it can be used as a model for RA by inducing overexpression. In this transgenic animal, it is possible to proceed with the screening of drugs that control the mechanism of synovial hyperplasia. Alternatively, in animals wherein the RA symptoms do not occur with human Synoviolin/SL, they can be utilized as a source of supply of Synoviolin or SL by inducing the overexpression of these genes.

Transgenic animals that express the synoviolin gene exhibit symptoms common to RA such as arthritis accompanying synovial hyperplasia. To wit, these animals become rheumatoid arthritis model animals. These animals can be used to perform the testing or screening of various compounds including candidate compounds for RA drugs. By administering test compounds to the transgenic animals, it is possible to observe the remission or exacerbation of symptoms to verify the effectiveness of compounds or perform screening. Examples of methods of using the transgenic animals according to the present invention to perform testing or screening include the following methods.

A method of testing or screening for compounds that cause the remission or exacerbation of joint abnormalities, which is a method comprising the steps of: (a) administering a test compound to a transgenic non-human vertebrate into which the DNA according to the present invention is exogenously inserted, and (b) evaluating the joint abnormalities of the animal to which it was administered.

In addition, synoviolin gene knock-out animals can be used to examine the side effects caused by the suppression of the action of Synoviolin, and can be used in the assay or screening of drugs that reduce these side effects. In addition, by expressing Synoviolin locally or transiently in knock-out animals, it is possible to perform the specific verification of the effects of Synoviolin. In addition, from the association of SL (S1-5) and ML/DHRD, it is possible that Synoviolin may contribute to the intracellular signal transduction of SL, and thus, synoviolin knock-out animals may become models of ML or DHRD. For example, a tissue-specific or stage-specific (homozygous or heterozygous) knock-out of the synoviolin gene is conceivable.

A knock-in animal wherein a marker gene or the like is introduced at the time of the knock-out of the synoviolin gene can be used to detect the activity of the compound to increase or decrease the expression of the synoviolin gene. To wit, the present invention relates to a method of detecting the activity of a test compound to regulate the expression of the synoviolin gene, comprising the following steps of:

a) applying the test compound to the aforementioned knock-in animal or knock-in cells, and b) measuring the expression level of the marker gene.

This detection method can be used in the screening of compounds that regulate the expression of the synoviolin gene. This method is a screening method for compounds that regulate the expression of the synoviolin gene, comprising the following steps of: a) applying the test compound to the aforementioned knock-in animal or knock-in cells, b) measuring the expression level of the marker gene, and c) selecting compounds that increase or decrease the expression of the knocked-in gene.

To wit, in the animal or cell to which the test compound is applied, the expression of the marker gene is detected and compounds that increase or decrease the expression of the marker gene are selected. The detection of the expression of the marker gene in the case that LacZ is used as a marker can be performed by the method recited in Examples. By this method, in addition to the testing or screening using individuals, for example, it is possible to use isolated organs or tissues and perform similar testing or screening using cells obtained from transgenic animals.

In screening using individuals, the test compound is administered via an appropriate route. The test compound may be administered by known methods of administration such as intravenous injection, hypodermic injection, intramuscular injection, intraabdominal injection, oral administration, rectal administration, nasal administration or the like. In the event that screening is performed using a test tube culture system, the test compound may be added to the culture medium, for example. Alternatively, it may be injected into the cell by microinjection or other methods. In the event that the test compound is a gene, the naked DNA may be combined with a desired transfection reagent or incorporated into a known expression vector and the gene is introduced into the cell. Nucleic acids that include the sequence of the promoter domain of the synoviolin gene are expected to act as a decoy and suppress the expression of Synoviolin.

The activity of regulating the expression of the synoviolin gene can be detected, for example, by the following steps of:

a) contacting a test compound with an expression system that expresses a reporter gene under the control of the endogenous promoter of Synoviolin or a polynucleotide functionally equivalent to Synoviolin, and b) measuring the expression level of the reporter gene.

Moreover, based on this detection method, the screening of compounds that regulate the expression of the synoviolin gene can be performed. To wit, the present invention relates to a method of screening for compounds that regulate the activity of endogenous promoters of Synoviolin or polynucleotides functionally equivalent to Synoviolin, comprising the following steps of:

a) measuring the activity of test compounds to regulate the activity of the endogenous promoter of Synoviolin or a polynucleotide functionally equivalent to Synoviolin by the aforementioned method of detecting activity, and b) selecting the test compounds that have a difference in said activity in comparison to a control.

As a control, the same manipulation as in step a) may be performed in the absence of the test compound. Alternatively, this may be a control wherein the test compound is present at a concentration lower than that of step a). In addition, it is also possible to perform the same manipulation in step a) using a different compound, for example, and thus select compounds that have an action higher than that of that compound. The expression of genes includes expression at the transcription level or expression at the translation level. The gene linked downstream of the endogenous promoter of the synoviolin gene may be the natural synoviolin gene itself or an artificially linked reporter gene. The endogenous promoter activity of the synoviolin gene can be determined by detecting the transcription products or translation products of said gene by, for example, Northern hybridization using cDNA fragments of a gene linked downstream as the probe, RT-PCR, Western blotting using antibodies to the proteins encoded by said gene, immune precipitation, ELISA or other methods.

In addition, by producing a construct wherein a reporter gene is linked downstream of the promoter of the synoviolin gene, and using the transformed cell obtained by transfecting this into a cell, it is possible to perform screening using the expression of the reporter gene as an index. Such a construct can be prepared by linking the desired reporter gene downstream of the genome DNA in the upstream domain of the synoviolin gene that contains the promoter of the synoviolin gene. There are no particular limitations on the reporter gene, and examples include LacZ, chloramphenicol acetyl transferase (CAT), luciferase, GFP (green fluorescent protein) and others. Compounds that decrease the expression of the synoviolin gene are candidates for drugs for treating RA.

There are no particular limitations on the test compounds used in the testing or screening according to the present invention, and examples thereof include organic compounds, inorganic compounds, peptides, proteins, natural or synthetic low-molecular weight compounds, natural or synthetic polymers, extracts of tissues or cells, microbial culture supernatants and natural ingredients derived from plants or marine organisms, but they are not limited to these. Expression products of gene libraries or expression cDNA libraries and the like may also be used. In addition, compounds obtained by the aforementioned screening of compounds that bind to Synoviolin, or by screening of compounds that block the binding of Synoviolin to SL can also be administered as test compounds.

There are no particular limitations on the method of administering compounds, and this can be performed in vitro by contact with cells, including addition to culture medium, or by the introduction into cells using a microinjector or transfection reagent, etc. This can be performed in vivo by intraarterial injection, intravenous injection, hypodermic injection, intraabdominal administration, oral administration, rectal administration, intramuscular administration, eye drops, nasal administration, local injection into joints, etc., or other methods known to persons skilled in the art. The compounds are administered as an appropriate composition obtained by mixing with water, physiological saline solution, buffer solution, salt, stabilizer, preservative, suspension agent or the like.

In addition, the screening of compounds that regulate the expression of the synoviolin gene can be performed using not only transgenic animals but also normal animals or cells or the like derived from those animals. For example, the present invention relates to a method of detecting the activity of regulating the expression of Synoviolin or polynucleotides functionally equivalent to Synoviolin, comprising the following steps of:

a) culturing cells that express Synoviolin or a polynucleotide functionally equivalent to Synoviolin in the presence of a test compound, and b) measuring the expression level of said polynucleotide.

Moreover, based on this detection method, the screening of compounds that regulate the expression of the synoviolin gene can be performed. To wit, the present invention relates to a method of screening for compounds that regulate the expression of Synoviolin or polynucleotides functionally equivalent to Synoviolin, comprising the following steps of:

a) detecting the activity of test compounds to regulate the expression of Synoviolin or a polynucleotide functionally equivalent to Synoviolin based on the aforementioned method of detecting activity, and b) selecting the test compounds that have a difference in said activity in comparison to a control.

The expression level of Synoviolin or a polynucleotide functionally equivalent to Synoviolin can be measured by the aforementioned method. In addition, all compounds that can be used as test compounds in the aforementioned and other screening methods can be used as the test compound in this screening method. As a control, the same manipulation as in step a) can be performed in the absence of the test compound, as described above.

Compounds identified by the testing or screening methods according to the present invention become candidates for drugs for RA and other diseases in which Synoviolin is involved, and thus, they can be used for the prevention or treatment of RA and other diseases. These compounds can consist of the active ingredient appropriately combined with other solutes or solvents to form pharmaceutical compositions. In the case of using, as a pharmaceutical agent, a compound isolated by the screening method according to the present invention, it is possible to administer the isolated compound itself directly to patients, or the compound may be administered as a pharmaceutical composition prepared by known pharmaceutical methods.

For example, it can be prepared and administered appropriately in combination with any pharmaceutically acceptable carrier or medium, specifically sterilized water, physiological saline solution, plant oils, emulsifiers, suspension agents or the like. The pharmaceutical composition according to the present invention may take the form of an aqueous solution, tablet, capsule, troche, buccal tablet, elixir, suspension, syrup, nose drops, inhalation solution or the like. The content of the compound may be determined appropriately. Administration to patients may be performed typically by intraarterial injection, intravenous injection, hypodermic injection, oral administration, injection in the joint, etc., or other methods known to persons skilled in the art.

While the dosage varies depending on the weight and age of the patient, the method of administration, symptoms and the like, a person skilled in the art would be able to select the dosage appropriately. The typical dosage would differ depending on the effective blood concentration and the metabolism time of the drug, but the daily maintenance dose is thought to be about 0.1 mg/kg to about 1.0 g/kg, or preferably about 0.1 mg/kg to about 10 mg/kg, or even more preferably about 0.1 mg/kg to about 1.0 mg/kg. Administration can be performed either at one time or divided into several times. In addition, as long as said compound can be encoded by the polynucleotide, gene therapy can be performed by incorporating said polynucleotide into a gene therapy vector.

All prior art references cited herein are incorporated by reference.

The following examples are offered to illustrate but not to limit the invention.

EXAMPLE 1

Preparation of Anti-Synovial Cell Anti-Serum

Anti-synovial cell anti-serum was obtained using, as an immunogen, synovial cells prepared by the following procedure. Synovial tissue extracted by synovectomy from ten rheumatoid arthritis (RA) patients was washed in phosphate buffered saline (PBS) in a sterile state. The washed tissue was cut to a size of approximately 5 mm square and 0.25% trypsin/PBS digestion was performed at 37° C. for 20 minutes. Excess tissue lumps were removed from the digested synovial tissue and the cells thus obtained were suspended in Dulbecco's modified Eagle's medium containing 10% fetal calf serum (*Virology* (1959) 8:396) (10% FCS-DMEM) and cultured for 24 hours in a sterilized cell culture Petri dish under 5% $CO_2$ at 37° C. The culture supernatant was discarded, washing was performed using 10% FCS-DMEM, and the non-adhering cells were removed to obtain rheumatism patient-derived synovial cells as cells adhered to the Petri dish (*The Journal of Clinical Investigation* (1993) 92:186). The cultured cells were used as a pool and used in experiments as the following synovial cells derived from RA patients.

Patient-derived synovial cells ($1 \times 10^5$) were suspended in 20 mL of 10% FCS-DMEM and cultured in a 76 $cm^2$ culture flask. The culture medium was changed every 3 days and the culture surface was filled with cells after two weeks, at which time the culture medium was removed and 7 mL each of 0.05% EDTA/PBS and 0.1% trypsin/PBS were added to detach and recover the cells. The recovered cells were washed in PBS to remove the culture medium components, and suspended in 1 mL of PBS to form an immunogen.

This immunogen was used within 2 hours after preparation to immunize one rabbit by intravenous injection into the ear. Immunization was performed 6 times in total at one-week intervals. At the time of the sixth immunization, when several mL of blood drawn from the ear of the rabbit was tested for anti-serum, it was found by the fluorescent antibody method that the anti-serum reacted with the synovial cells of rheumatism patients. One week after the sixth immunization procedure, a catheter was used to draw as much blood as possible from the heart. This blood was kept overnight at 4° C. to coagulate and the serum was separated. As a preservative, 0.1% sodium azide was added to the serum and the serum was stored at 4° C. as anti-synovial cell anti-serum.

EXAMPLE 2

Figure 1:
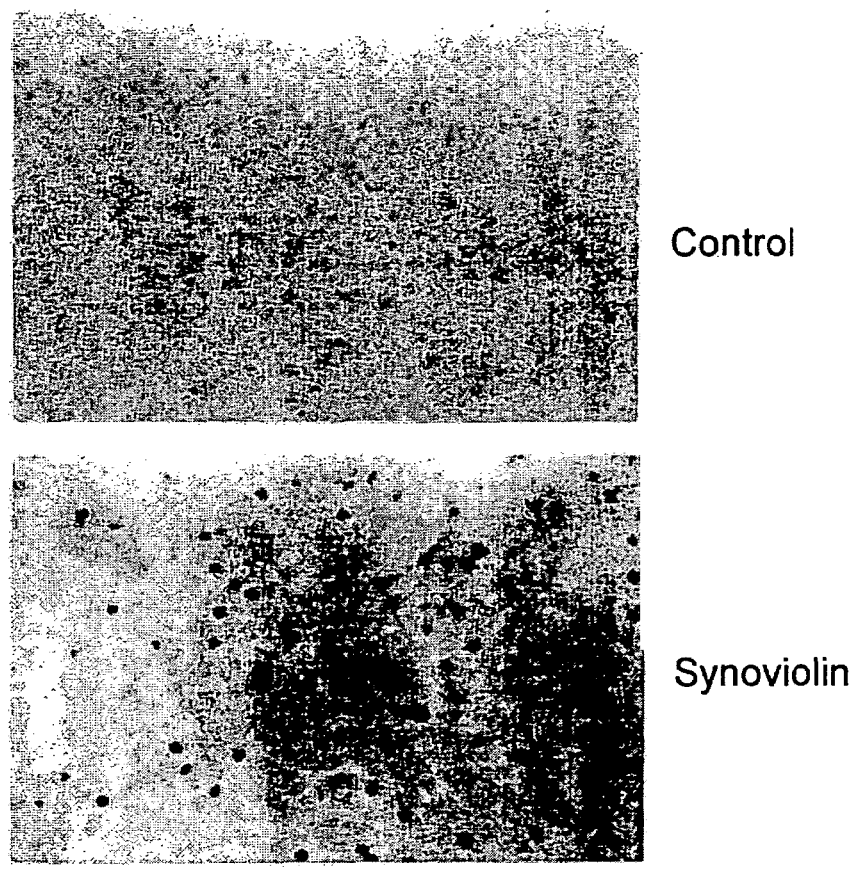
FIG. 1 indicates photographs of positive colonies in immunoscreening by anti-synovial cell anti-serum.

Gene Cloning of an Antigen (Synoviolin) Recognized by Anti-Synovial Cell Anti-Serum The acid guanidine/phenol chloroform method was used to extract the total RNA from the synovial cells of ten RA patients obtained in Example 1, and poly T beads were used to purify the mRNA (Analytical Biochemistry, 162, 159, 1987). The λZAP vector (Stratagene) was used to prepare a cDNA library of RA patient synovial cells by the ordinary method. A picoBlue immunoscreening kit (Stratagene) was used to perform immunoscreening with the anti-synovial cell anti-serum of Example 1 above (FIG. 1). The positive clone (phage) thus obtained was converted to a plasmid pBluescript II SK (+) with a helper phage. The nucleotide sequence of the DNA inserted into the pBluescript II SK (+) was determined with an ABI PRISM 377 DNA Sequencer (PERKIN ELMER) using M13PrimerM4 and M13PrimerRV (Takara) based on the dye terminator method (*Proc. Natl. Acad. Sci. USA*. (1977) 74:5463). The nucleotide sequence was determined from the 3' end of the gene (named "synoviolin") that encodes the antigen recognized by the above anti-synovial cell anti-serum, and a 2990 bp nucleotide sequence including a poly(A)$^+$ chain was clarified (SEQ ID NO: 1, No. 42-3031). Using this nucleotide sequence, a 3031 bp nucleotide sequence including the coding region of full-length synoviolin, a portion of the 5'-non-coding region and a poly(A)$^+$ chain (SEQ ID NO: 1) was determined from the synovial cell cDNA library by the 5'-RACE (Rapid Amplification of cDNA Ends) method (*Proc. Natl. Acad. Sci. USA*. (1988) 85:8998-9002). As a result of performing a homology search in GenBank, this nucleotide sequence was found to be a new gene, with no similar sequence being reported.

EXAMPLE 3

Expression of Partial Synoviolin Recombinant Protein in *E. coli*

From a cDNA clone obtained by immunoscreening using anti-synovial cell anti-serum, cDNA that encodes a portion of Synoviolin (1799 bp; SEQ ID NO: 1, No. 1233-3031) was treated with the restriction enzymes EcoRI and XhoI and extracted. The cDNA which has a sequence recognized by EcoRI/XhoI at its ends was inserted into the glutathione S-transferase (GST) fusion protein expression vector pGEX-5X-3 and subcloning was performed. pGEX-5X-3 into which a portion of the synoviolin cDNA was inserted was introduced into the BL21 *E. coli* strain by 45-second heat shock at 42° C. to obtain BL21/synoviolin-GST gene/pGEX-5X-3. This BL21 was cultured in an LB medium containing 0.1 mg/mL ampicillin, 0.1 mM isopropylthio-β-D-galactoside (IPTG) was added, and it was cultured for an additional 2 hours at 37° C. to induce the expression of the aforementioned fusion protein. After the BL21 recovered by centrifugation was washed in PBS, the BL21 was digested with 1 mg/mL lysozyme and solubilized with 0.1% Triton X-100. The BL21-derived protein suspension containing solubilized GST fusion protein was applied to Glutathione Sepharose 4B (GS4B) and then washed with PBS, and 50 mM reduced form of glutathione/PBS was used to purify the desired GST-partial Synoviolin fusion protein.

EXAMPLE 4

Expression of Full-Length Synoviolin Recombinant Protein in *E. coli*

Synoviolin cDNA (syno-HAHA) comprising the cDNA (1851 bp; SEQ ID NO: 1, No. 60-1910) that encodes Synoviolin obtained in Example 2 to which two molecules of an influenza hemagglutinin (HA)-tag were added at the 3'-end was inserted into the glutathione S-transferase (GST) fusion protein expression vector pGEX-5X-1 and subcloning was performed. pGEX-5X-1 into which the syno-HAHA gene was inserted was introduced into the BL21 *E. coli* strain by 45-second heat shock at 42° C. to obtain BL21/syno-HAHA/pGEX-5X-1. This BL21 was cultured in an LB medium containing 0.1 mg/ml ampicillin, 0.1 mM isopropylthio-β-D-galactoside (IPTG) was added, and it was cultured for an additional 3 hours at 30° C. to induce the expression of the Synoviolin protein with GST fused to the N terminus and HA fused to the C terminus (GST-Synoviolin-HAHA). After the BL21 recovered by centrifugation was washed in PBS, the BL21 was digested with 1 mg/ml lysozyme and solubilized with 0.1% Triton X-100. The BL21-derived protein suspension containing solubilized GST-Synoviolin-HAHA protein was applied to Glutathione Sepharose 4B (GS4B) and then washed with PBS, and 50 mM reduced form of glutathione/Tris-HCl (pH 8.0) was used to purify the desired GST-Synoviolin-HAHA protein.

Figure 2:
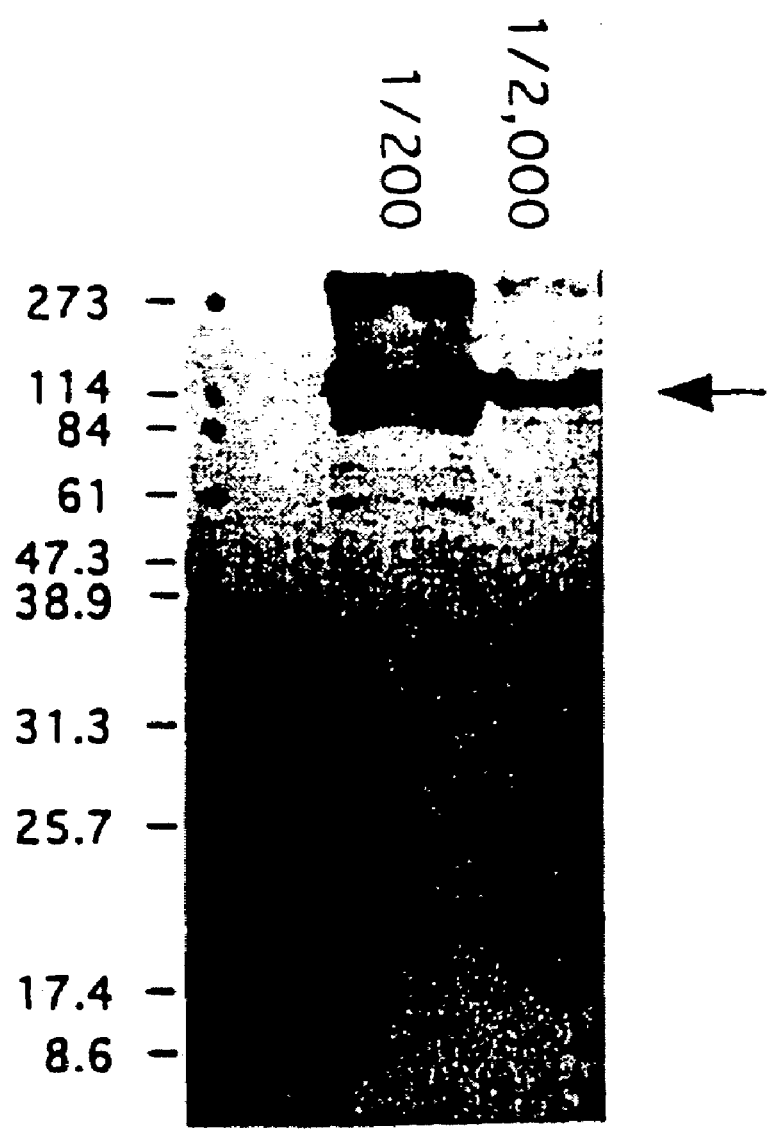
FIG. 2 indicates a photograph showing the expression of Synoviolin recombinant protein in E. coli.

Confirmation of expression was performed by 200 times and 2000 times diluting the fractions eluted with 50 mM reduced form of glutathione, by treating them with 25 mM Tris-HCl (pH 6.8), 0.25% sodium dodecyl sulfate (SDS), 0.05% mercaptoethanol and 0.1% glycerol, and then by applying them to 8% SDS polyacrylamide electrophoresis (SDS-PAGE). After SDS-PAGE, GST-Synoviolin-HAHA protein was transferred to a nylon membrane by electroblotting. This nylon membrane underwent blocking for 60 minutes at room temperature in PBS containing 5% skim milk, and then underwent immune reaction for 60 minutes at room temperature with anti-HA monoclonal antibodies (Boehringer Mannheim) diluted 400 times with PBS containing 0.5% skim milk. After the reaction, it was washed with 0.1% Tween 20/PBS, subjected to an immune reaction for 60 minutes at room temperature with horseradish peroxidase (HRP) labeled mouse IgG antibodies as the secondary antibodies, and washed with 0.1% Tween 20/PBS, and the target antigen was detected by detecting HRP activity. The detection of HRP activity was performed using an ECL kit (Amersham) (Clinical Chemistry, 25, p. 1531, 1979). The results are shown in FIG. 2. From the molecular weight size of the aforementioned GST-Synoviolin-HAHA fusion protein, the molecular weight of the Synoviolin protein is estimated to be approximately 80 kDa.

EXAMPLE 5

In Vitro Expression of Full-Length Synoviolin Recombinant Protein

Figure 3:
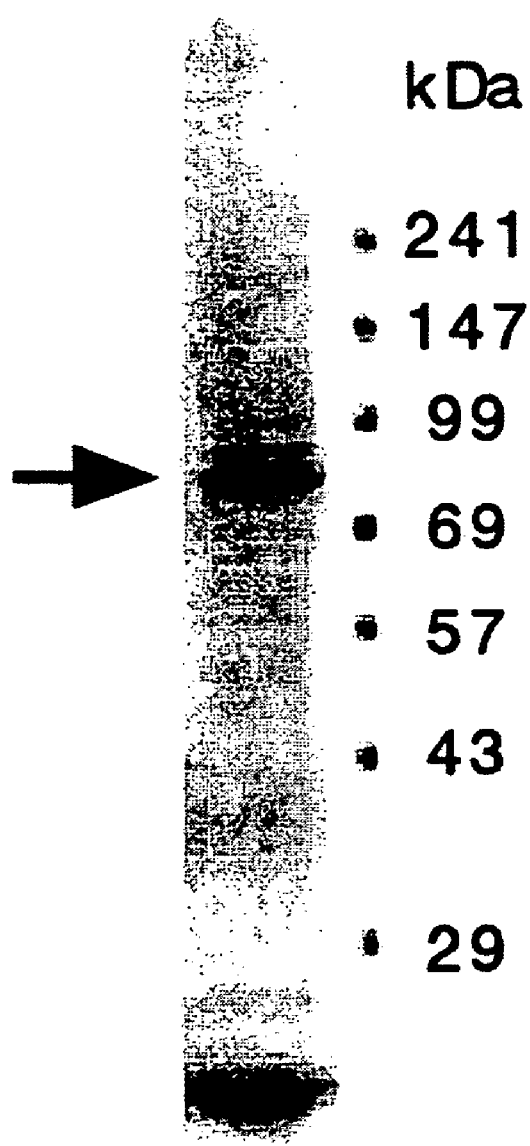
FIG. 3 indicates a photograph of an autoradiograph showing the Synoviolin protein expression translated from synoviolin cDNA in vitro.

The end of the synoviolin gene (SEQ ID NO: 1) was modified with the restriction enzyme EcoRI and inserted into the pBluescript II KS vector (syno/pBluescript). Thereafter, syno/pBluescript (1 μg) and TNT-coupled Translation System (Promega) were used with in vitro translation to express the Synoviolin protein in vitro as an [$^{35}$S]-labeled protein. The [$^{35}$S]-labeled Synoviolin protein was applied to 10% SDS-PAGE and its radioactivity was detected with an image analyzer (BAS2000, Fujix). The results are shown in FIG. 3. The molecular weight according to SDS-PAGE of the Synoviolin protein translated in vitro from the synoviolin gene was found to be approximately 80 kDa.

EXAMPLE 6

Figure 4:
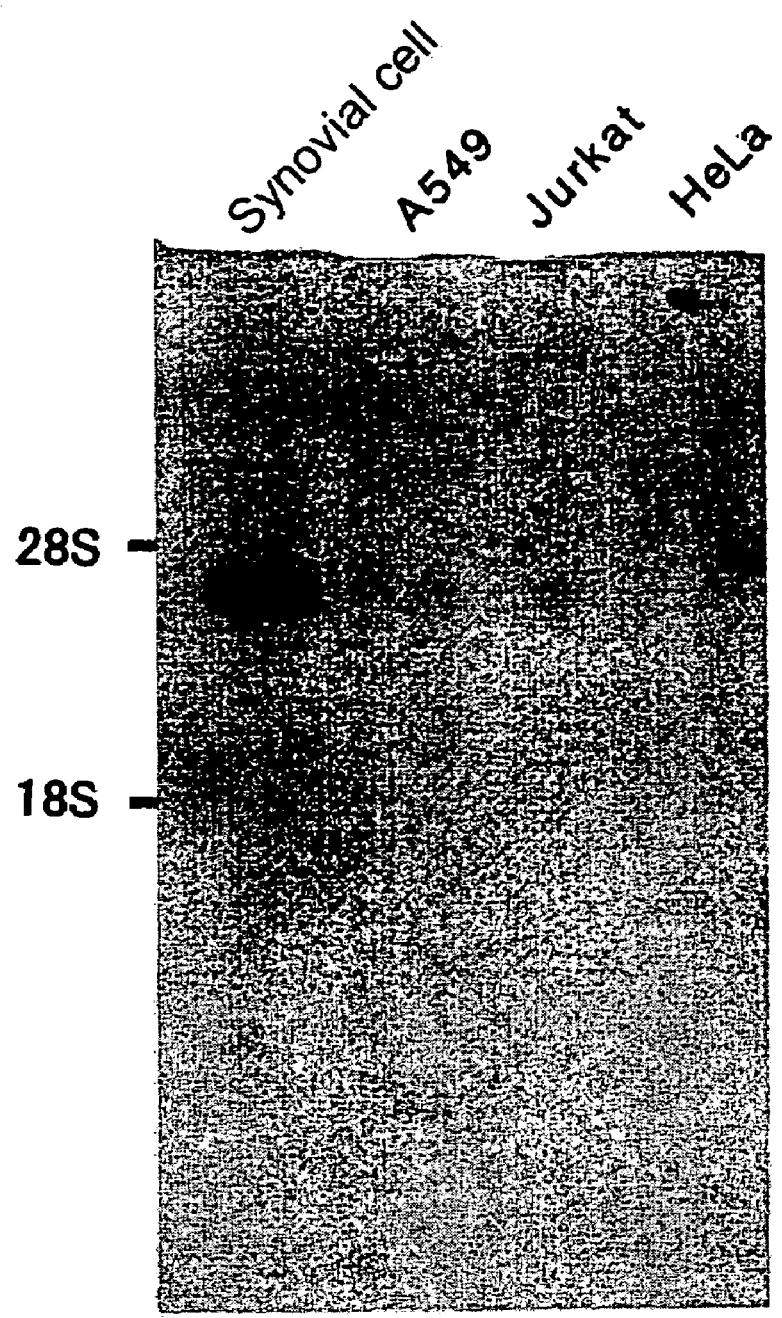
FIG. 4 indicates a photograph of an autoradiograph showing the results of analysis of synoviolin gene expression by Northern blotting using the cDNA of Synoviolin as a probe.

Confirmation of Expression of the Synoviolin Gene by Northern Blotting mRNA was obtained by ordinary methods from RA patient-derived synovial cells obtained in Example 1, the A549 cell line, Jurkat cell line and the HeLa cell line. 1 μg of this mRNA was separated by 1% agarose gel electrophoresis and transferred to a nylon membrane by contact blotting. The nylon membrane was treated for 2 hours at 80° C., and pre-hybridization was performed for 2 hours at 42° C. in Denhardt's solution. Next, using $^{32}$P radiolabeled synoviolin cDNA (1799 bp; SEQ ID NO: 1, No. 1233-3031) as a probe, hybridization was performed for 12 hours at 42° C. After the reaction, the nylon membrane was washed in 300 mM NaCl and 30 mM sodium citrate, and then 15 mM NaCl and 1.5 mM sodium citrate were used to perform washing again at 50° C. The desired mRNA was detected by exposure to X-ray film. The autoradiograph obtained as a result is shown in FIG. 4. The synoviolin gene was found to be expressed strongly in RA patient-derived synovial cells.

EXAMPLE 7

Confirmation of Expression of Synoviolin in Various Cells by Western Blotting

The state of expression of Synoviolin was confirmed by Western blotting using the following cells as specimens.

RA patient-derived synovial cells prepared in Example 1
Human umbilical vein endothelial cells (HUVEC)
HEK (human embryonic kidney)-293T
GST-partial Synoviolin fusion protein prepared in Example 3 (positive control)

First, the various cells used as specimens were solubilized in 1% NP-40 to prepare cell lysates. Each of the cell lysates was treated with 25 mM Tris-HCl (pH 6.8), 0.25% sodium dodecyl sulfate (SDS), 0.05% mercaptoethanol and 0.1% glycerol, and then separated with 8% SDS polyacrylamide electrophoresis (SDS-PAGE). After SDS-PAGE, protein derived from the various cells was transferred to a nitrocellulose (NC) membrane by electroblotting. On this NC membrane, anti-synovial cell anti-serum was diluted 1000 times with Tris buffered saline (TBS) containing 2.0 mg/mL GST-partial Synoviolin fusion protein and 5% skim milk, and subjected to immune reaction for 60 minutes at room temperature. In addition, as negative controls, an experiment wherein the same antibody solution is reacted with the NC membrane, and an experiment wherein the GST-partial Synoviolin fusion protein in the antibody solution is replaced with GST alone were performed at the same time. After the reaction, the NC membrane was washed with 0.1% Tween 20/TBS, subjected to an immune reaction for 60 minutes at room temperature with horseradish peroxidase (HRP) labeled anti-rabbit IgG antibodies as the secondary antibodies, and washed with 0.1% Tween 20/TBS, and the target antigen was detected by detecting HRP activity. The detection of HRP activity was performed using an ECL kit (Amersham) (Clinical Chemistry, 25, p. 1531, 1979). The results are shown in FIG. 5.

Figure 5:
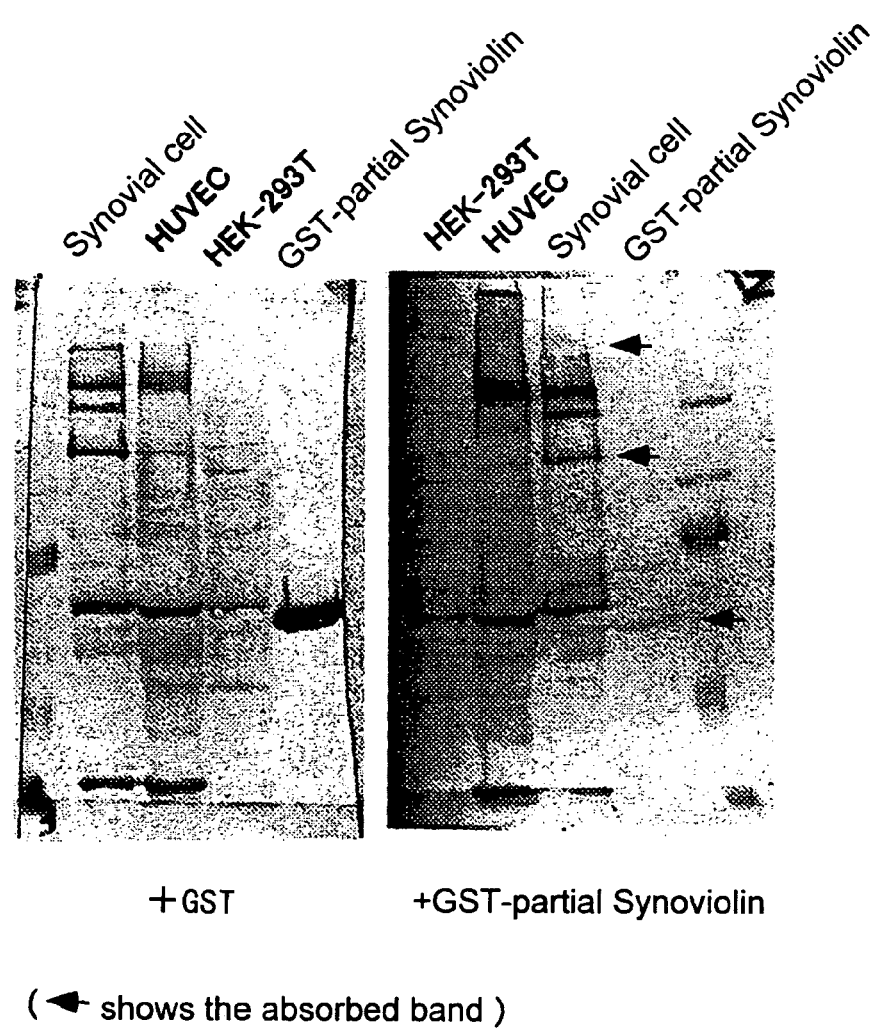
FIG. 5 indicates photographs showing the results of Western blotting using anti-synovial cell anti-serum on various cell extracts, and the results of antibody absorption experiments with GST-partial Synoviolin. The arrow shows the absorbed band. The molecular weights of the various bands are approximately 220, 185 and 140 kDa in order from the top.

GST-partial Synoviolin blocked the immune reaction of the anti-synovial cell anti-serum to the 220 kDa protein that was detected in RA patient-derived synovial cells in the control experiments (FIG. 5; +GST), and not detected in the HUVEC and HEK-293T cells, and partially blocked its immune reaction to the approximately 140 kDa protein and approximately 185 kDa protein (FIG. 5; +GST-partial Synoviolin).

The reactivity observed in bands other than 220-kDa band is presumed to be fibronectin (molecular weight: approximately 240 kDa) or subunits of laminin (molecular weight: approximately 200 kDa) determined by their reactivity to other antibodies. Based on the results of these experiments, the molecular weight of Synoviolin is presumed to be approximately 220 kDa. However, the molecular weight of Synoviolin as confirmed in Example 5 is approximately 80 kDa. From the difference between the two, it is conceivable that Synoviolin has an multimeric structure that is not dissociated in SDS.

EXAMPLE 8

Figure 6:
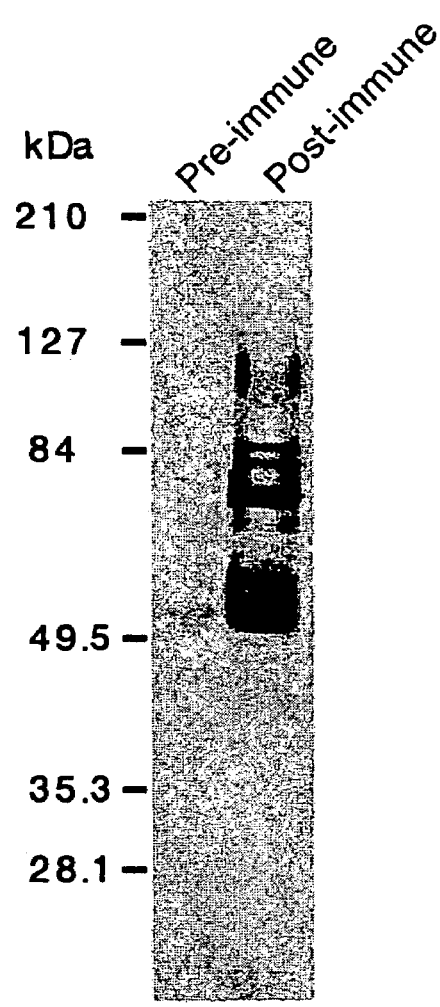
FIG. 6 indicates a photograph of an autoradiograph showing the results of Western blotting using anti-synovial cell anti-serum on synovial cell extracts. The left lane (pre-immune) is rabbit anti-serum prior to immunization of synovial cell, while the right lane (post-immune) is synovial cell anti-serum.

Confirmation of Expression of Synoviolin Protein in RA Patient-Derived Synovial Cells by Western Blotting The RA patient-derived synovial cells prepared in Example 1 were solubilized in 1% NP-40 to prepare cell extract fractions. This synovial cell extract was treated with 25 mM Tris-HCl (pH 6.8), 0.25% sodium dodecyl sulfate (SDS), 0.05% mercaptoethanol and 0.1% glycerol, and then separated by 8% SDS polyacrylamide electrophoresis (SDS-PAGE). After SDS-PAGE, the synovial cell-derived protein was transferred to a nitrocellulose (NC) membrane by electroblotting. On this NC membrane, anti-synovial cell anti-serum (in the figure, after immunization) obtained by immunizing RA patient-derived synovial cells was diluted 1000 times with Tris buffered saline (TBS) containing 5% skim milk, allowed to undergo blocking for 1 hour at room temperature with Tris buffered saline (TBS) containing 5% skim milk and subjected to immune reaction for 1 hour at room temperature. At the same time, serum drawn from a rabbit prior to the immunization of the rabbit with synovial cells (pre-immune) was used as a negative control. After reaction, the NC membrane was washed with 0.1% Tween 20/TBS, subjected to an immune reaction for 1 hour at room temperature with horseradish peroxidase (HRP) labeled anti-rabbit IgG antibodies as the secondary antibodies, and washed with 0.1% Tween 20/TBS, and the target antigen was detected by detecting HRP activity. The detection of HRP activity was performed using an ECL kit (Amersham) (Clinical Chemistry, 25, p. 1531, 1979). The results are shown in FIG. 6.

EXAMPLE 9

Confirmation of Expression of Synoviolin in Various Cells and Synovial Tissue by Immunostaining Immunostaining was performed by fixing synovial cells upon glass slides by the ordinary method, and immunostaining was performed using the anti-synovial cell anti-serum of Example 1. A sample subjected to 30-minute blocking with 1% bovine serum albumin (BSA) was allowed to undergo immune reaction for 60 minutes at room temperature with anti-synovial cell anti-serum diluted 100 times with 1% BSA. In addition, along with observation with anti-serum, experiments were also performed using anti-synovial cell antibodies purified from this anti-serum. Purified anti-synovial cell antibodies were prepared by immunoaffinity purification using GST-partial Synoviolin fusion protein as a ligand. The ligand used was a fusion protein expressed after the GST-fusion protein expression vector pGEX-5X-3 containing the 1799 bp synoviolin gene up to No. 1233-3031 of SEQ ID NO: 1 was transformed into BL21. A Glutathione Sepharose column was produced by the method of the Pharmacia Corp, to prepare a GST-partial syno-GS column. As a control for the case where purified anti-synovial cell antibodies were used, an anti-GST antibody obtained by the immunoaffinity purification of anti-serum in the same manner where GST was used as the ligand was used.

Figure 7:
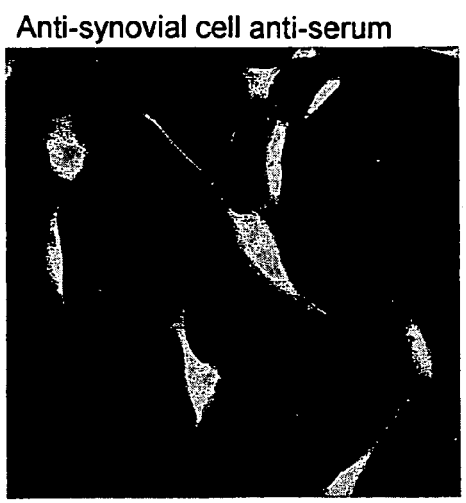
FIG. 7 indicates fluorescent microphotographs showing the results of fluorescent immunostaining on synovial cell with anti-synovial cell anti-serum (A) and purified anti-synovial cell antibodies (B).
Figure 7:
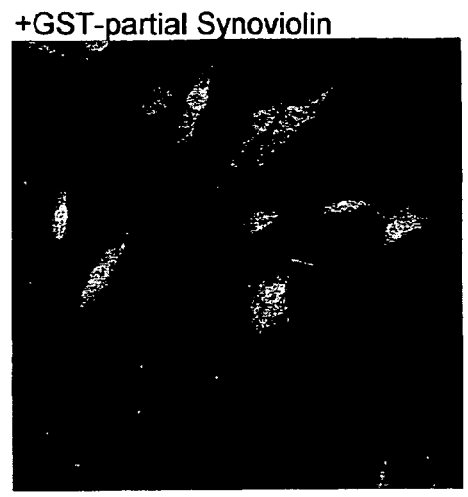
Figure 7:
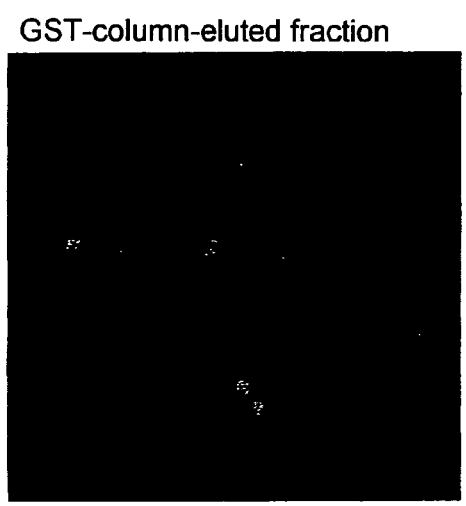
Figure 7:

After reaction, the sample was washed with PBS and then allowed to undergo immune reaction using fluorescein isothiocyanate-labeled anti-rabbit IgG antibodies as the secondary antibody. Confirmation of the antigen in the immune reaction with anti-synovial cell anti-serum was performed with a confocal laser microscope. The results are shown in FIG. 7. This anti-serum exhibited a strong immune reaction with RA patient-derived synovial cells, and it was confirmed that this immune reaction was blocked by the GST-partial Synoviolin fusion protein prepared in Example 3 (FIG. 7, top). Moreover, it was confirmed that the immune reaction became even stronger and positive for purified anti-synovial cell antibodies prepared from this anti-serum (FIG. 7, bottom).

Figure 8:
FIG. 8 indicates microphotographs showing the results of immunostaining using anti-synovial cell anti-serum on synovial tissue, and the results of antibody absorption experiments with GST-partial Synoviolin.
Figure 8:
Figure 8:
Figure 9:
FIG. 9 indicates microphotographs showing the results of immunostaining using purified anti-synovial cell antibody on synovial tissue. The results using anti-serum purified by a GST affinity column (upper panel) and anti-serum purified by a GST-partial Synoviolin affinity column (lower panel) are shown.
Figure 9:

The staining of RA patient-derived synovial tissue was performed by fixing synovial tissue upon glass slides by the ordinary method. A sample subjected to 30-minute blocking with 1% BSA was allowed to undergo immune reaction for 60 minutes at room temperature with anti-synovial cell anti-serum diluted 100 times with 1% BSA. After reaction, the sample was washed with PBS and then allowed to undergo immune reaction using HRP-labeled anti-rabbit IgG antibodies as the secondary antibody. Confirmation of the antigen in the immune reaction with anti-synovial cell anti-serum was performed by the coloring of 3,3'-diaminobenzidine tetrahydrochloride based on HRP activity. In the same manner as in the aforementioned Western blotting, GST-partial Synoviolin fusion protein was used to perform an anti-synovial cell anti-serum absorption test with respect to synovial tissue staining. Tissue staining was performed by adding 2.0 mg/mL of GST-partial Synoviolin fusion protein or GST (2.0 mg/mL) to anti-synovial cell anti-serum. The results are shown in FIG. 8. The staining of synovial tissue with anti-synovial cell anti-serum seen in the control was found to be weakened by GST-partial Synoviolin fusion protein (FIG. 8). In addition, the immunostaining of synovial tissue using the aforementioned purified antibodies from GST-partial Syno-GS was found to react positively in comparison to the antibodies obtained from GST-GS (FIG. 9).

Based on the results of Western blotting (Example 8) and immunostaining, it was confirmed that the Synoviolin protein recognized by anti-synovial cell anti-serum was expressed in RA patient-derived synovial cells and synovial tissue.

EXAMPLE 10

Presence of Anti-Synoviolin Antibodies in Serum of RA Patients

Figure 10:
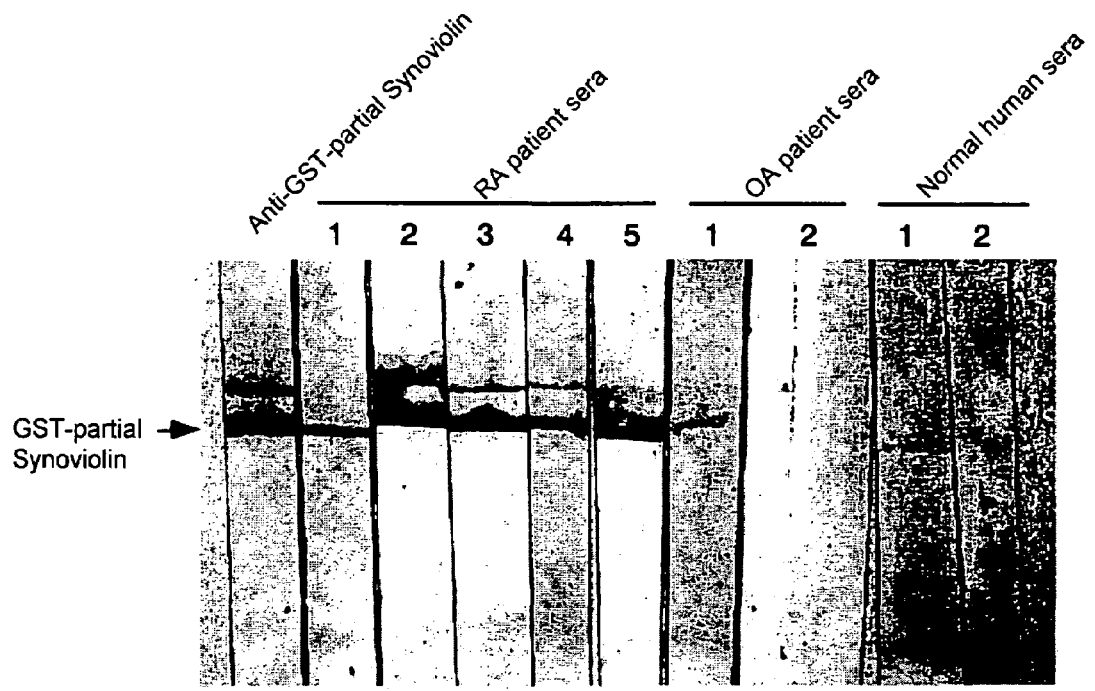
FIG. 10 indicates a photograph of an autoradiogram showing the results of detection of anti-Synoviolin antibodies in various types of human blood serum by Western blotting.

The present inventors attempted to detect anti-Synoviolin antibodies in the serum of RA patients by Western blotting using GST-partial Synoviolin fusion protein as the antigen. Using the same procedure as in Example 7, first, GST-partial Synoviolin fusion protein (100 ng/lane) was electrophoresed by SDS-PAGE and transferred to an NC membrane. As the primary antibodies, RA patient serum (5 cases) was diluted 1000 times with Tris buffered saline (TBS), and allowed to undergo immune reaction for 60 minutes at room temperature with the NC membrane onto which GST-partial Synoviolin fusion protein was transferred. The NC membrane was washed with 0.1% Tween 20/TBS, subjected to an immune reaction for 60 minutes at room temperature with HRP-labeled anti-human IgG antibodies as the secondary antibodies, and washed with 0.1% Tween 20/TBS, and the human IgG that reacted with the target antigen was detected by detecting HRP activity. The detection of HRP activity was performed in the same manner as in Example 7. The results are shown in FIG. 10. Anti-IgG antibodies against GST-partial Synoviolin fusion protein was found in the serum of RA-patients (five of five) (FIG. 10). On the other hand, antibodies that recognize GST-partial Synoviolin were not found in serum derived from osteoarthritis (OA) patients and normal human serum.

EXAMPLE 11

Identification of Synoviolin Ligand by Screening an Expression Library

Screening for the Synoviolin ligand was performed using the cDNA expression library derived from RA patient synovial cells prepared in Example 2 (Tadaomi Takenawa, Toshiki Watanabe, eds., *Baiomanyuaru UP Shirīzu "Tampakushitsu no Bunshikan Sōgosayō Jikken Hō"* [Bio-Manual UP Series "Protein Intermolecular Interaction Experimental Method"], pp. 66-67, Yodosha Co., Ltd.; Kaelin, W. G. et al., *Cell* 70, 351-364, 1992; Skolnik, E. Y. et al., *Cell* 65, 83-90, 1991; Sambrook, J. et al., Molecular Cloning, a laboratory manual second edition, Cold Spring Harbor Laboratory Press 12.16-12.20, 1989). The library phage was inoculated into *E. coli* (XL1-Blue MRF') by incubation for 20 minutes at 37° C., and spread upon a plate after mixing with Top agarose. After culturing for 3.5 hours at 42° C., a nitrocellulose membrane soaked in 10 mM IPTG and dried was placed upon a plate and culturing was performed for an additional 3.5 hours at 37° C. After the membrane was recovered, it was washed five times for 5 minutes in a washing buffer [10 mM Tris-HCl (pH 8.0), 0.5% skim milk, 0.1% Triton X-100, 150 mM NaCl, 1 mM EDTA, 5 mM $MgCl_2$, 1 mM DTT, protease inhibitor (complete, Boehringer Mannheim)] and soaked for 1 hour in a blocking buffer [10 mM Tris-HCl (pH 8.0), 5% skim milk, 0.1% Triton X-100, 150 mM NaCl, 1 mM EDTA, 5 mM $MgCl_2$, 1 mM DTT, 5% glycerol, protease inhibitor (complete, Boehringer Mannheim)]. After 5-minute washing was performed five times with the washing buffer, incubation was performed after adding, as a probe (approximately $10^6$ cpm/ml), GST-Synoviolin (the GST-partial Synoviolin fusion protein purified in Example 3) that was $^{32}$P-labeled with protein kinase A. Washing was performed repeatedly while changing the washing buffer until the count per membrane became approximately 1 kcpm, and then the signal was detected by autoradiography. As a result, a clone bound to Synoviolin was obtained. This clone was named Synoviolin ligand (SL).

Regarding the cDNA of SL, the nucleotide sequence was determined for 100 bp near its 5' end and 100 bp near its 3' end. Upon performing a database search based on the nucleotide sequence information thus obtained, the sequence in the 100 bp portion at the ends was found to be the same as that of a known gene called S1-5 [Lecka-Czernik, B. et al., Molecular and Cellular Biology, 15, 120-128, 1995; accession number U03877 (cDNA), AAA65590 (protein), also called "EFEMP1": Stone, E. M. et al., Nature Genetics 22, 199-202, 1999; accession number Q12805 (protein)]. The sizes of both genes are roughly the same, and the sizes of their translation products are roughly the same, suggesting that they are the same protein.

EXAMPLE 12

Figure 11:
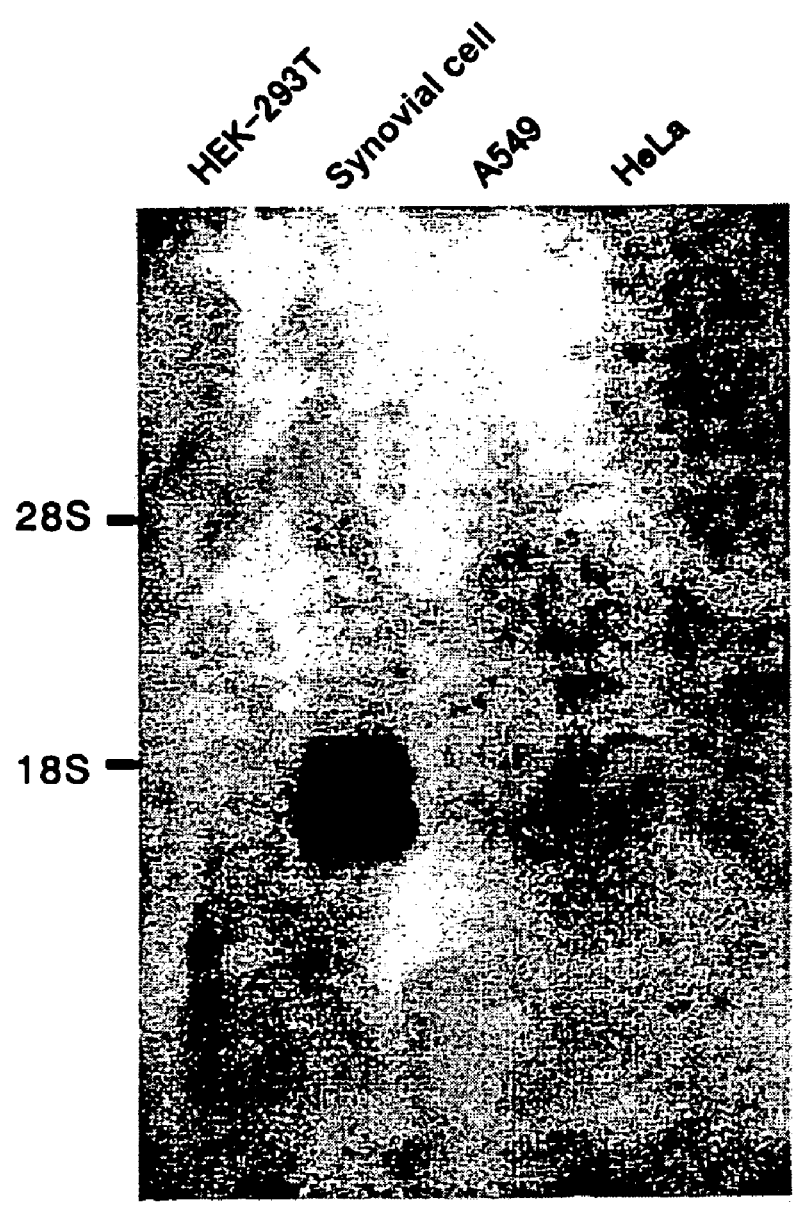
FIG. 11 indicates a photograph of an autoradiograph showing the results of analysis of the expression of the SL gene in synovial cells by Northern blotting using the cDNA of SL as a probe.

Expression of the SL Gene by Northern Blotting mRNA was extracted from various cells in the same manner as in Example 6, and Northern blotting was performed using the SL cDNA obtained in Example 11 as a probe. The cells used are those given below. The RA patient-derived synovial cells were found to exhibit overexpression of the SL gene (FIG. 11).
HEK-293T
RA patient-derived synovial cells prepared in Example 1
A549
HeLa

EXAMPLE 13

Binding of Synoviolin to SL

Figure 12:
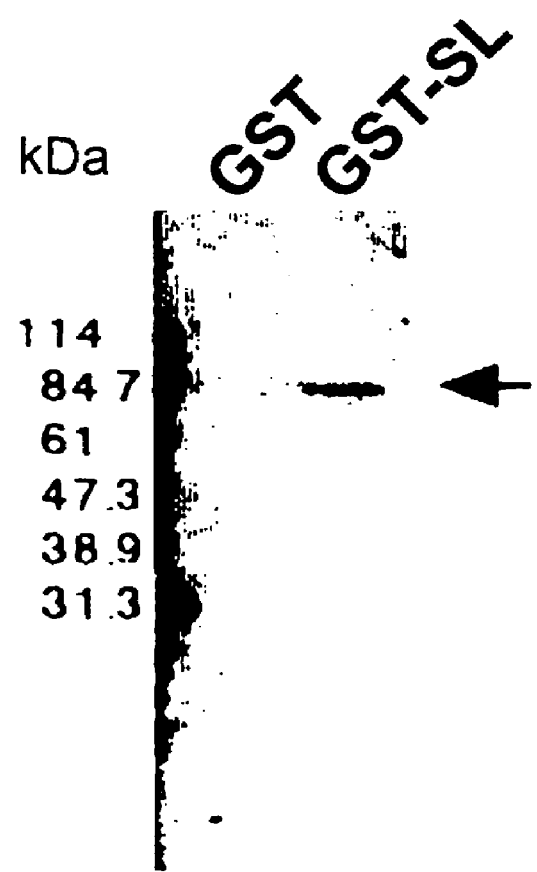
FIG. 12 indicates a photograph of an autoradiograph showing the binding between [$^{35}$S]-labeled HA-Synoviolin-HAHA and GST-SL fusion protein.

The SL cDNA was inserted into a pGEX vector in the same manner as in Example 3 to prepare GST-SL fusion protein, and the GST-SL (500 ng) was applied to 10% SDS-PAGE along with GST (1 μg) as a control. After SDS-PAGE, it was transferred to a nylon membrane by electroblotting. This nylon membrane was denatured for 1 hour at room temperature with 50 mM Tris-HCl (pH 8.0) containing 6M guanidine hydrochloride and 5 mM 2-mercaptoethanol, and regenerated overnight at 4° C. in 50 mM Tris-HCl (pH 8.0) containing 5 mM 2-mercaptoethanol and 0.05% Tween 20. The regenerated nylon membrane was treated with blocking buffer [10 mM Tris-HCl (pH 8.0), 5% skim milk, 0.1% Triton X-100, 150 mM NaCl, 1 mM EDTA, 5 mM $MgCl_2$, 1 mM DTT, 5% glycerol, protease inhibitor (complete, Boehringer Mannheim)] and washed in blocking buffer (same as above, except for 0.5% skim milk). Thereafter, the TNT-coupled Translation System (Promega) and pcDNA3-HA-synoviolin-HAHA (SEQ ID NO: 1 synoviolin cDNA 1851 bp; synoviolin cDNA with an HA-tag added at 60-1910 inserted into the expression vector pcDNA3) were used to perform in vitro translation, [$^{35}$S]-labeled HA-Synoviolin-HAHA fusion protein ([$^{35}$S]HA-Synoviolin-HAHA) was used as a probe, and the GST-SL and GST upon the nylon membrane were allowed to react for 2 hours at room temperature. This nylon membrane was washed in 10 mM Tris-HCl (pH 8.0), 0.5% skim milk, 0.1% Triton X-100, 150 mM NaCl, 1 mM EDTA, 5 mM $MgCl_2$, 1 mM DTT, and protease inhibitor (complete, Boehringer Mannheim), and its radioactivity was detected with an image analyzer (BAS2000, Fujix). Binding between the GST-SL fusion protein and [$^{35}$S]HA-Synoviolin-HAHA transferred to the nylon membrane was observed. In addition, binding was not observed in the control of GST and [$^{35}$S]HA-Synoviolin-HAHA (FIG. 12). From these results, Synoviolin and SL are presumed to bind by protein interaction.

In addition, in Example 14, results are obtained that suggest that hyperplasia of synovial cells is blocked through Synoviolin-based neutralization of Synoviolin ligand in a culture. Based on these results, mutants of SL that have a structure corresponding to the Synoviolin binding sites of SL are thought to possibly have the action of suppressing the hyperplasia of synovial cells by antagonistic blocking action on the binding of Synoviolin to SL. Moreover, Synoviolin mutants that have a structure corresponding to the SL binding sites of Synoviolin are also expected to have antagonistic blocking action in the same manner as SL mutants.

EXAMPLE 14

MTT Assay

Figure 13:
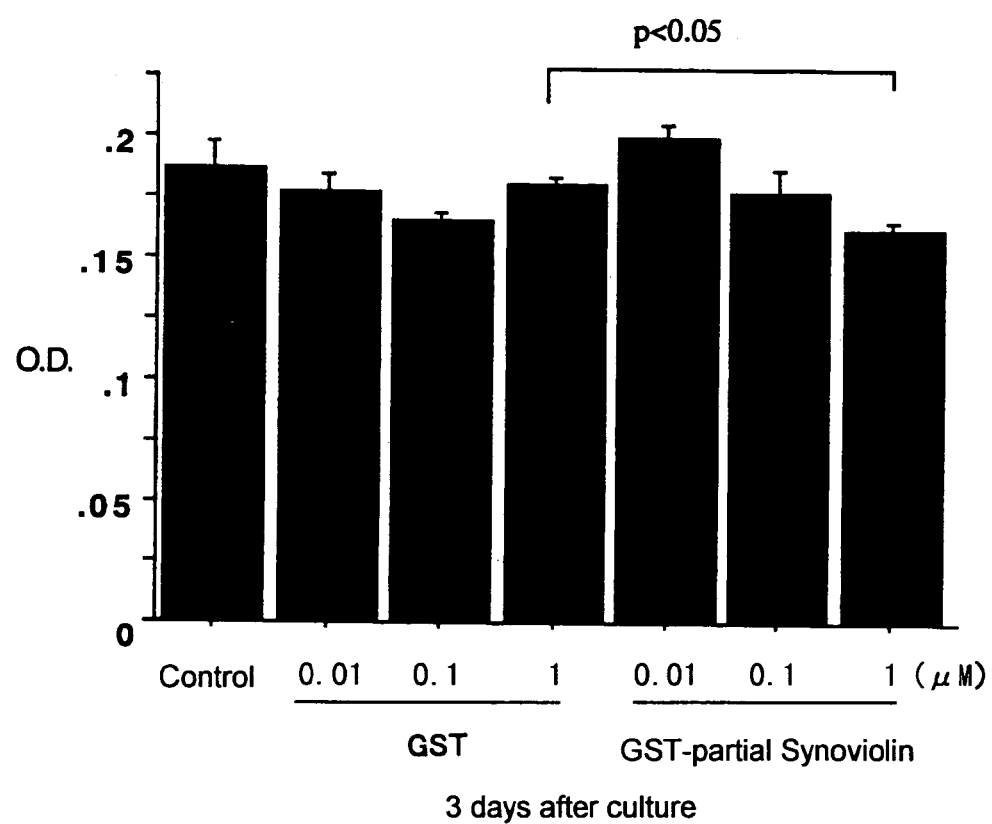
FIG. 13 indicates a diagram showing the results of analyzing the effect of Synoviolin on hyperplasia of synovial cells by MTT assay. GST-partial Synoviolin was used.

The RA patient-derived synovial cells prepared in Example 1 were used to prepare 96 well plates so that there were $5 \times 10^3$ cells/well, and GST or GST-partial Synoviolin was added to the cell supernatant so that the final concentration became 0.01 to 1 µM. After three days of culture, 3-(4, 5-dimethyl-2-thiazolyl)-2,5-diphenyl-2H-tetrazolium bromide (MTT)/PBS was added to the cell supernatant, and it was cultured for 3 hours under conditions of 37° C. and 5% $CO_2$. After culturing, the cell supernatant was removed, crystals of MTT formazan were dissolved with dimethyl sulfoxide, and absorbance measurement was performed (*Journal of Immunological Methods*, 65, 55, 1983). Under conditions of 10%-FCS/DMEM, 37° C., 5% $CO_2$, the RA patient-derived synovial cell hyperplasia was significantly suppressed by GST-partial Synoviolin (1 µM) (FIG. 13).

EXAMPLE 15

Preparation of a Synoviolin Gene-Introduced Mouse

Figure 14:
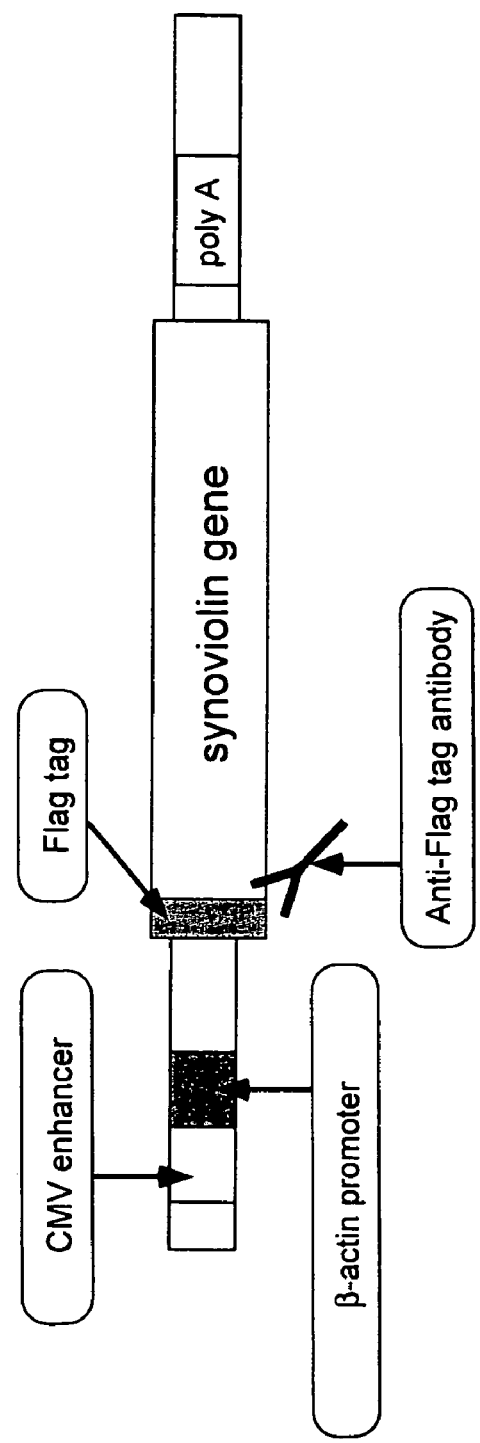
FIG. 14 indicates a diagram showing the structure of the synoviolin gene introduction vector. Synoviolin is systemically expressed using a β-actin promoter which has a CMV enhancer. The anti-Flag-tag antibody can be used to confirm the expression of the Flag tag-fusion Synoviolin protein.

A vector for expressing the synoviolin gene was constructed by linking a Flag tag to the N terminus of the DNA that encodes the Synoviolin protein and linking a poly(A) signal downstream of the 3' side. The vector is constructed based on pCAGGS (Niwa, H., et al., *Gene* (1991) 108:193-199) with a β-actin promoter as the promoter, and with human cytomegalovirus immediate early enhancer as the enhancer (FIG. 14).

The vector for expressing the synoviolin gene was injected into a mouse egg cell by microinjection using a microscopic glass pipette connected to a manipulator under a microscope. DNA was injected into the male pronucleus of a fertilized egg and the injected manipulated egg was transferred to the fallopian tubes of a female mouse (recipient mouse) in which false pregnancy was induced by breeding with a vasectomized male mouse. Mouse pups were obtained through natural parturition or cesarean section 19 days after transfer. In the case of a cesarean section, the mouse pups were nursed by a separately prepared female mouse as a foster mother. DNA was taken from each tail of the newborn mice and PCR was used to confirm that it carries the transgene.

Figure 15:
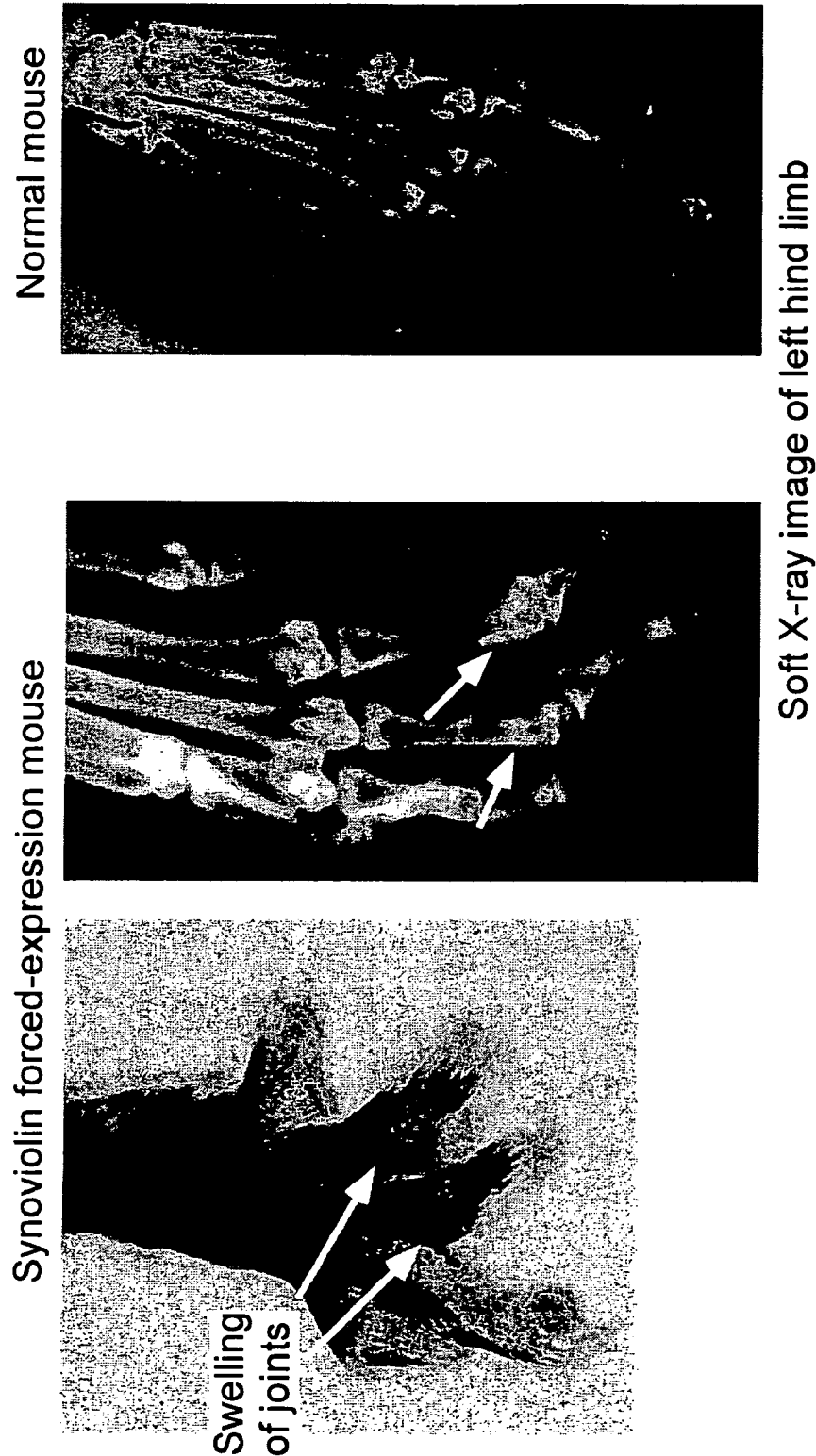
FIG. 15 indicates photographs showing toe joints that exhibit arthritis in a transgenic mouse with the synoviolin gene. The appearance and soft X-ray image of the toe of a Synoviolin forced-expression mouse are shown. A soft X-ray image of the toe of a normal mouse is shown at right for comparison. The Synoviolin forced-expression mouse exhibited marked swelling of the toe.

As a result, marked swelling of the joints was observed in Synoviolin overexpression mice. The rate of onset of arthropathy in synoviolin gene-expressed mice was found to be 33% (10 out of 30 individuals). Accordingly, the swelling of joints is thought to be not a natural-onset mouse deformation (the rate of onset of hydrocephaly in the C57B6 mouse is less than 1%) but rather due to the contribution of the Synoviolin molecule. A photograph taken by soft X-ray photography of the left hind limb of a Synoviolin overexpression mouse is shown (FIG. 15).

EXAMPLE 16

Histological Study of Joints

The present inventors performed a histological study of the toe joints of a synoviolin gene-expressed mouse (1 individual). Hematoxylin eosin (HE) staining of tissue sections of toe joint portions was performed. The hematoxylin eosin staining was performed according to known methods.

Figure 16:
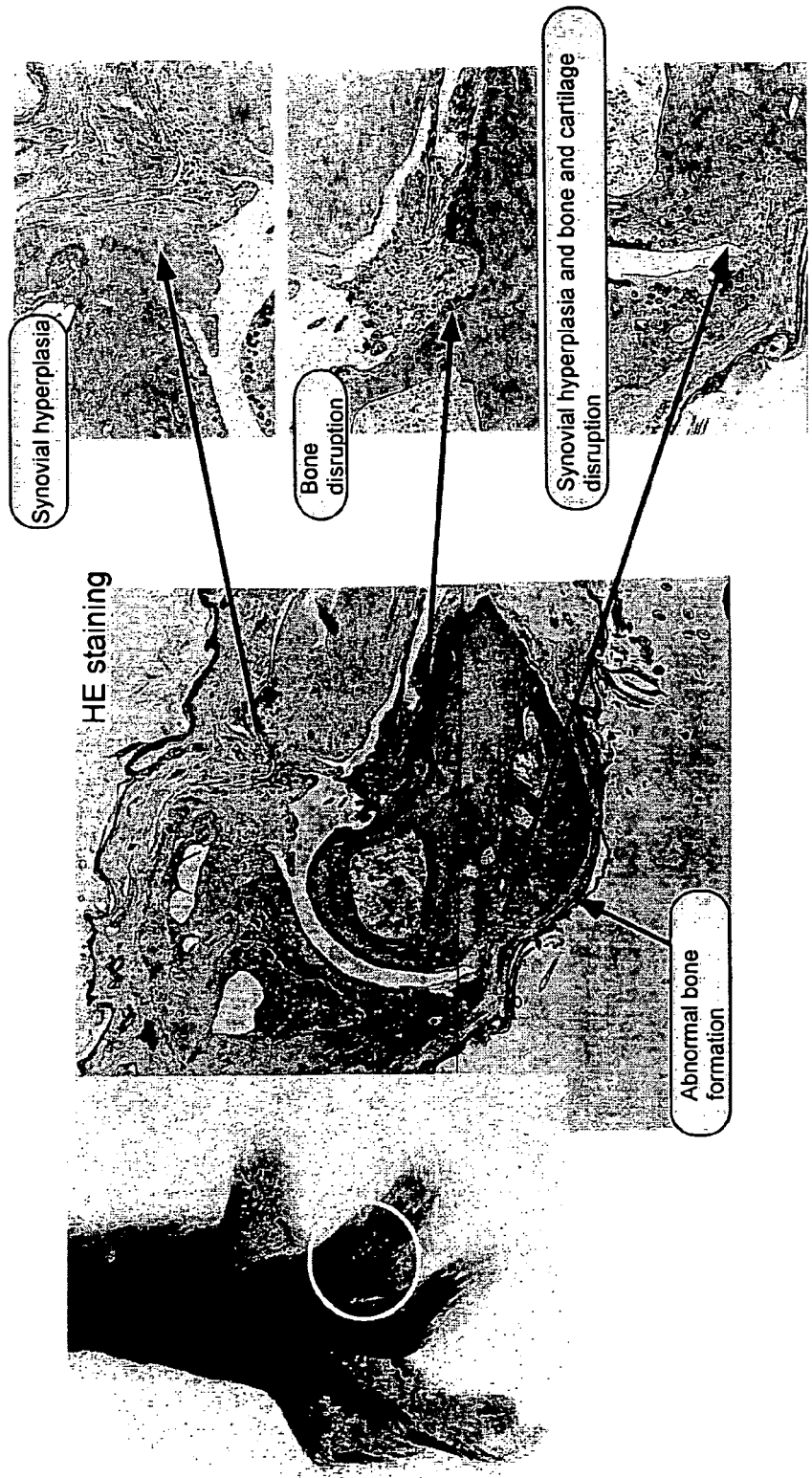
FIG. 16 indicates photographs showing the histological findings on toe joint that exhibits arthritis in a transgenic mouse with the synoviolin gene. In the joint portions of toes that exhibited marked swelling, marked bone disruption and abnormal bone formation accompanying synovial hyperplasia were found.

As a result of HE staining, bone disruption accompanying marked synovial hyperplasia and abnormal bone formation were found in portions that exhibited arthropathy (FIG. 16). On the other hand, the aforementioned findings were not observed in the normal toe joints of gene-expressed mice used as a control (FIG. 17, top).

Figure 17:
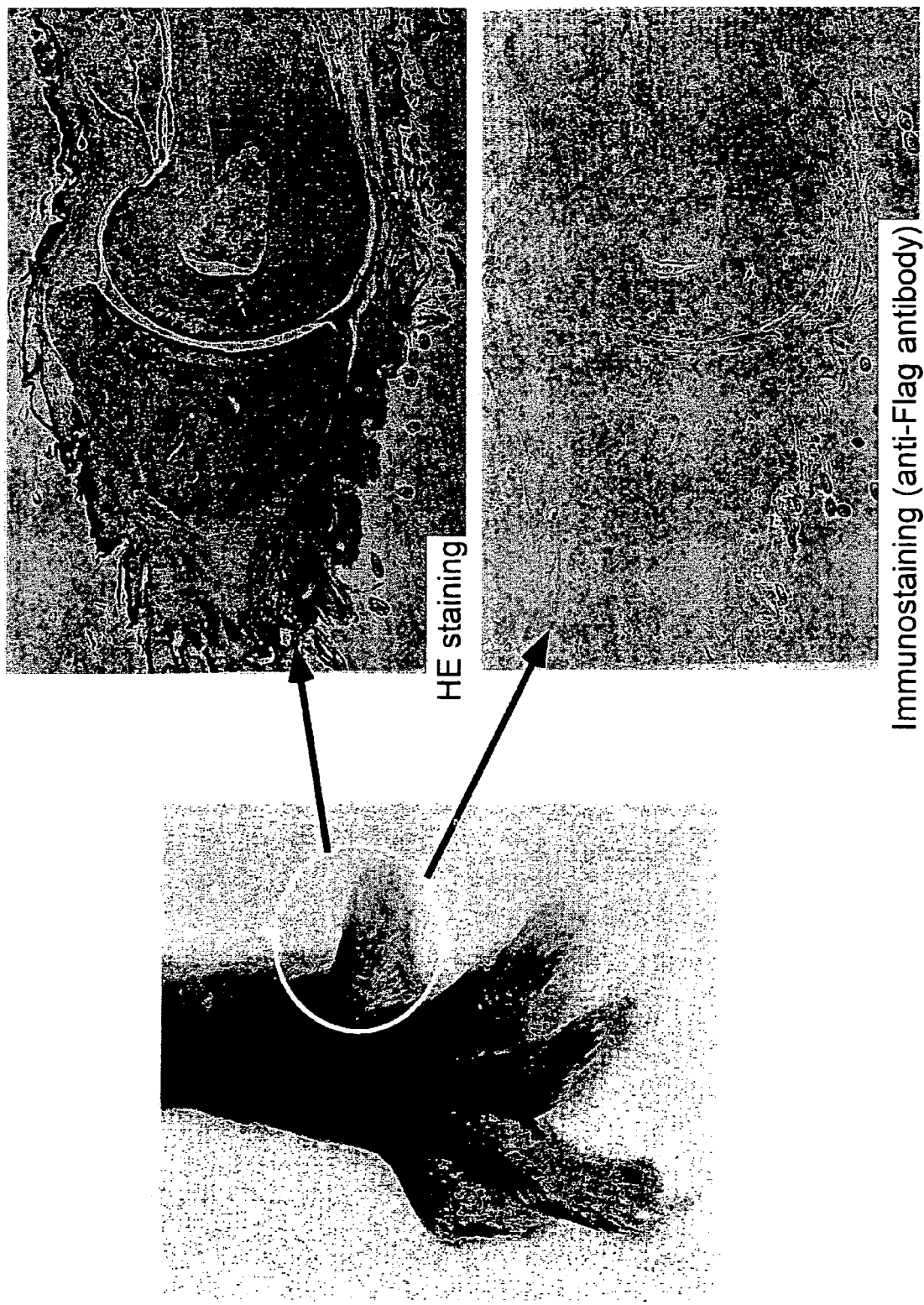
FIG. 17 indicates photographs showing the histological findings on normal toe joint of a gene-introduced mouse. No abnormal joint cartilage, bone disruption or synovial hyperplasia were found. The lower right panel shows the results of immunostaining with anti-Flag antibodies. No positive signal was observed.
Figure 18:
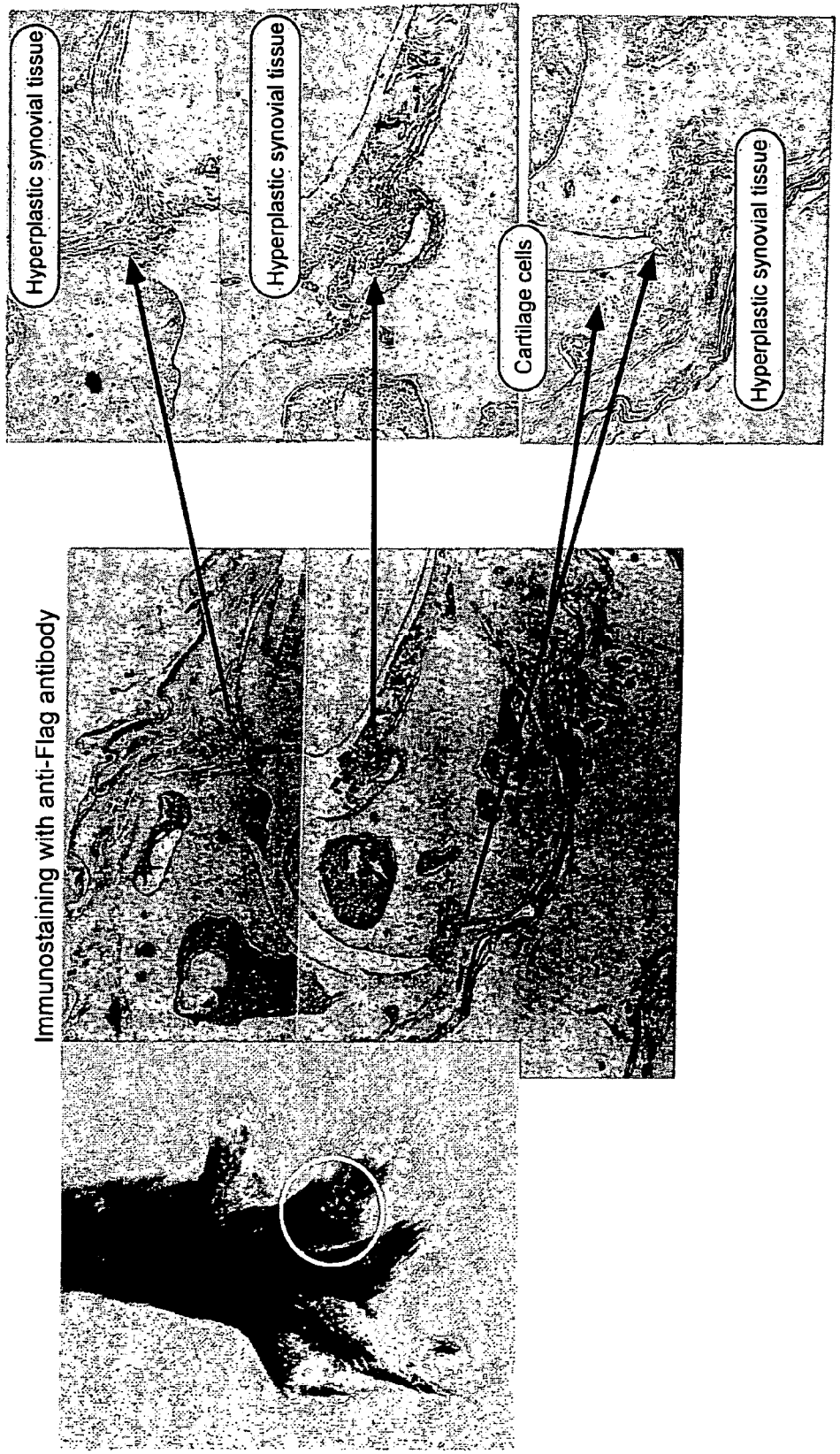
FIG. 18 indicates photographs that show the expression of Synoviolin in toe joints that exhibit arthritis in a synoviolin gene transgenic mouse. Immunostaining with anti-Flag antibodies was performed. The expression of Synoviolin was found in the hyperplastic synovial tissue and cartilaginous cells formed in the joint areas of toes that exhibited marked swelling.

In addition, as a result of performing immunostaining with anti-Flag antibodies in the toe joints, the expression of Synoviolin was found in the synovial tissues and cartilaginous cells that exhibited hyperplasia in synoviolin gene-expressed mice (FIG. 18), but the aforementioned findings were not observed in the normal toe joints of gene-expressed mice (FIG. 17, bottom).

EXAMPLE 17

Preparation of a Knock-Out Mouse

Figure 19:
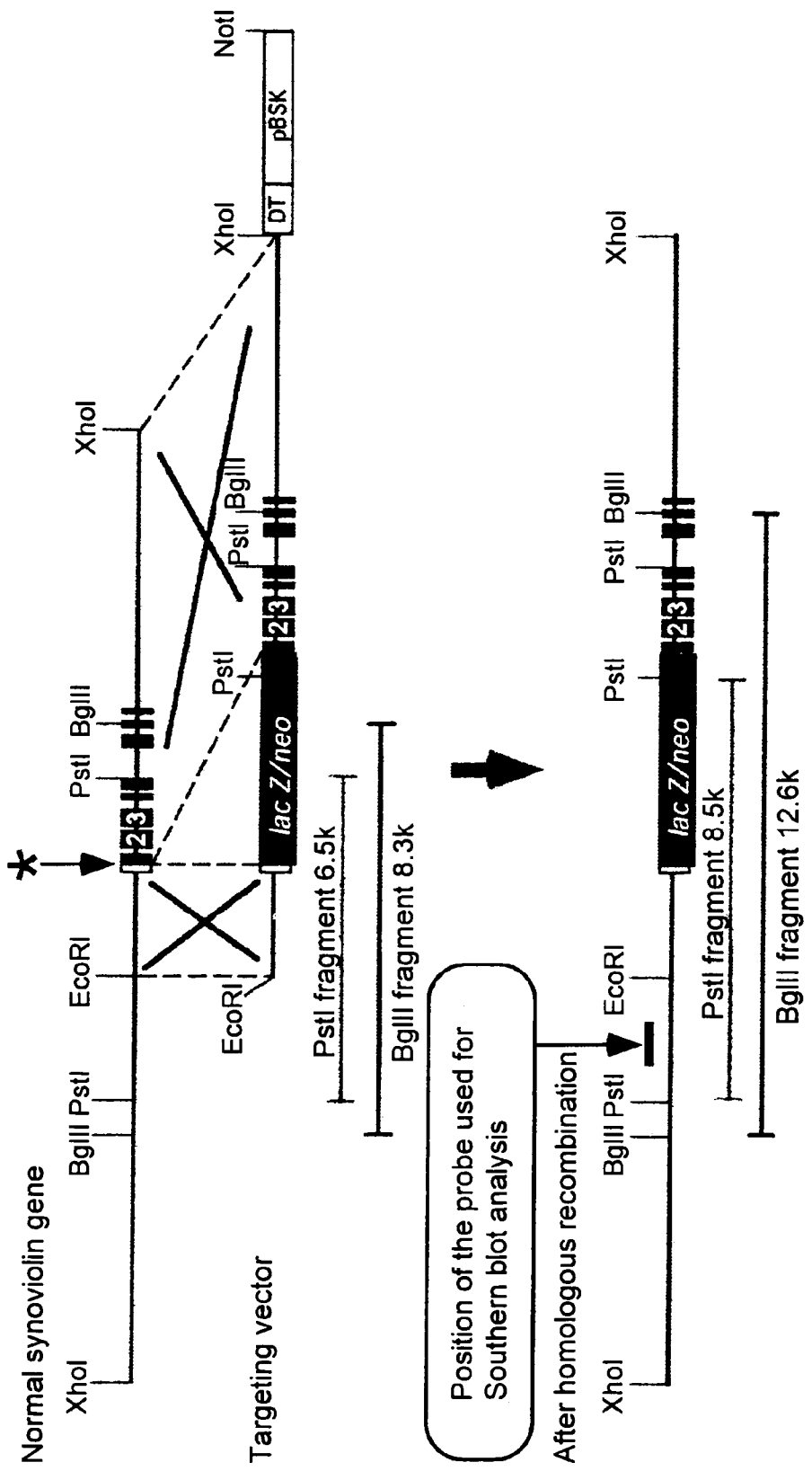
FIG. 19 indicates diagrams showing the structure of a targeting vector to make the synoviolin gene deficient. The lacZ gene is introduced at the translation starting position (ATG codon that is translated into the first methionine; indicated by "*") of the mouse synoviolin gene fragment, and a neomycin resistance (neo) gene is introduced as a positive selection marker gene. In addition, the diphtheria toxin A (DT-A) gene is also linked to form a negative selection marker. Individuals in which homologous recombination occurred lack the expression of the synoviolin gene, but instead, β-galactosidase is expressed and the expression from the promoter of the synoviolin gene can be detected by LacZ staining utilizing its enzyme activity (see FIG. 22). The position of the probe used for Southern blot analysis (see FIG. 20) in order to confirm the genotype is also illustrated.

The lacZ gene was inserted in the translation starting position of the mouse synoviolin gene fragment (ATG codon that is translated into the first methionine) to construct a targeting vector. As the marker gene, a neomycin resistance (neo) gene was inserted and the diphtheria toxin A (DT-A) gene was also linked to be able to exclude cell lines wherein non-homologous recombination occurs (FIG. 19).

This targeting vector was transferred into a mouse ES cell TT-2 by electroporation, and cell lines in which homologous recombination occurred were selected. The cells thus obtained were injected into a mouse blastocyst or eight-cell stage embryo and either directly transplanted to the fallopian tubes of a surrogate mother or transplanted to the uterus of a surrogate mother after being cultured for one day to develop into a blastocyst. Thereafter, a knock-out mouse was prepared by the same method as in the preparation of a transgenic animal. The heterozygously mutated mice (F1) thus obtained were bred to each other to obtain heterozygously and homozygously mutated mice. In the mutated mice thus obtained, the LacZ protein (β-galactosidase) is expressed instead of Synoviolin in tissues where Synoviolin should be expressed.

Figure 20:
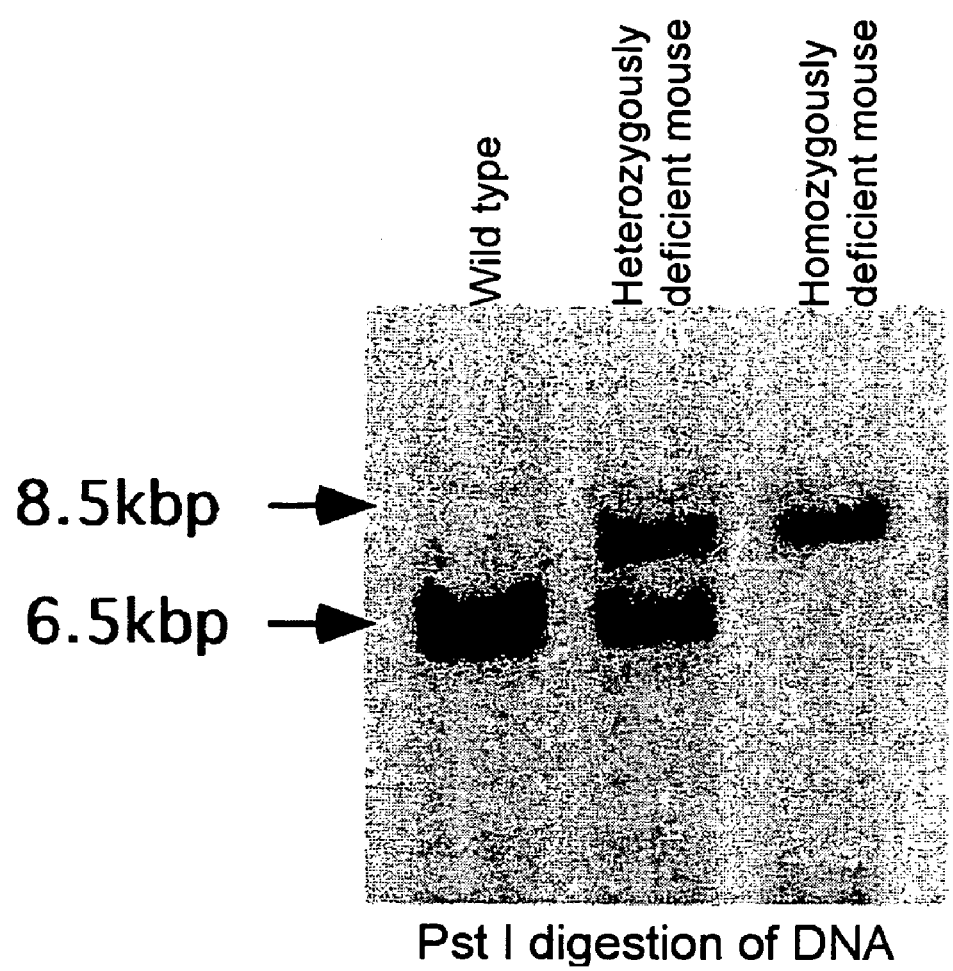
FIG. 20 indicates a photograph showing the results of analysis of the genotype of a synoviolin gene-deficient mouse. DNA is extracted from tails of about two-week old mouse (wild type and hetero-deficient mouse) and from a 14.5 days post conception (dpc) fetus (homozygously-deficient mouse), and after digestion with PstI, Southern blotting was performed using the probe shown in FIG. 19.

The genotype was confirmed by Southern blot analysis. Regarding the wild type mice (14 individuals) and synoviolin heterozygously knock-out mice (32 individuals), DNA was extracted from a point roughly 3 mm from the tip of the tail of the mouse at age of about 2 weeks after birth. With the synoviolin homozygously knock-out mice, samples were taken under a stereomicroscope from the tail and upper and lower limbs of 14.5 days post conception mice, and DNA was extracted. The DNA thus obtained was subjected to digestion of the DNA with the restriction enzyme PstI and was used. The results of analysis are shown in FIG. 20. Bands were detected at 6.5 kbp in the wild type, at 8.5 kbp in the homozygously mutated mice, and at both positions in the heterozygously mutated mice.

Figure 21:
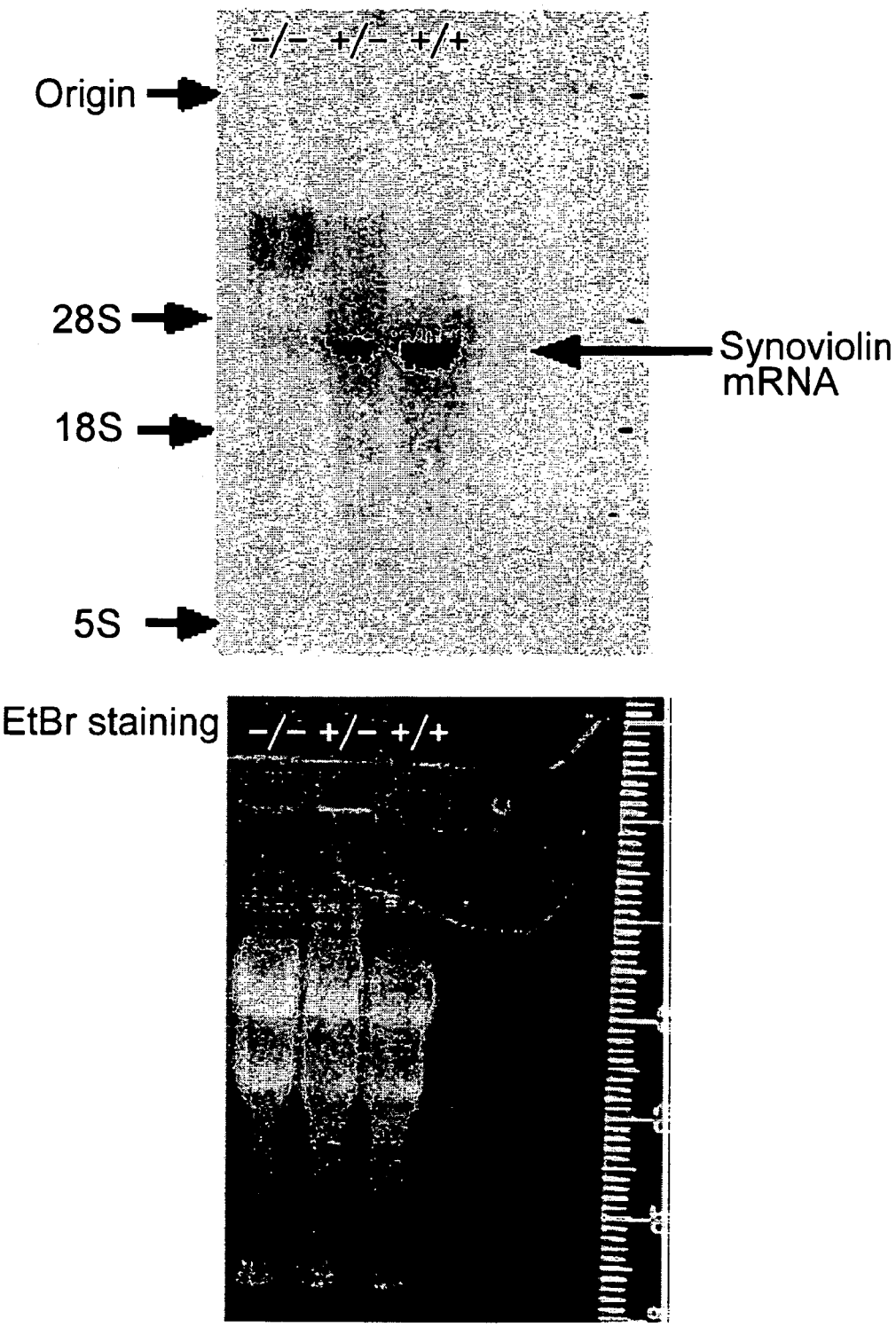
FIG. 21 indicates photographs showing the results of the Northern blot analysis of a synoviolin gene-deficient mouse. mRNA was extracted from a wild type (+/+), synoviolin gene heterozygously knock-out mouse (+/−) and homozygously knock-out mouse (−/−), and Northern blotting was performed using a synoviolin gene fragment as a probe (upper panel). The lower panel illustrates EtBr staining of an agarose gel.

The expression of the synoviolin gene was confirmed by Northern blotting. mRNA was extracted from wild type, heterozygously knock-out mouse and homozygously knock-out mouse individuals (whole embryo at 12.5 days post conception), and electrophoresis was performed with 20 µg in each lane of 1.2% agarose gel. As a result, synoviolin mRNA was not detected in homozygously knock-out mouse (−/−) individuals, while the expression of mRNA in heterozygously knock-out mouse (+/−) individuals was observed to be weaker than that of wild type (+/+) individuals (FIG. 21).

EXAMPLE 18

Study of Synoviolin Expression Sites

The present inventors used LacZ staining to study the Synoviolin expression sites in the mutated mouse individuals obtained in Example 17. To wit, 5-bromo-4-chloro-3-indolyl-β-D-galactoside (X-Gal) was used to color the entire embryo and examine the distribution of expression of LacZ (as β-galactosidase activity). The number of embryos observed was 32.

Figure 22:
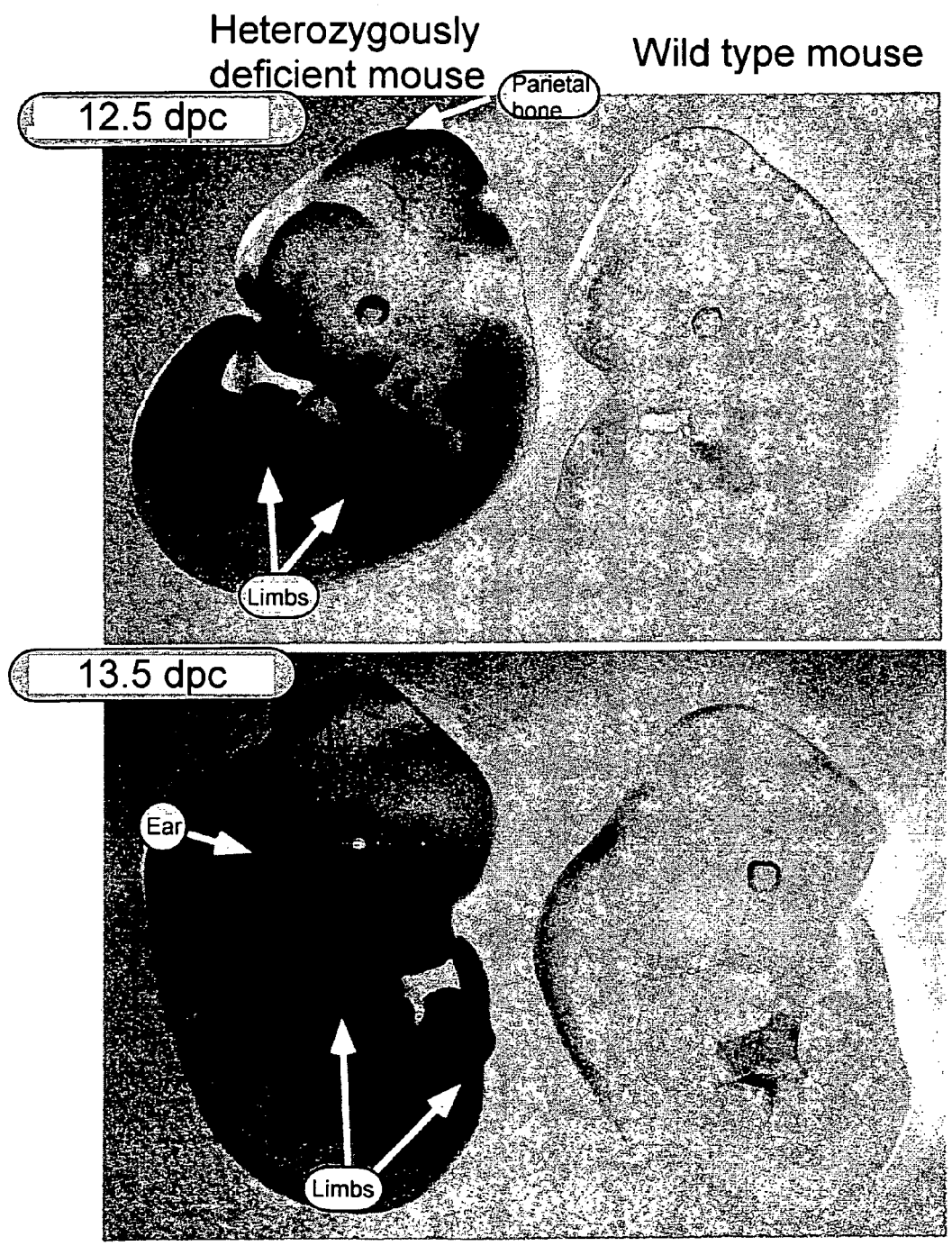
FIG. 22 indicates photographs showing the results of studying the Synoviolin expression location by LacZ staining. The 12.5 days post conception and 13.5 days post conception wild type and heterozygously-deficient mice were stained using LacZ. The expression of Synoviolin in the embryonic stage was found to be strong in the parietal bone, limbs, ears and other locations where bone and cartilage form.
Figure 23:
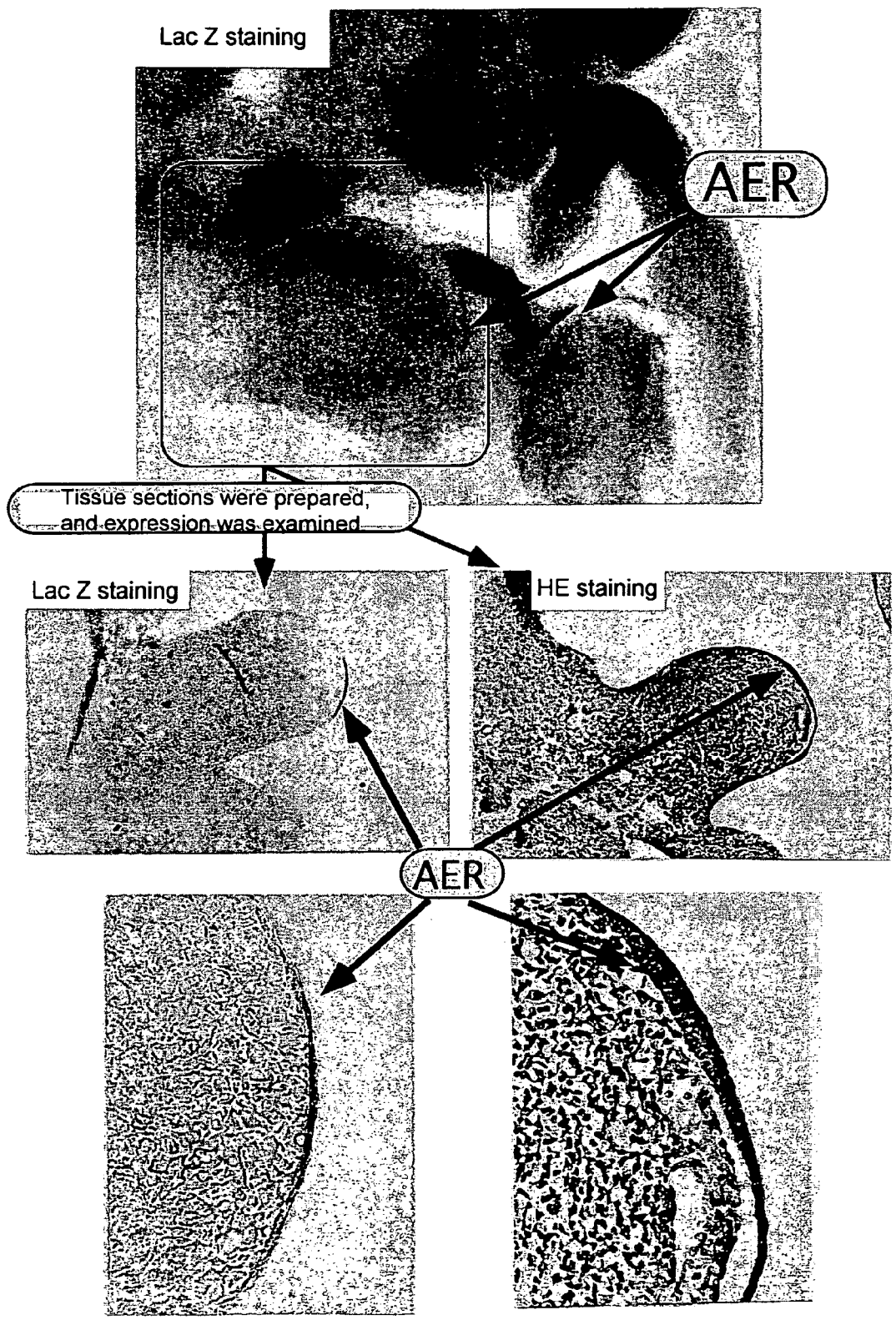
FIG. 23 indicates photographs showing the expression of Synoviolin in the limb-formation stage. The expression of Synoviolin in the limb-formation stage was found to be strong in the apical ectodermal ridge (AER) in the same manner as the expression of FGF4, BMP2 and BMP4.

As a result, strong expression of LacZ was found in the parietal bone and limbs at 12.5 days post conception, and in the ears and limbs at 13.5 days post conception (FIG. 22). All of these were sites where bone or cartilage is formed. Moreover, as a result of performing LacZ staining and HE staining of limb tissue sections during the limb formation stage, strong expression was observed in the apical ectodermal ridge (AER) and the anlage of cartilage and bone (or cartilage and bone) (FIG. 23).

Figure 24:
FIG. 24 indicates photographs showing the LacZ staining of a frozen section of a 13 days post conception limb bud of a heterozygously-deficient mouse. Staining was performed for 4 hours. The blue of LacZ deeply stains undifferentiated mesenchymal cells (anlage of bone and cartilage). Original magnification: ×40.
Figure 25:
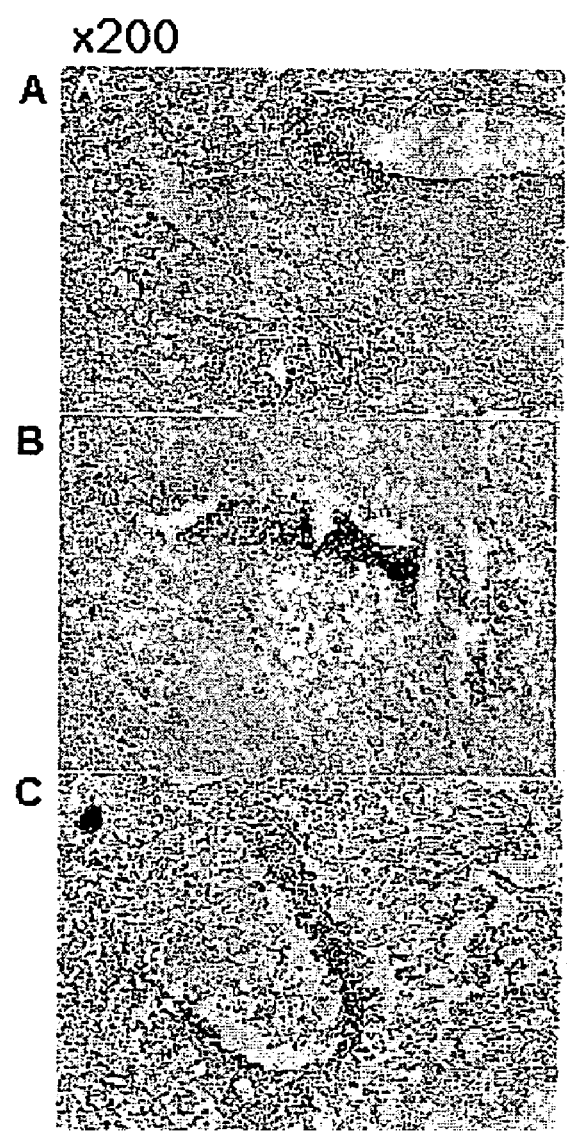
FIG. 25 indicates photographs showing the LacZ staining of a frozen section of a 13 days post conception limb bud of a heterozygously-deficient mouse. Staining was performed for 4 hours. The blue of LacZ deeply stains undifferentiated mesenchymal cells (anlage of bone and cartilage). Original magnification: ×200. A, B and C correspond to FIG. 24.

Moreover, 13-day post conception limb buds were excised and frozen sections were prepared. Then, hematoxylin eosin (HE) or LacZ staining was performed. Specifically, the frozen sections were washed three times for 5 minutes in PBS (−), and glass slides carrying the sections were soaked in X-gal staining solution [X-gal (20 mg/ml) 1.25 ml, HEPES (1M) 2.2 ml, potassium ferricyanide solution (100 mM) 1.5 ml, NaCl (5M) 150 μL, MgCl$_2$ (1M) 65 μl, 10×PBS(−) 5 ml to which milli-Q water (Millipore) was added to reach 50 ml], thereby starting the reaction at 37° C. After staining, dehydration was performed by an ethanol series and xylene and sealing was performed. As a result, the staining of the LacZ blue color was deep in the undifferentiated mesenchymal cells (the anlage of bone and cartilage) (FIGS. 24 and 25).

EXAMPLE 19

Study of Phenotypes

Moreover, the present inventors studied the phenotypes of the synoviolin gene knock-out mouse.

Figure 26:
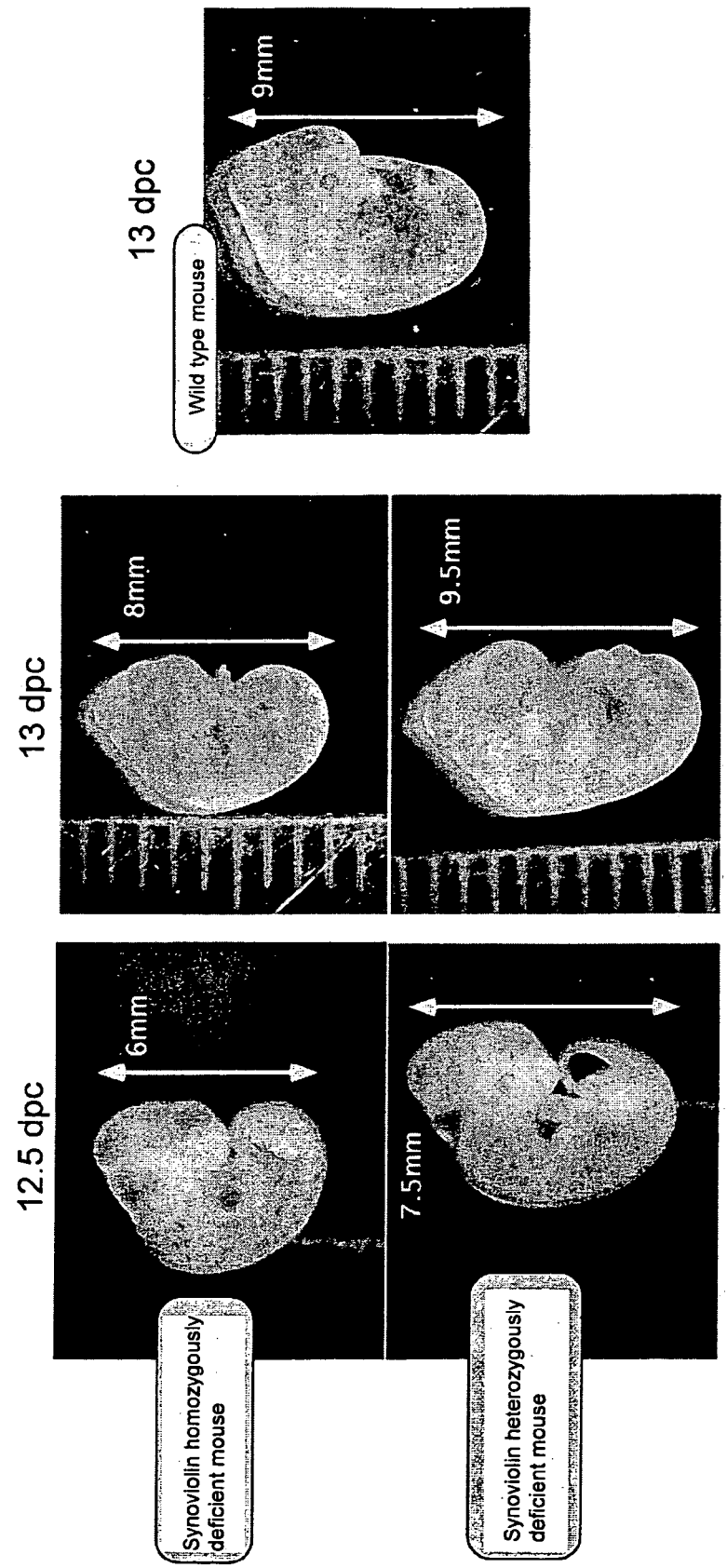
FIG. 26 indicates photographs showing the phenotype of synoviolin gene homozygously-deficient mice at 12.5 days and 13 days post conception. The synoviolin gene homozygously-deficient mice at 12.5 days and 13 days post conception exhibited a trend of a short length from the parietal region to the buttocks, and a trend for the formation of the skull and limbs to be premature. No marked differences in the phenotype were found between the 13 days post conception heterozygously-deficient mouse and wild type mouse.

At 12.5 days post conception, the homozygotes exhibited a trend of a shorter length from the parietal region to the buttocks than that of the heterozygotes, and a trend for the formation of the skull and limbs to be premature, but at 13 days post conception, there was no marked difference in the phenotype between the heterozygotes and wild types (FIG. 26). Besides, no births of homozygous mouse individuals were found, and no live homozygous mouse embryos were found after at least 17 days post conception. Accordingly, these were thought to be fetal deaths (Table 1).

TABLE 1

| Age | Number analyzed | Wild type | Heterozygote | Homozygote (alive or dead) |
|---|---|---|---|---|
| 12.5 dpc | 10 | 0 | 8 | 2 (alive) |
| 13 dpc | 10 | 2 | 7 | 1 (alive) |
| 14.5 dpc | 6 | 2 | 3 | 1 (?) |
| 15.5 dpc | 6 | 0 | 5 | 1 (dead) |
| 4 weeks old | 46 | 14 | 32 | 0 |

Figure 27:
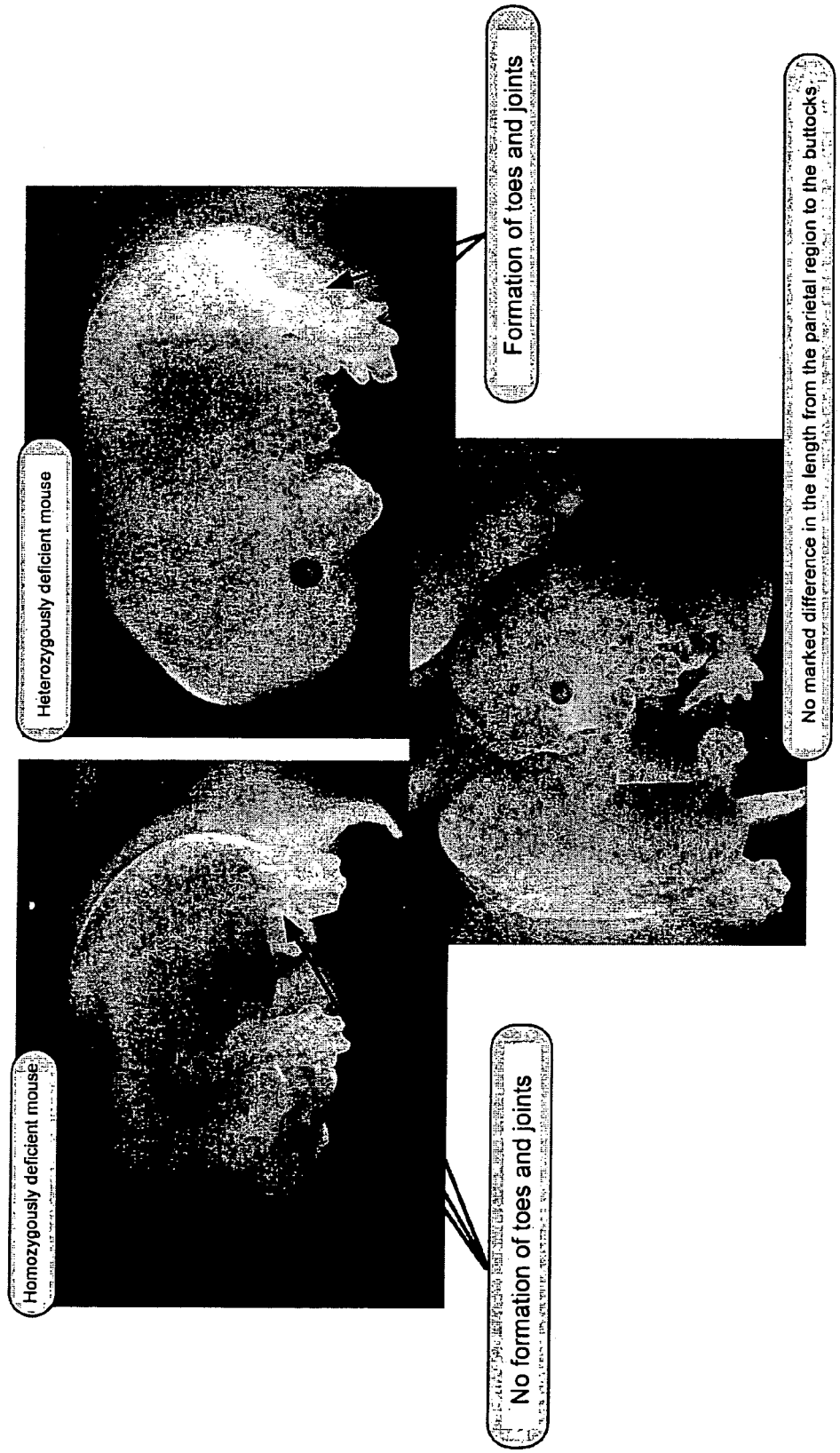
FIG. 27 indicates photographs showing the phenotype of a 14.5 days post conception synoviolin gene-deficient mouse. Limb bud abnormalities were found in a 14.5 days post conception synoviolin gene homozygously-deficient mouse.

At 14.5 days post conception, no marked difference was observed between heterozygotes and homozygotes in the length from the parietal region to the buttocks. However, while the toes and joints were formed in the heterozygotes, they were not formed in the homozygotes and limb abnormalities were found (FIG. 27).

Figure 28:
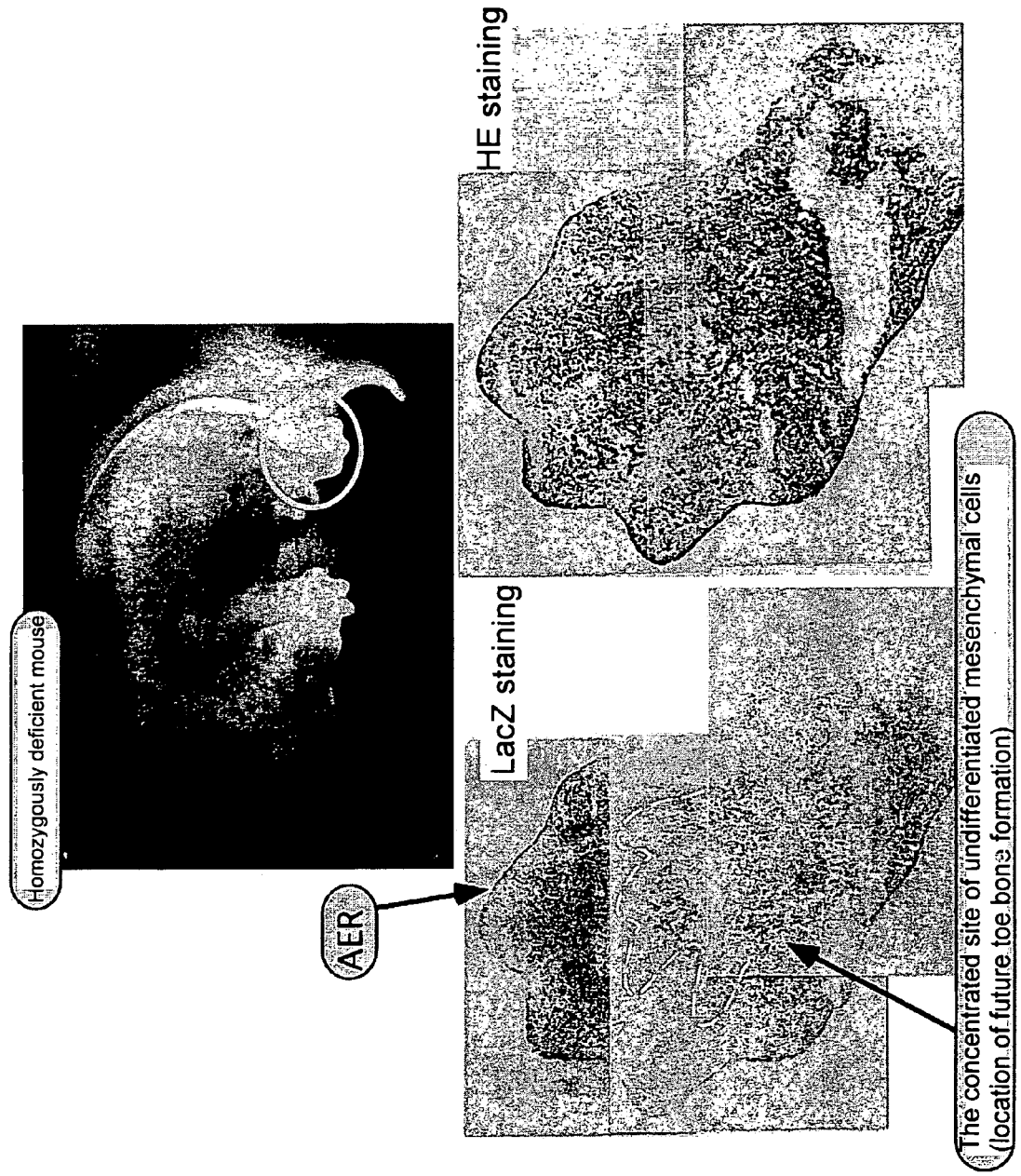
FIG. 28 indicates photographs showing the expression of LacZ in the hind limbs of a 14.5 days post conception synoviolin gene homozygously-deficient mouse (reflecting the expression of Synoviolin). In the abnormal hind limbs of a homozygously-deficient mouse, LacZ was found to be expressed in sites where the AER and undifferentiated mesenchymal cells are concentrated.

Moreover, as a result of performing LacZ and HE staining on the hind limbs that exhibited abnormalities in the homozygotes, the expression of LacZ which reflects the expression of Synoviolin was found in the concentrated sites of the AER and undifferentiated mesenchymal cells (locations of future toe bone formation) (FIG. 28).

Figure 29:
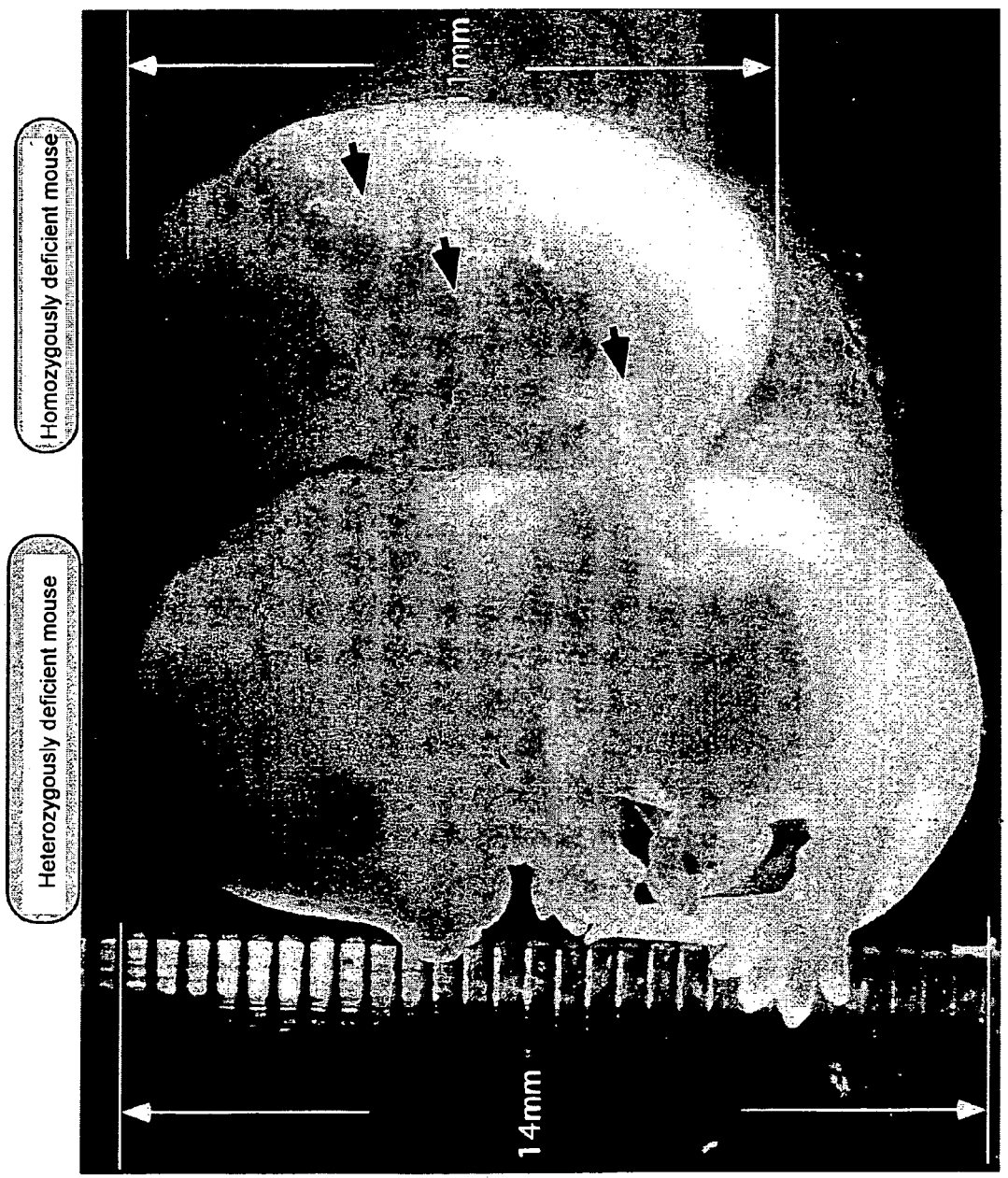
FIG. 29 indicates a photograph showing the phenotype of a 15.5 days post conception synoviolin gene-deficient mouse. Limb bud abnormalities and abnormal formation in the upper and lower jawbones and ears were found in a homozygously-deficient mouse. No heartbeat was found and it was not alive.
Figure 30:
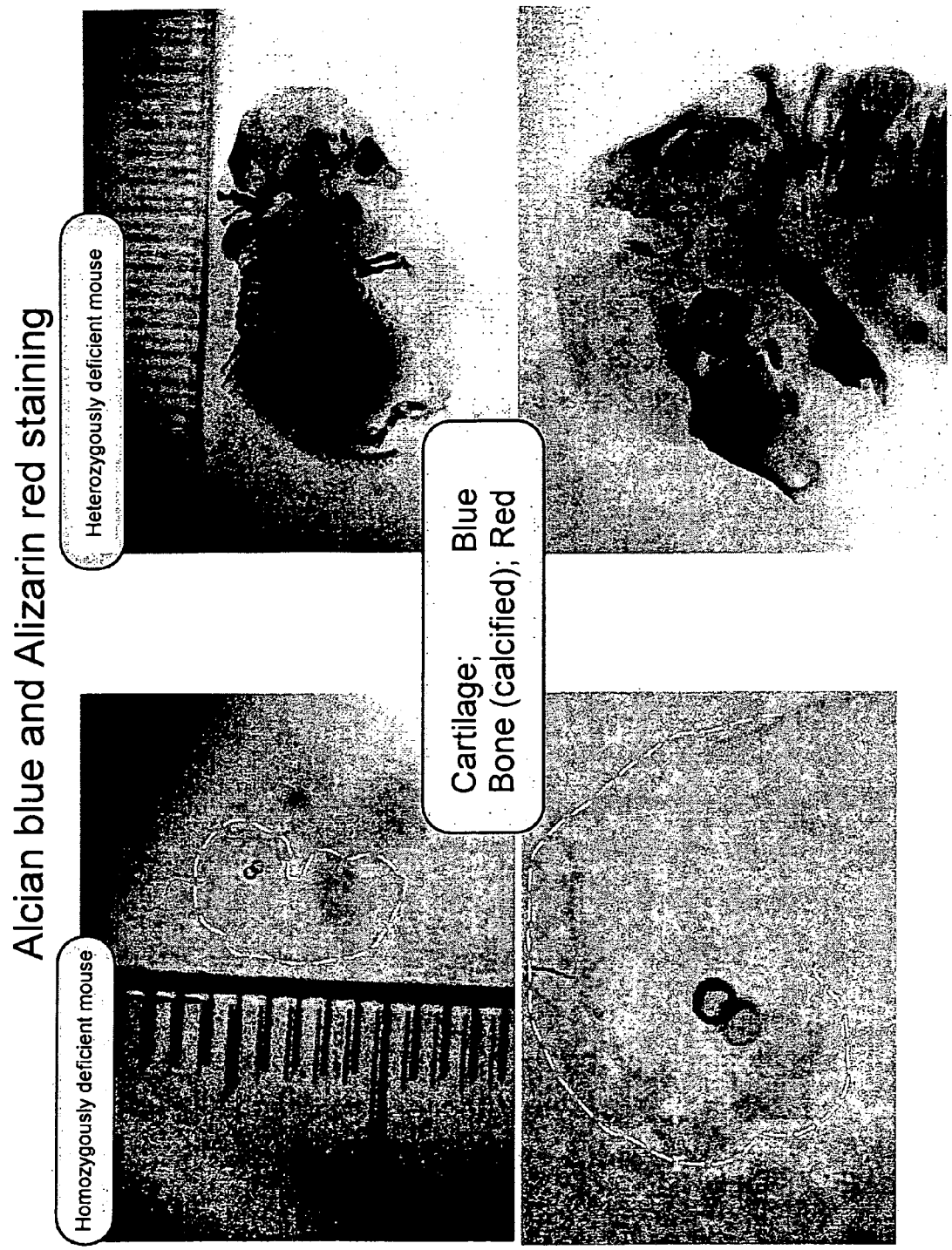
FIG. 30 indicates photographs showing the skeleton of a 15.5 days post conception synoviolin gene-deficient mouse. Alcian blue and Alizarin red staining are shown. Cartilage stained by Alcian blue and calcified bone stained by Alizarin red were not found in the synoviolin homozygously-deficient mouse.

At 15.5 days post conception, the homozygotes were dead, exhibiting morphological abnormalities in the limb buds, upper and lower jaws and ears (FIG. 29). Moreover, cartilaginous tissue was stained by Alcian blue and bone (calcified) tissue was stained by Alizarin red. To wit, the epidermis, dermis and contents of a mouse were removed, soaked in fixer (ethanol:hydrogen peroxide=9:1), dehydrated in an alcohol series, and then stained with Alizarin red and Alcian blue, and the tissue was made transparent with an alkaline solution. After made transparent, it was kept in a glycerin solution and staining was observed. As a result, no formation of cartilaginous tissue (stained blue) or bone (calcified) tissue (stained red) was found in the homozygote (FIG. 30).

From the aforementioned results, the synoviolin gene homozygously knock-out mouse was found to exhibit developmental abnormalities in its limb buds in the fetal stage. In addition, the formation of cartilage and bone was not found, and Synoviolin was found to be expressed in the locations of development of the limb buds, cartilage and bone. Accordingly, the contribution of the Synoviolin molecule to skeletal formation is strongly conceivable.

EXAMPLE 20

Figure 31:
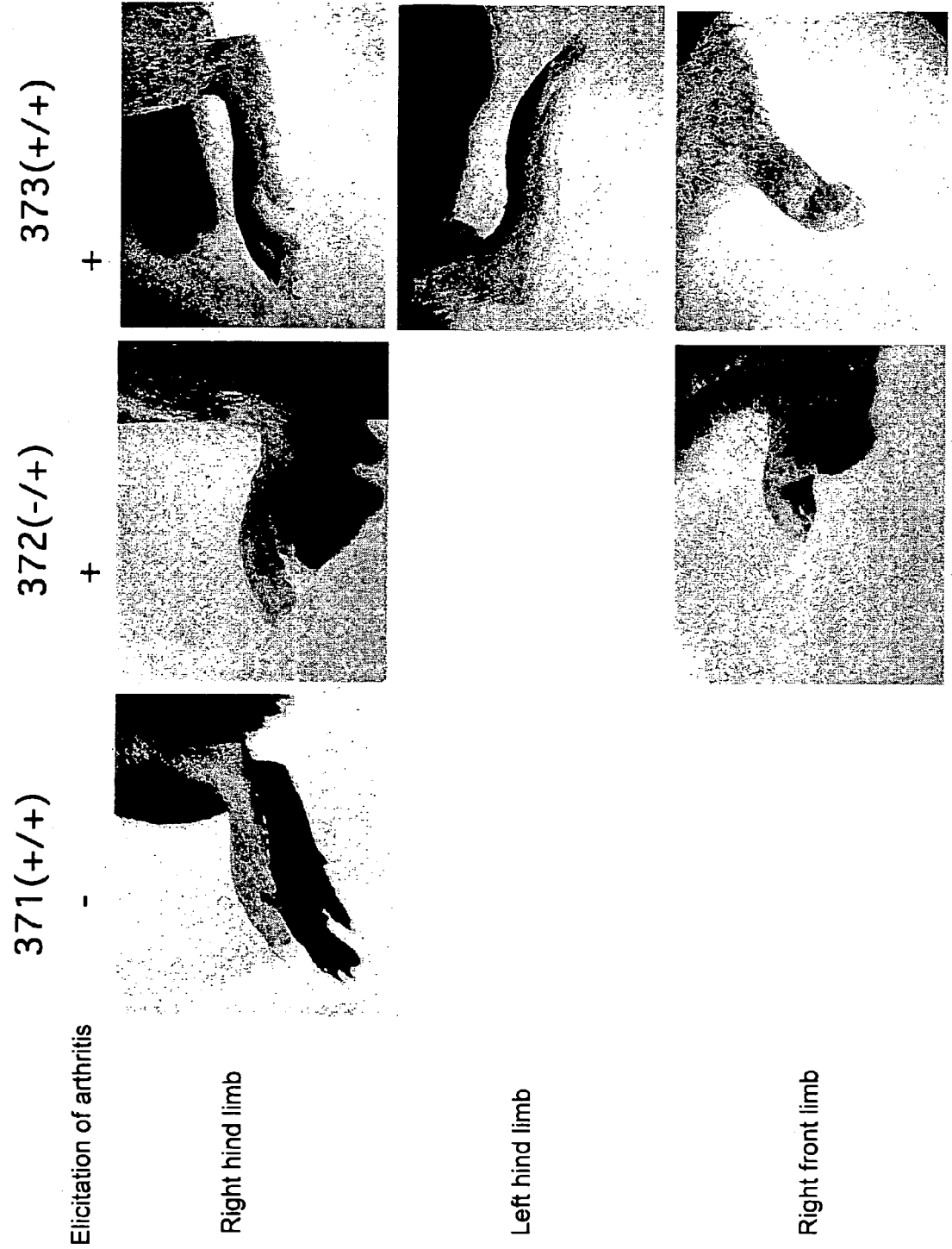
FIG. 31 indicates photographs showing a mouse arthritis model using an anti-collagen antibody cocktail in a synoviolin knock-out mouse. To the wild type mouse [373 (+/+)] and synoviolin heterozygously knock-out mouse [372 (−/+)], the anti-collagen antibody cocktail was administered to elicit arthritis (+ in the figure). The non-administered wild type mouse (−) was also observed [371 (+/+)]. As a result, swelling and reddening of joints in both the front limbs and hind limbs were lesser in the synoviolin heterozygously knock-out mouse than in the wild type. To wit, the occurrence of arthritis was found to be weaker in the synoviolin heterozygously knock-out mouse than the arthritis elicited in the wild type mouse.
Figure 32:
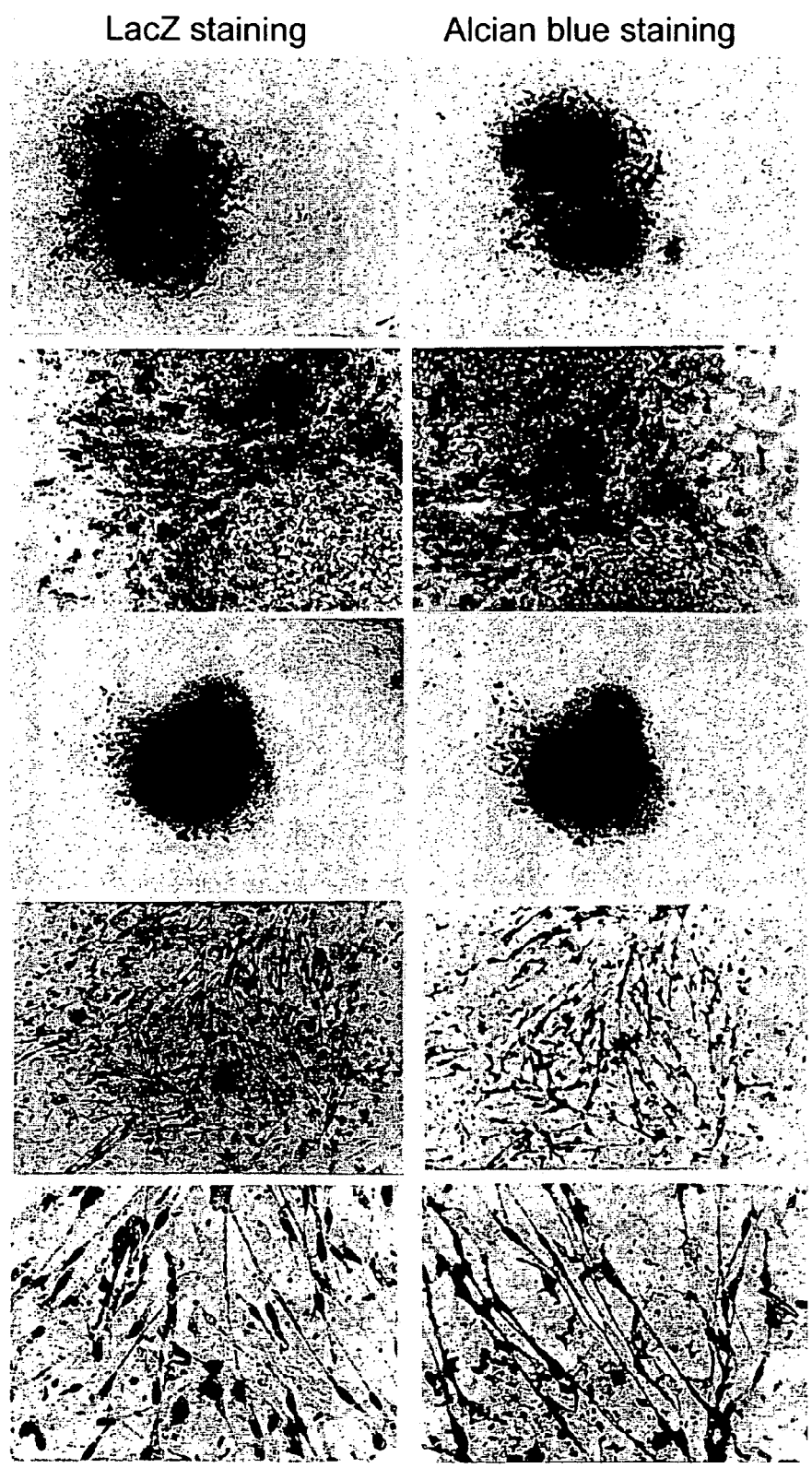
FIG. 32 indicates photographs showing the LacZ staining and Alcian blue staining of primary cultured cells obtained from the limb buds of a synoviolin gene homozygously-deficient mouse (13 dpc fetus). The LacZ positive colony (to wit, the Synoviolin expressing cells) agreed with the Alcian blue stain positive colony. This result suggests that Synoviolin contributes to bone and cartilage differentiation. Passage number 1 (p1).
Figure 33:
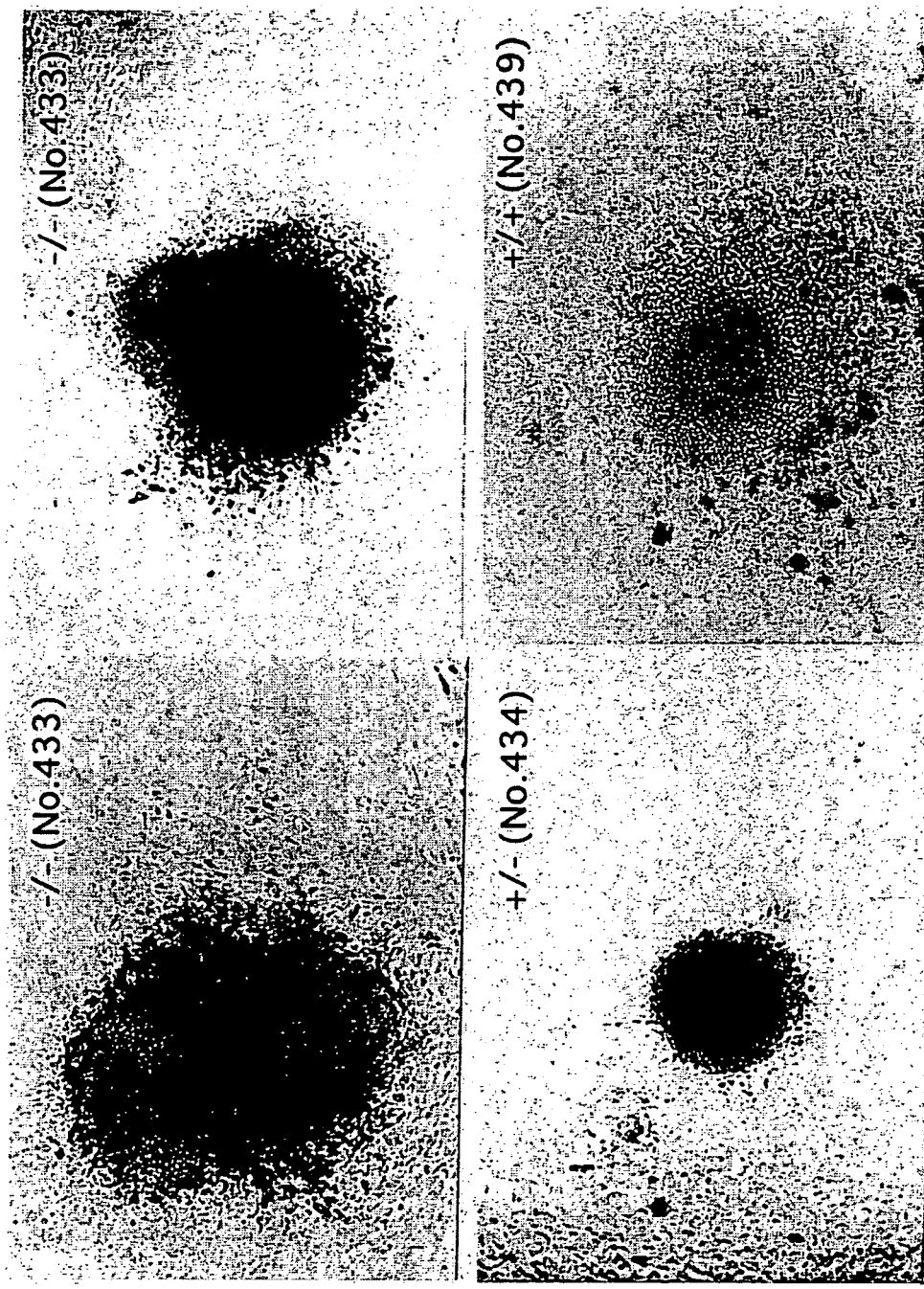
FIG. 33 indicates photographs showing LacZ staining of a primary cultured cell obtained from the limb bud of a 13 dpc mouse fetus. Cells derived from a wild type mouse (+/+), and synoviolin gene heterozygously (−/+) and homozygously (−/−) deficient mice are shown. The expression of LacZ is observed only in the synoviolin gene-deficient mouse (knock-in of the lacZ gene). Passage number 1 (p1).
Figure 34:
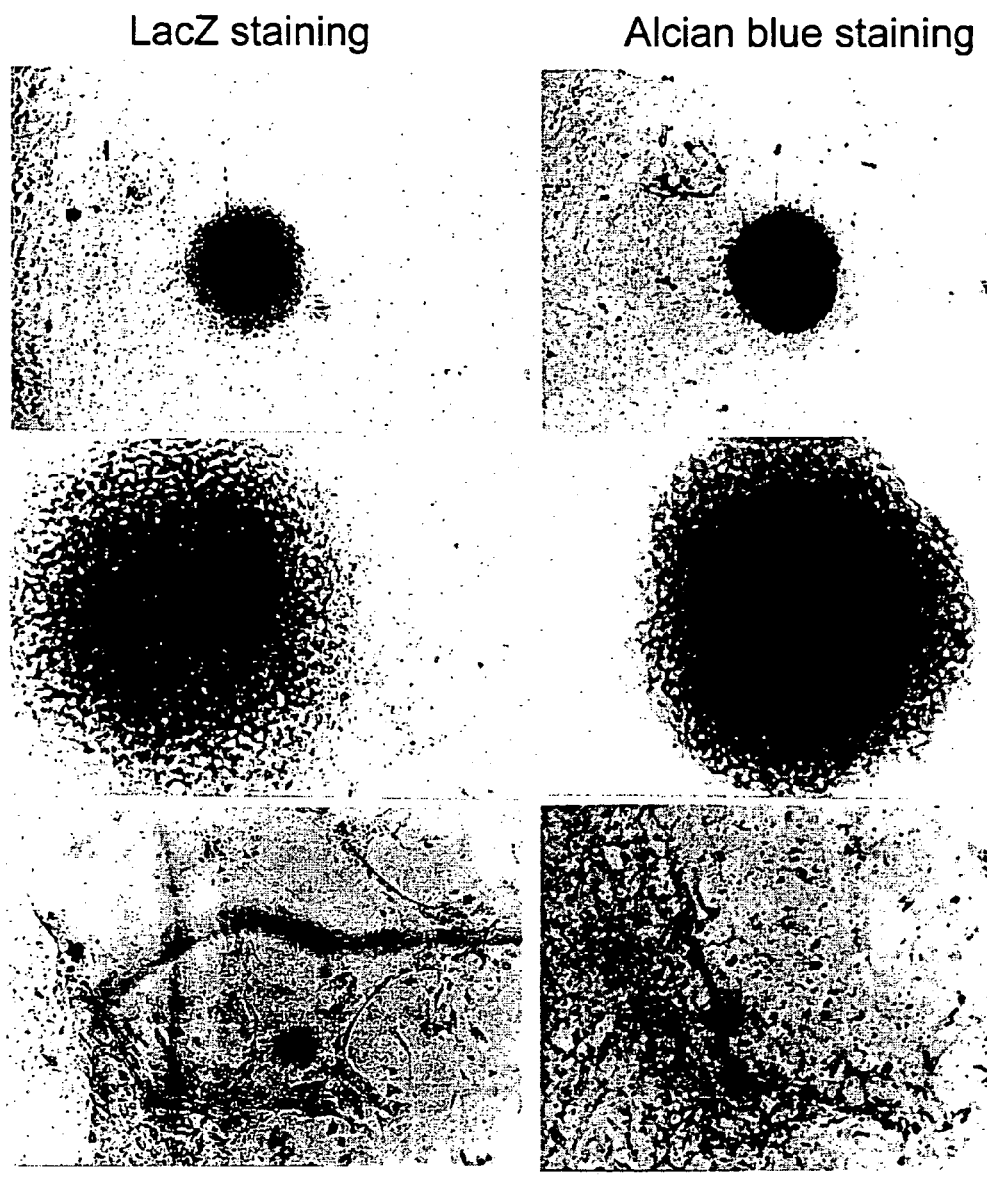
FIG. 34 indicates photographs showing the LacZ staining and Alcian blue staining of primary cultured cells obtained from the limb buds of a synoviolin gene heterozygously-deficient mouse (13 dpc fetus). The LacZ positive colony (to wit, the Synoviolin expressing cells) agreed with the Alcian blue stain positive colony. Passage number 1 (p1).
Figure 35:
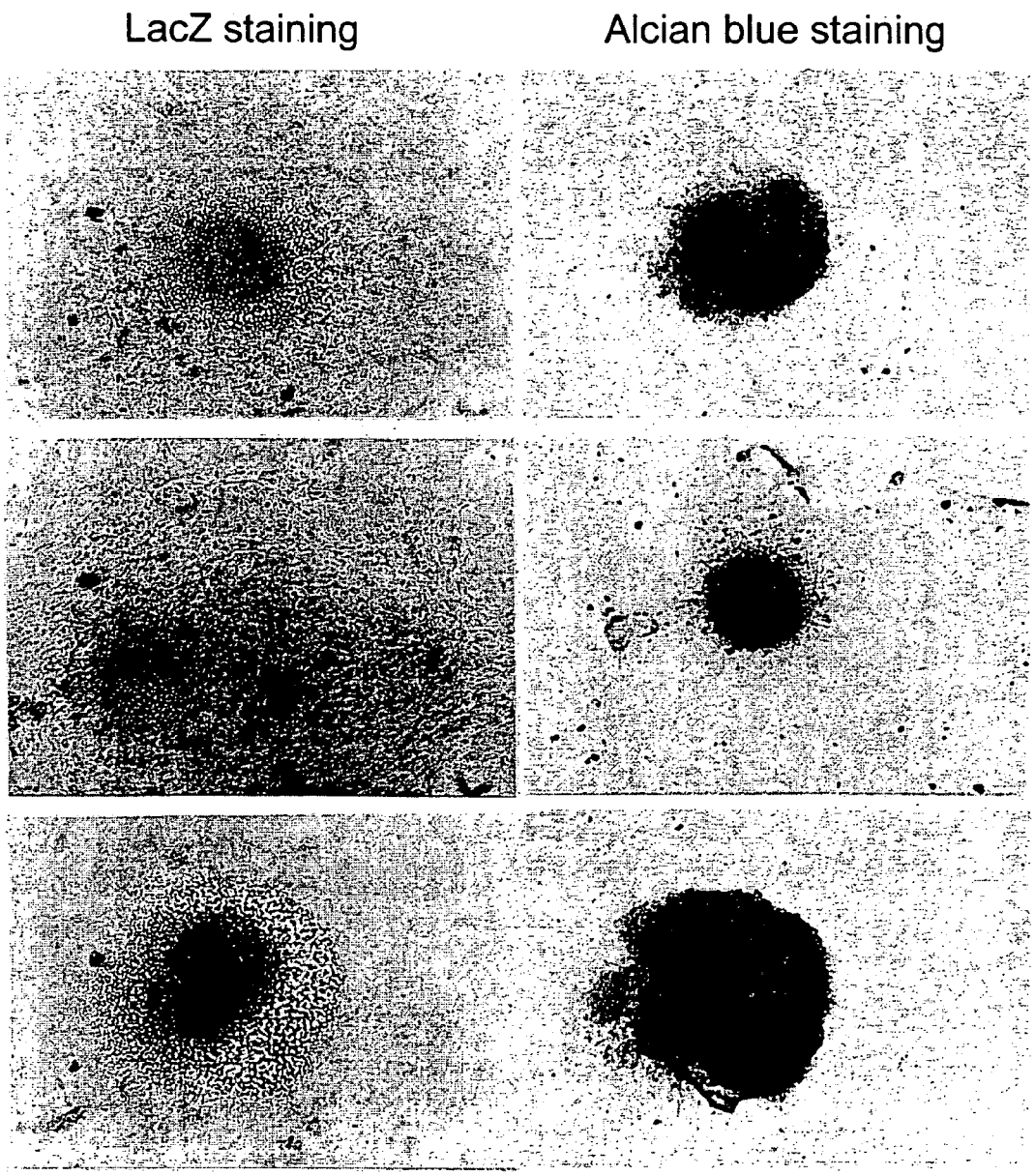
FIG. 35 indicates photographs showing the LacZ staining and Alcian blue staining of primary cultured cells obtained from the limb buds of a wild type mouse (13 dpc fetus). Staining by LacZ is not observed. Passage number 1 (p1).
Figure 36:
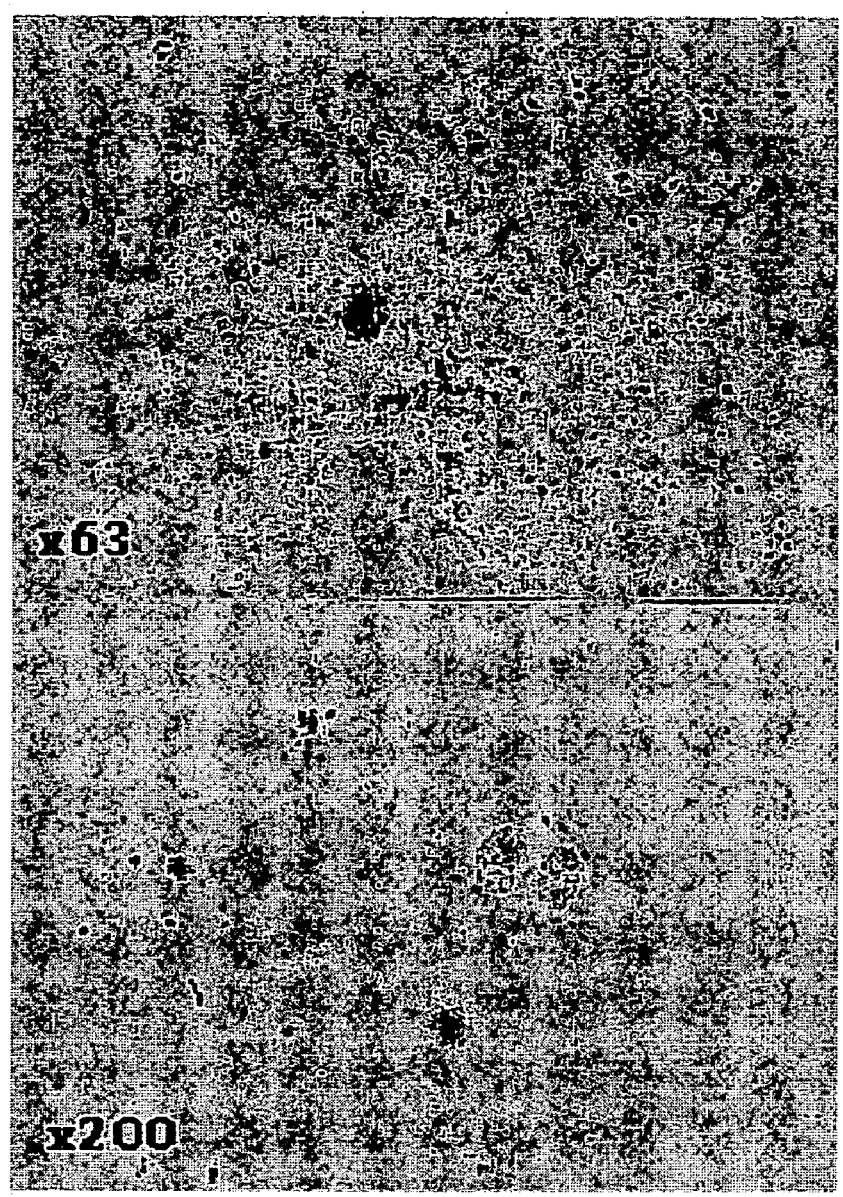
FIG. 36 indicates a photograph showing the LacZ staining of primary cultured cells obtained from the limb buds of a synoviolin gene heterozygously-deficient mouse (13 dpc fetus). LacZ staining (expression of Synoviolin) is confirmed even in the typical binucleate cartilaginous cells (see the 200× image).
Figure 37:
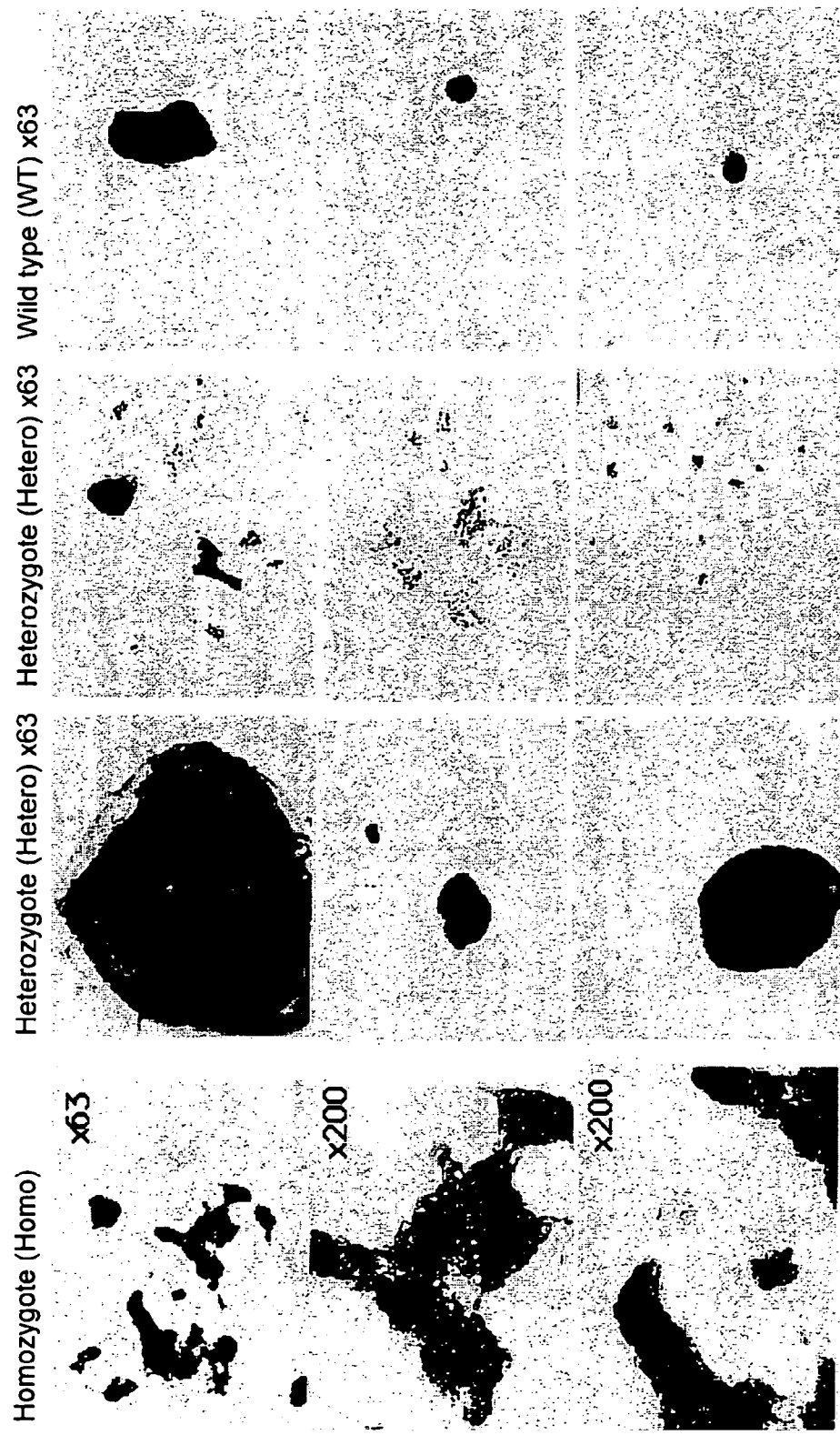
FIG. 37 indicates photographs showing the von Kossa staining of primary cultured cells obtained from the limb buds of fetal mice. Cells derived from wild type (WT), synoviolin gene heterozygously (Hetero) and homozygously (Homo) deficient mice are shown. A decrease in bone formation capacity is observed in the synoviolin gene-deficient mouse (Homo). Passage number 1 (p1).
Figure 38:
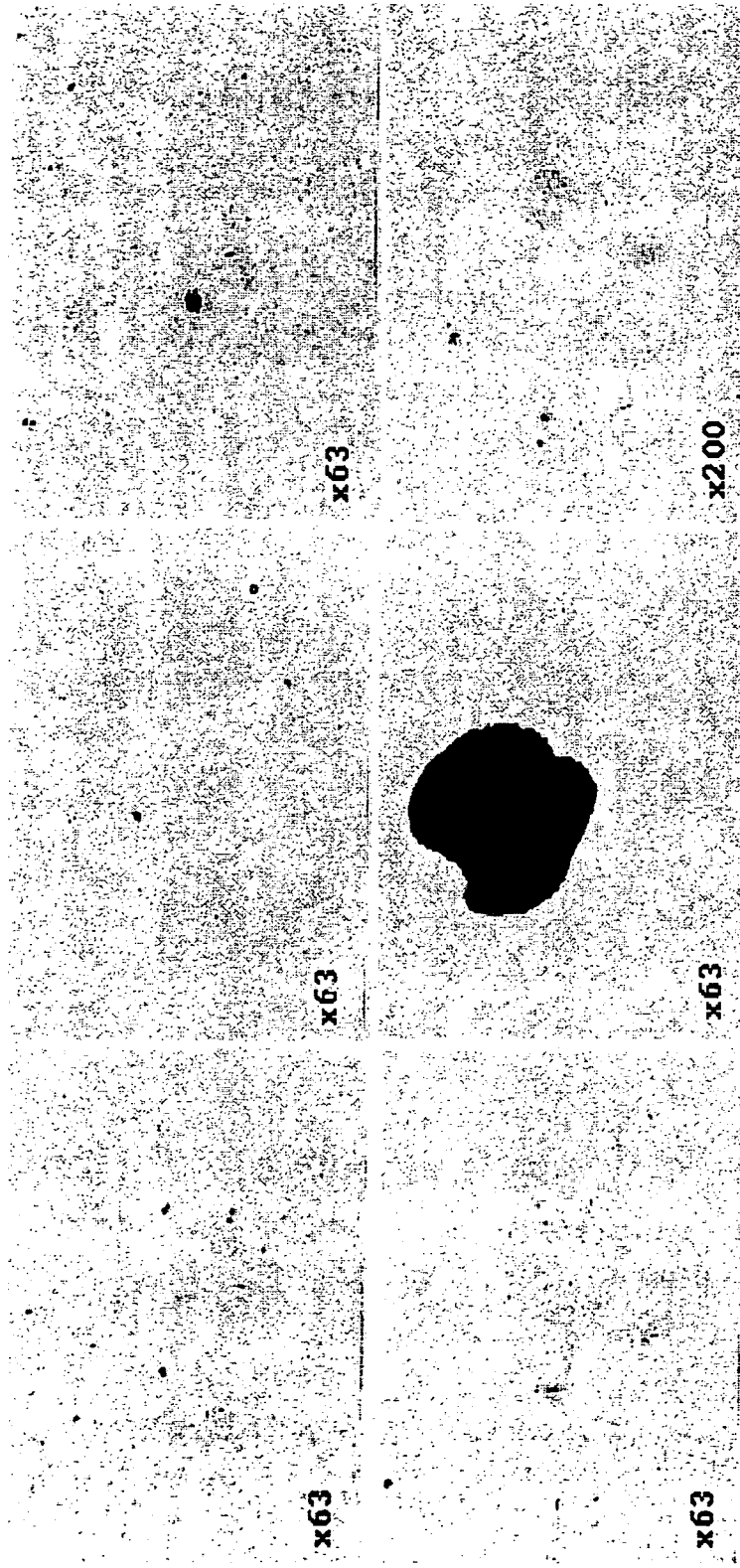
FIG. 38 indicates photographs showing the LacZ staining of primary cultured cells (passage number 3; p3) obtained from the limb buds of a synoviolin gene homozygously-deficient fetal mouse. The culture was continued until it became subconfluent. After LacZ staining was performed (overnight), hematoxylin eosin (HE) staining was performed.

Administration of Cocktail for Arthritis to the Synoviolin Gene Knock-Out Mouse Collagen-induced arthritis (CIA) in the mouse is widely used as an arthritis model for human rheumatoid arthritis. An anti-collagen antibody cocktail was administered to the synoviolin gene knock-out mouse (heterozygote) prepared in Example 17 and to a wild-type mouse, and the arthritis elicited was observed. As a result, the elicitation of arthritis in the synoviolin heterozygously knock-out mouse was found to be weaker that that of the wild type (FIG. 31). These results also support the fact that Synoviolin contributes to the induction of arthritis in RA.

EXAMPLE 21

Analysis of a Primary Culture of Fetal Limb Bud Cells of a Synoviolin Gene Knock-Out Mouse Among the cells obtained (by the explant method) from a knock-out (KO) mouse, LacZ staining, namely the expression of Synoviolin, was found only in the undifferentiated mesenchymal cells thought to be the anlage of cartilage, bone and limbs. In addition, in the primary culture of fetal limb bud cells, the LacZ positive colony (to wit, the Synoviolin expressing cells) agreed with the Alcian blue stain-positive colony, and moreover, the staining of LacZ (as β-galactosidase activity) (expression of Synoviolin) is observed in the typical binucleate cartilaginous cells also. This supports the fact that Synoviolin is involved in bone and cartilage differentiation. Moreover, by alkaline phosphatase staining, von Kossa staining or other methods, it was confirmed that the capacity to form bone and cartilage was delayed in homozygously knock-out derived cells (FIGS. 32-38).

In van Kossa staining, after the cells were washed, the solution was substituted with silver nitrate solution (5% w/v). After the cells were lightly washed with distilled water, reduction and fixing were performed with sodium thiosulfate solution (5% w/v). After washing, counterstaining was performed with Kernechtrot solution (0.1% w/v Kernechtrot (Nuclear Fast Red), 5% w/v aluminum sulfate) (Masaji Seki, Soshiki Kensa Hō—Soshiki Kōzō to Kyokusho Kagaku—[Tissue Test Methods: Tissue Structure and Local Chemistry], 257-258, Kyorin-Shoin, 1961; L. Lison, Tadashi Imaizumi, trans., *Histochimie et Cytochimie Animales: Principes et Mëthodes* [Animal Histochemistry and Cytochemistry: Principles and Methods], 625-636, Hakusuisha Publishing Co. Ltd., 1962; Yutaka Sano, *Soshikikagaku Kenkyū Hō—Riron to Jutsushiki* [Histochemistry Research Methods: Theory and Practice], 616-621, Nanzando Co., Ltd., 1965). The detection of alkaline phosphatase activity was performed with an alkaline phosphatase tissue staining kit (Sigma, Diagnostic Kits and Reagents, alkaline phosphatase (AP), leukocyte, Cat. No. 86-R).

EXAMPLE 22

Test Compound Assay Using Synoviolin Gene Knock-Out Mouse-Derived Cells

Primary cultured cells of a synoviolin gene heterozygously knock-out mouse (lacZ gene knock-in) were used to evaluate the effect of a test specimen on the expression of the synoviolin gene by β-gal assay. The primary cultured cells of a synoviolin gene heterozygously knock-out mouse after 3 passages were seeded to 24 well plates at 0, $1\times10^3$, $3\times10^3$, $1\times10^4$, $3\times10^4$ and $1\times10^5$ cells per well, and cultured overnight in Dulbecco's modified Eagle's medium (DMEM) containing 10% fetal calf serum. First, cell lysis solution (Promega) was added to the cell culture in the absence of stimulation in a quantity (100 µl/well) sufficient to cover the cell layers completely. Then, the culture plates were moved to a shaking machine and shaken gently for 15 minutes at room temperature so that the cell layers were always soaked in lysis solution.

Figure 39:
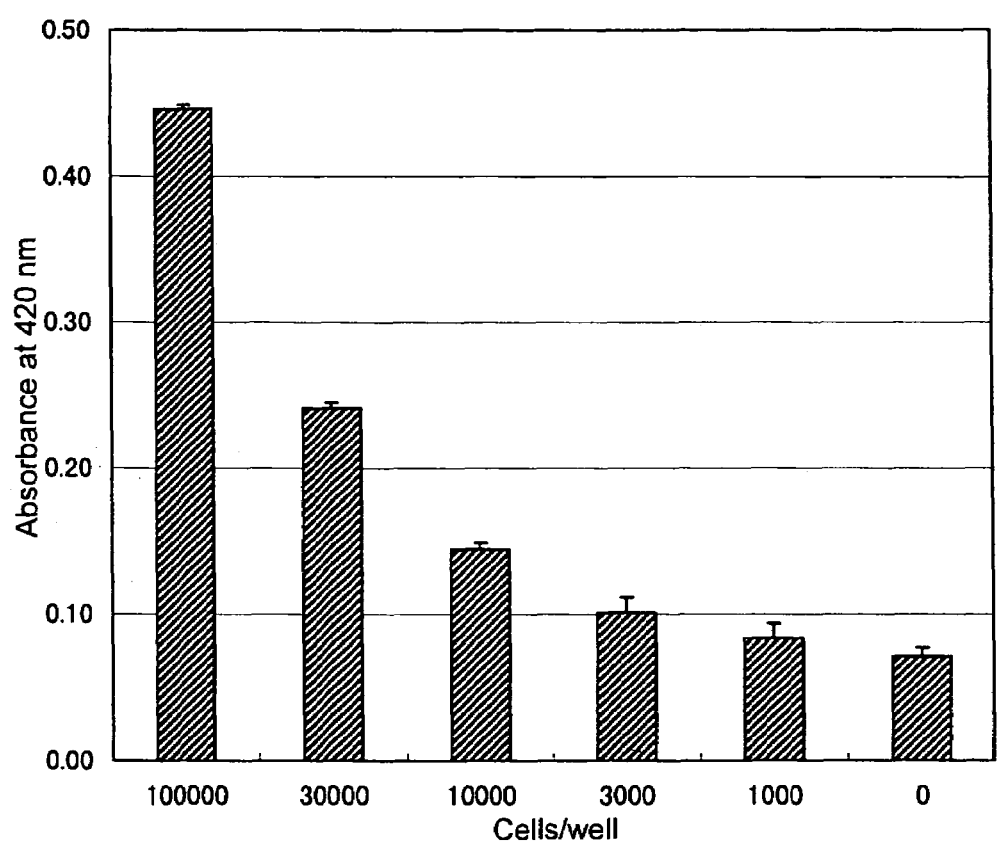
FIG. 39 indicates a diagram showing the results of a β-gal assay of primary cells of a synoviolin gene heterozygously knock-out mouse (lacZ gene knock-in). The specimens were measured in triplicate and the mean and standard deviation are indicated.

The β-galactosidase activity of the cells was measured in the following manner. To 20 µl of the obtained cell extract solution were added 1 µl of Mg solution (0.1M $MgCl_2$, 4.5M β-mercaptoethanol), 22 µl of ONPG solution (o-nitrophenyl-β-D-galactopyranoside) (concentration of 4 mg/ml in a 0.1M phosphate buffer (pH 7.5)), and 57 µl of 0.1M phosphate buffer (pH 7.5), to give a total volume of 100 µl. With care not to allow it to dry, incubation was performed for 6 hours at 37° C. The reaction was halted by adding 150 µl of 1M sodium carbonate solution (prepared by dissolving 21.2 g of $Na_2CO_3$ in $H_2O$, by adjusting to 200 ml and by filtering with a 0.45 µm filter), and the β-galactosidase activity was quantified by measuring the absorbance at 420 nm. The experiment was performed in triplicate. As a result, β-galactosidase activity was detected in the lacZ gene knock-in mouse cells depending on the number of cells (FIG. 39). The present inventors confirmed that the evaluation of promoter activity (β-gal assay) is possible using β-galactosidase activity as an index.

Next, β-gal assay was performed in the same manner by adding various drugs to the primary cultured cells, and then the effects of the various drugs on synoviolin promoter activity were evaluated. As a negative control, the same measurements were performed by adding the culture medium only. The test drugs used were prednisolone (0.01-1 µM) and 12-O-tetradecanoylphorbol 13-acetate (TPA; 0.001-0.1 µM). Prednisolone is a steroidal anti-inflammatory drug, and TPA is a protein kinase C activator.

Figure 40:
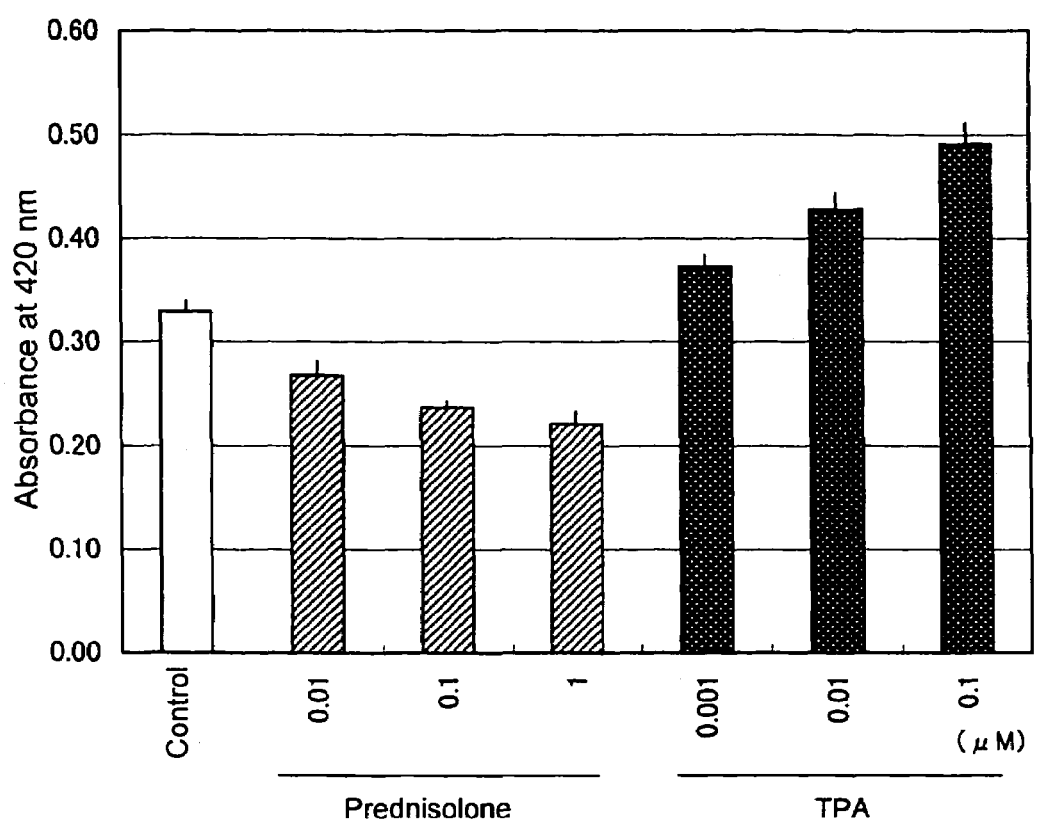
FIG. 40 indicates a diagram showing the results of examining the effects of various drugs on the synoviolin promoter activity by β-gal assay of primary cells of a synoviolin gene heterozygously knock-out mouse (lacZ gene knock-in). The specimens were measured in triplicate and the mean and standard deviation are indicated.

$5\times10^4$ primary culture cells were seeded in each well, and after culturing overnight, the various drugs were added at the aforementioned concentrations. After the drugs were added, the cells were cultured for 72 hours and the β-galactosidase activity of each well was measured to evaluate the promoter activity. As a result, the synoviolin promoter activity was found to be affected by these drugs in a concentration-dependent manner (FIG. 40). To wit, this confirmed that the activity of the drug on the synoviolin promoter could be evaluated with the assay system based on the present invention. From the results above, such an assay can be used to evaluate the effect of various drugs on the synoviolin promoter activity, and thus, it is possible to screen for compounds that promote or suppress the synoviolin promoter activity.

EXAMPLE 23

Preparation of Anti-Synoviolin Monoclonal Antibodies

Monoclonal antibodies to Synoviolin were prepared as follows. As peptides used for immunization, the following three peptides containing partial amino acid sequences of human Synoviolin were synthesized. These amino acid sequences were selected from among the domains assumed to have antigenicity.

Syno-P3 (SLALTGAVVAHAYYC/SEQ ID NO: 3),
Syno-P2 (TCRMDVLRASLPAQS/SEQ ID NO: 4), and
Syno-P1 (GAATTTAAGTSATAC/SEQ ID NO: 5).

Keyhole limpet hemocyanin (KLH) was conjugated to each of the synthesized peptides via Cys within the amino acid sequence. 50 µg of each of the synthesized peptides conjugated to KLH was dissolved in 0.1 ml of physiological saline solution, and 0.1 ml of Freund's complete adjuvant (FCA) was added to prepare an immunogen. Each immunogen (0.2 ml) was injected hypodermically into the back of eight mice (BALB/c female, 5 weeks old), thus immunizing it. Immunization was performed once every two weeks for four times in total, and immunization was performed one more time one week later. Eight days after the final immunization, blood was drawn from the heart to obtain 200 µl or more serum. Spleen cells were taken from individuals in which an increase in the antibody titer was confirmed by ELISA, and then cell fusion was performed.

Figure 41:
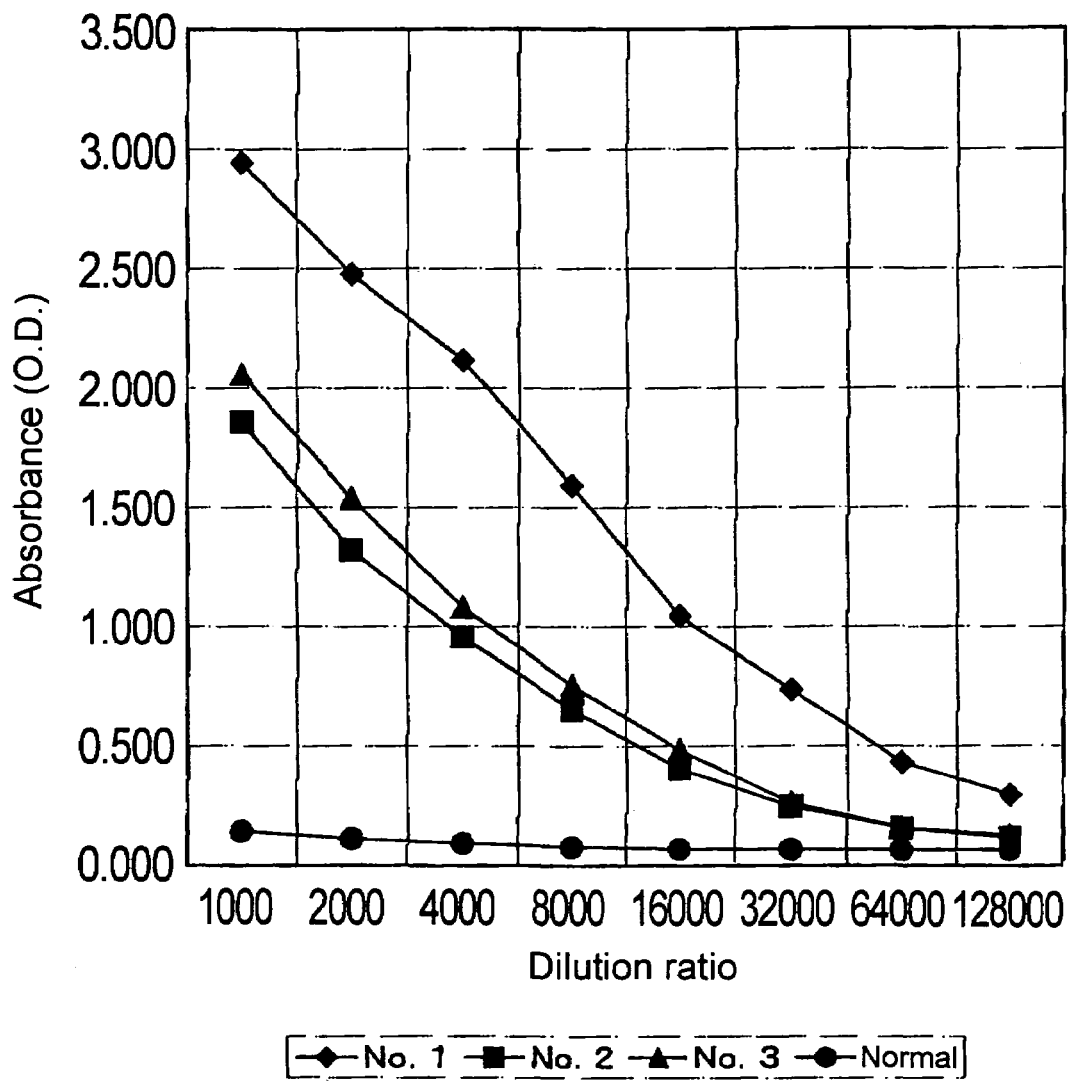
FIG. 41 indicates a diagram showing the results of ELISA of mouse serum immunized with Syno-P3. Serum obtained from three individuals (Nos. 1-3) was diluted in the indicated ratios and then ELISA was performed. Serum from a non-immunized mouse ("normal" in the diagram) was used as a control.
Figure 42:
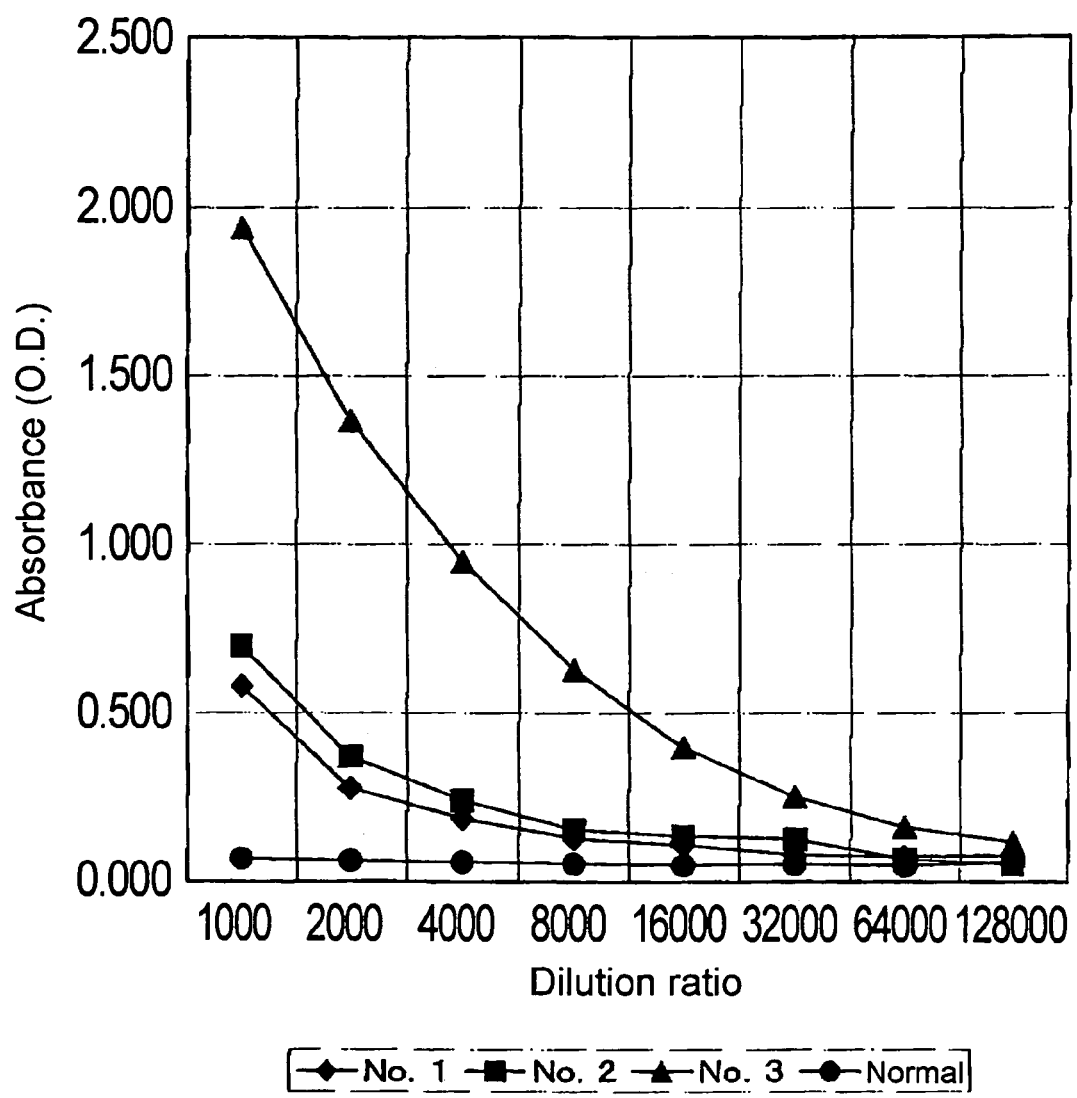
FIG. 42 indicates a diagram showing the results of ELISA of mouse serum immunized with Syno-P2. Serum obtained from three individuals (Nos. 1-3) was diluted in the indicated ratios and then ELISA was performed. Serum from a non-immunized mouse ("normal" in the diagram) was used as a control.
Figure 43:
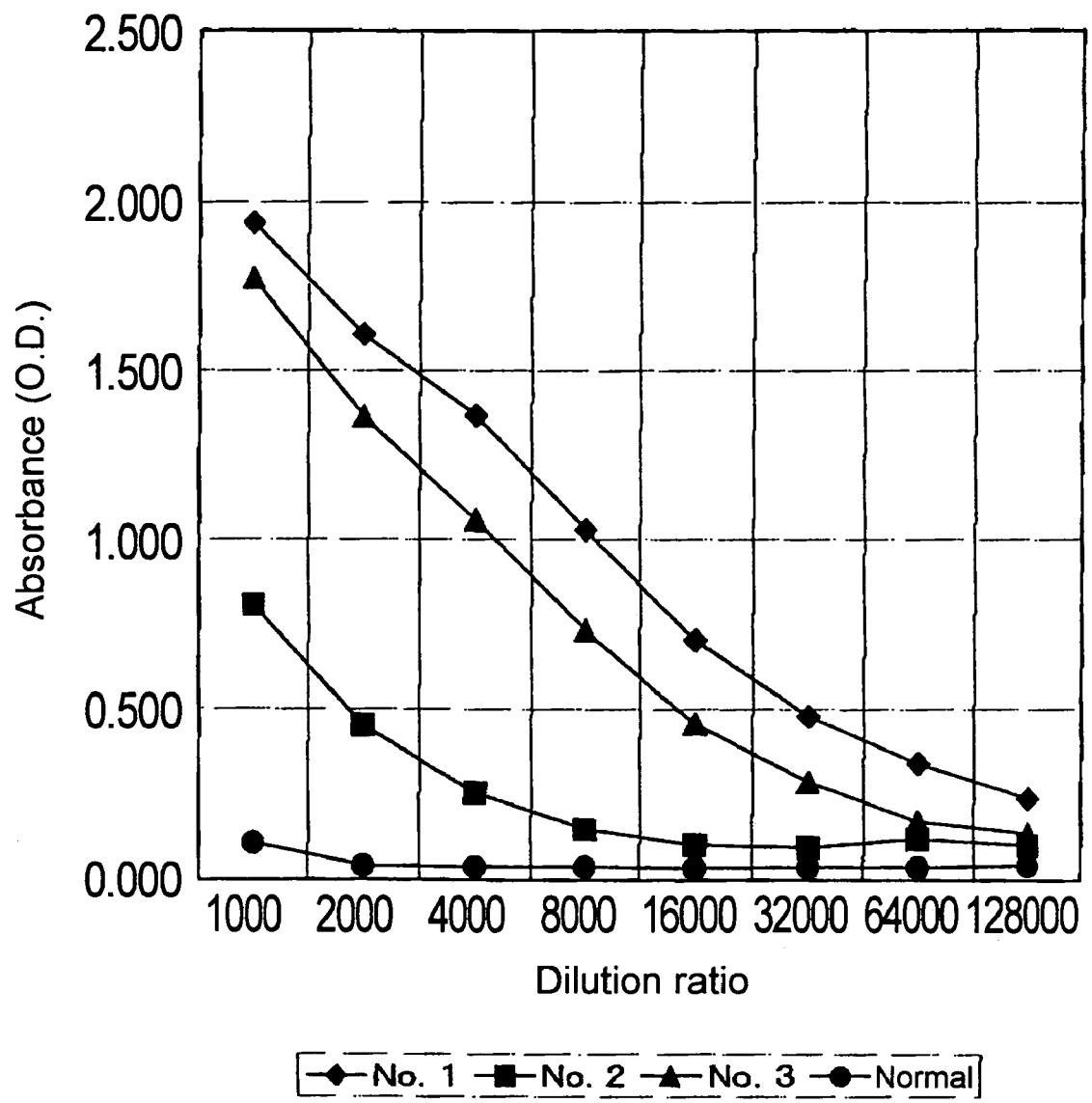
FIG. 43 indicates a diagram showing the results of ELISA of mouse serum immunized with Syno-P1. Serum obtained from three individuals (Nos. 1-3) was diluted in the indicated ratios and then ELISA was performed. Serum from a non-immunized mouse ("normal" in the diagram) was used as a control.

FIGS. 41-43 show the results of measuring the antibody titer by ELISA for the mouse serum of three individuals with respect to each of the immunogens. Each serum sample was assayed in triplicate, and the mean is shown on the graph. Individuals in which the antibody titer increased were confirmed when any of the immunogens was used. Thus, it was confirmed that each of these immunogens was useful as an immunogen of Synoviolin.

Myeloma cell line (P3U1) cells and mouse spleen cells were mixed in a 1:10 ratio and cell fusion was performed in the presence of 50% PEG (PEG1540 of Wako Pure Chemical Industries, Ltd.). After fusion, 96 well plates were seeded so that the spleen cell count became $5\times10^5$/ml. After the cells were cultured for 10-14 days in a HAT culture medium, cell growth was confirmed and the culture supernatant was tested. An ELISA plate on which the various synthesized peptides was fixed was used to test the culture supernatant. The testing procedures are as follows. After the culture supernatant was reacted with the ELISA plate, anti-mouse IgG goat-pox was used to select positive wells. The wells to be used for cloning were selected and the cells of other positive wells were frozen and stored.

Several days later, each strain was seeded over one 96-well plate at 100 cells/plate (20 cells/ml), and cultured for 10-14 days. The colonies were determined and testing of the culture supernatant was performed. Testing of the culture supernatant was performed by applying 50 µl of supernatant to the aforementioned antigen-fixed ELISA plates for screening. Anti-mouse IgG goat-pox was used as the second antibody. After cultured, the selected colonies were recloned and cultured for 10-14 days. Then, colony determination and testing of the culture supernatant were performed in the same manner as given above. Wells were selected according to mother strain, and selected clones were cultured in a 24-well plate. The supernatant was recovered, and clones were checked. Then, the antibody subclass and antibody production were tested.

As a result of the cloning, using Syno-P2 (SEQ ID NO: 4) as the immunogen, the two clones 10 Db and 7 Bc were selected as the hybridomas that produce monoclonal antibodies having the high affinity to Synoviolin.

EXAMPLE 24

Figure 44:
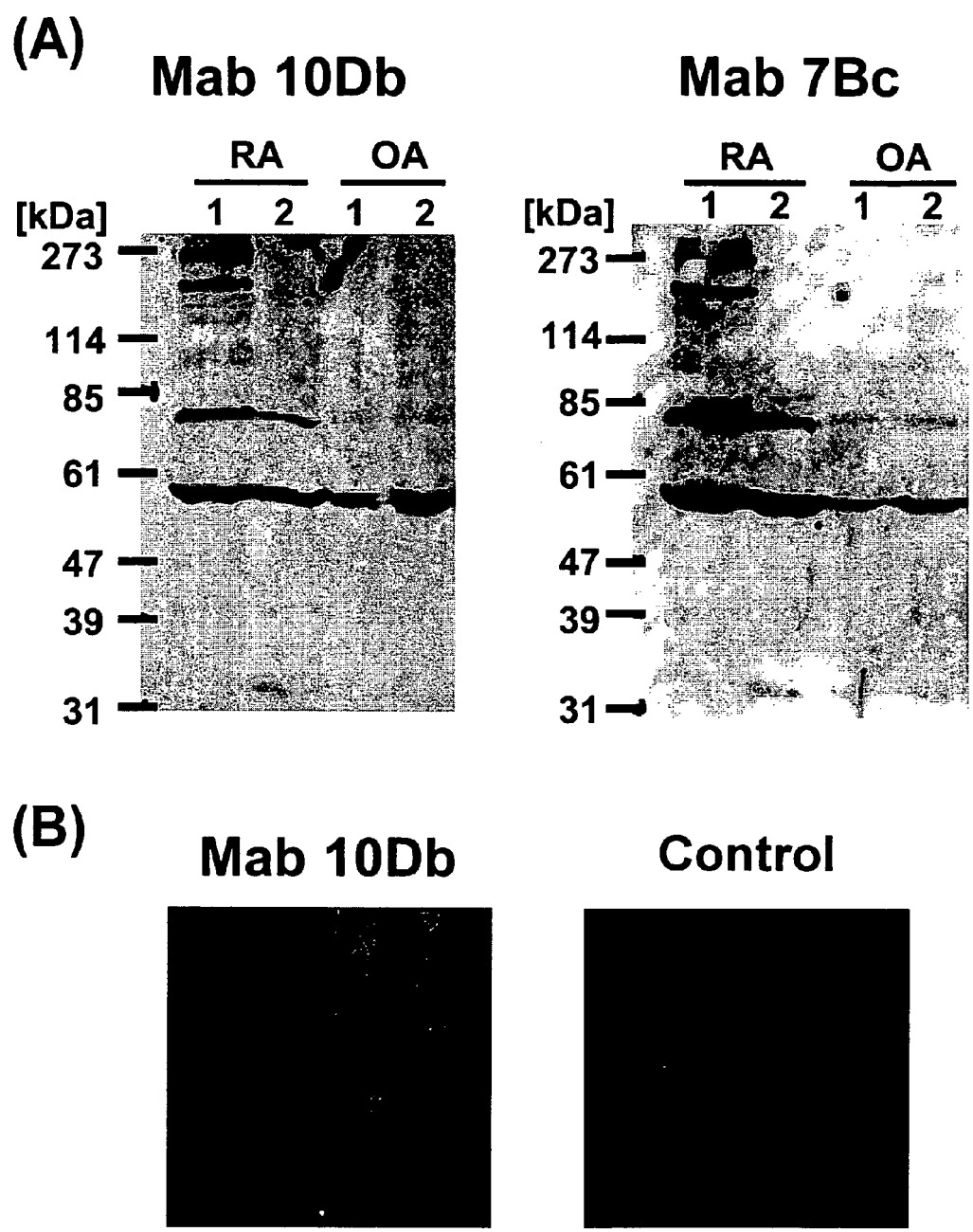
FIG. 44 indicates photographs showing the results of Western blotting (A) and fluorescent immunostaining (B) of synovial cells derived from RA and OA patients with anti-Synoviolin monoclonal antibodies.

Detection of Synoviolin in Patient Specimens Using Anti-Synoviolin Monoclonal Antibodies <1> Western Blotting of Patient-Derived Synovial Cells with Anti-Synoviolin Monoclonal Antibodies Using the two types of anti-Synoviolin monoclonal antibodies (10 Db and 7 Bc) that recognize Syno-P2 obtained in Example 23, proteins of rheumatoid arthritis (RA) patient-derived synovial cells were separated by SDS-PAGE and Western blotting was performed. The Western blotting procedure was as recited in Example 8 except that the monoclonal antibodies 10 Db and 7 Bc of Example 23 were used as the antibodies and anti-mouse IgG sheep-HRP was used as the labeled antibody. As a control, osteoarthritis (OA) patient-derived synovial cells were also analyzed. As a result, a signal specific to RA patient-derived synovial cells was detected (FIG. 44A). It was confirmed that the monoclonal antibodies obtained in Example 23 specifically recognized the synovial cells of RA patients. These monoclonal antibodies are useful in the detection of RA.

<2> Fluorescent Immunostaining of RA Patient-Derived Synovial Cells with Anti-Synoviolin Monoclonal Antibodies The monoclonal antibody 10 Db was used to perform fluorescent immune cytochemical analysis of RA patient-derived synovial cells. The immunostaining procedure was as recited in Example 9 except that the monoclonal antibodies 10 Db of Example 23 were used as the antibodies and anti-mouse IgG sheep-FITC was used as the labeled antibody. The Synoviolin protein signal was detected strongly in RA patient-derived synovial cells, but it was not detected in the control wherein only the secondary antibodies were reacted (FIG. 44B).

Figure 45:
FIG. 45 indicates photographs showing the results of immunostaining of synovial tissue derived from RA patients with anti-Synoviolin monoclonal antibodies. The hematoxylin eosin (HE) stain image is also shown.
Figure 45:
Figure 45:

<3> Immunostaining of RA Patient-Derived Synovial Tissues with Anti-Synoviolin Monoclonal Antibodies The monoclonal antibodies 10 Db and 7 Bc were used to perform immunostaining of synovial tissue sections taken from RA patients. The immunostaining procedure was as recited in Example 9 except that the monoclonal antibodies 10 Db and 7 Bc of Example 23 were used as the antibodies and anti-mouse IgG sheep-HRP was used as the labeled antibody. The Synoviolin protein signal was detected strongly in RA patient-derived synovial tissue (FIG. 45). A hyperplastic layer of synovial cells was observed by HE staining performed at the same time, and it was confirmed that the portion was stained by monoclonal antibodies. Based on these results, it was confirmed that the monoclonal antibodies of the present invention specifically recognized the synovial tissue of RA patients. As described above, RA testing and diagnosis can be performed by detecting Synoviolin in patient specimens using Synoviolin antibodies.

EXAMPLE 25

Detection of the Ubiquitin Ligase Activity of Synoviolin

Figure 46:
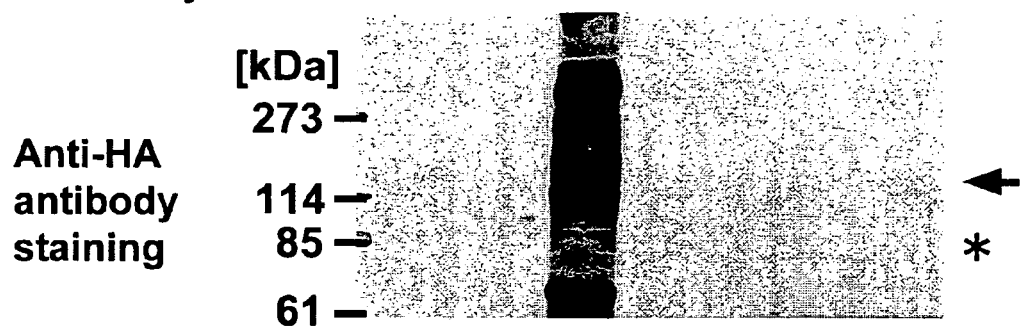
FIG. 46 indicates photographs showing the auto-ubiquitination activity of Synoviolin. FLAG-Synoviolin was reacted in the presence of GST-HA-ubiquitin, ATP, E1 and E2, and the ubiquitination of Synoviolin was detected with Anti-FLAG antibodies and Anti-HA antibodies. CE: cell extract. IP: immune precipitate.
Figure 46:
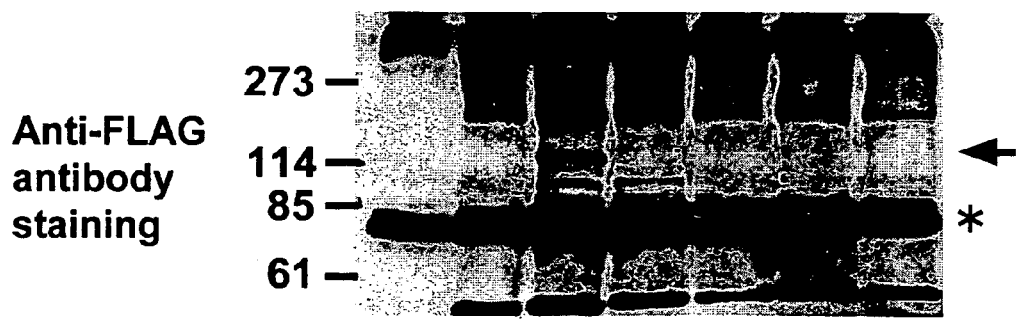

E3 ubiquitin-protein ligase is known to undergo auto-ubiquitination (Hashizume R. et al., J. Biol. Chem. 276, 14537-14540, 2001). Thus, the present inventors studied whether Synoviolin has auto-ubiquitination activity or not. Plasmids comprising a FLAG-synoviolin gene inserted into a pCAGGS vector were transfected into HEK-293 cells and the cells were recovered 36 hours later. A cell extract was obtained with Buffer A [15 mM Tris-HCl pH 7.5, 0.5 M NaCl, 0.35% NP-40, 1 mM PMSF, 2 µg/ml aprotinin, 2 µg/ml leupeptin]. The cell extract was centrifuged in a high-speed centrifuge. To 0.6 ml of the supernatant, 3 µg of anti-FLAG antibodies and 7.5 µl of Protein A beads were added, and immunoprecipitation was performed overnight. The beads were washed three times with Buffer A or Buffer A to which 0.1% SDS was added, and then washed two times with Buffer B [25 mM Tris-HCl pH 7.5, 50 mM NaCl, 0.01% Nonidet P-40, 10% glycerol, 1 mM EDTA]. Then, 30 µl of ubiquitin ligase reaction solution [50 mM Tris-HCl pH 7.4, 5 mM MgCl$_2$, 2 mM NaF, 10 nM okadaic acid, 2 mM ATP, 0.6 mM DTT, 1.5 µg GST-HA-ubiquitin, 40 ng yeast-derived E1, 0.3 µg UbcH5c(E2)] was added and it was allowed to react for 30 minutes at 37° C. 30 µl of 2× Laemmli SDS-loading buffer containing 0.1M DTT was added and boiled. Then, it was fractionated by SDS-PAGE and transferred to a nitrocellulose membrane. Anti-FLAG antibodies (SIGMA) and anti-HA antibodies (Roche Diagnostics) were used as the primary antibodies. The detection of HRP activity was performed in the same manner as in Example 7. As controls, the extract from cells transfected with the FLAG-synoviolin gene only (before immunoprecipitation) and the solution obtained by performing immunoprecipitation of the cell extract (i.e. FLAG-Synoviolin protein and its immunocomplex only) were used. Moreover, reactions were also performed without adding any one of GST-HA-ubiquitin, ATP, E1 and E2 (when GST-HA-ubiquitin was not added, the reaction was performed using GST). FIG. 46 shows the results of using Synoviolin immunopurified by washing with 0.1% SDS-containing Buffer A. In the blotting with anti-HA antibodies, a band whose size was about 35 kDa larger than the molecular weight of Synoviolin (* in FIG. 46) was detected (the arrow in FIG. 46). This band was also observed in the blotting with the anti-FLAG antibodies, and is thought to be that of a protein in which GST-HA-ubiquitin is fused to Synoviolin. Moreover, the reaction systems deficient in any one of ATP, E1 and E2 indicated that the auto-ubiquitination of Synoviolin did not occur. The same result was obtained when the beads were washed with Buffer A only. From these results, it is clear that 1) E1- and E2-dependent ubiquitin ligase activity is present in Synoviolin-containing immune complexes, and from the results of immunopurification, 2) Synoviolin has E3 ubiquitin-protein ligase activity.

INDUSTRIAL APPLICABILITY

The present invention provides the gene "synoviolin" which encodes a novel protein that contributes to the development of synovial membranes and to the development of bone, cartilage and limbs. The gene according to the present invention is involved in RA and antibodies to the products of this gene are produced in RA patients. The gene and protein according to the present invention become new markers useful in the diagnosis of RA. The "synoviolin" according to the present invention is overexpressed in the joint synovial cells of RA patients and contributes to the diagnosis of the disease RA and judgment of the effectiveness of treatment by in situ hybridization and in situ PCR. Moreover, antibodies to Synoviolin can be detected with a high frequency in the blood of RA patients. Specific diagnosis of RA is possible using this as a marker. The Synoviolin protein provided by the present invention, or partial peptides thereof, are useful in the detection of antibodies to Synoviolin in the serum of patients.

In addition, Synoviolin is also expressed in undifferentiated mesenchymal cells. If Synoviolin is used as a cell marker, then it is possible to recover undifferentiated mesenchymal cells from fetal cells or the like. Undifferentiated mesenchymal cells are cells that are differentiated into bone and cartilage and are expected to have applications in regenerative medicine. To wit, if undifferentiated mesenchymal cells recovered using Synoviolin as a cell marker are differentiated in vitro or in vivo and the formation of bone or cartilage or reconstruction of joints is performed, it becomes possible to reconstruct anew bones, cartilaginous tissue or joints that have suffered injuries.

The Synoviolin and its ligand according to the present invention have been shown to have a close relationship with the hyperplasia of joint synovial cells which is a major pathology of RA. Accordingly, the Synoviolin or its ligand provided by the present invention gives important knowledge in the development of RA treatment methods. More specifically, by performing the screening of compounds that are involved in the binding between Synoviolin and its ligand, it is possible to proceed with the development of RA treatment techniques by a completely different approach from that taken previously. Moreover, in the synoviolin transgenic mouse, hyperplasia of the joint synovial membranes and swelling of toe joints accompanying arthritis occur with a high frequency. The synoviolin transgenic animals provided by the present invention are extremely useful as a model of RA in the development of treatment techniques and pharmaceuticals.

The invention claimed is:

1. An isolated and purified protein comprising SEQ ID NO:2.
2. The protein of claim 1 that is encoded by the polynucleotide of SEQ ID NO:1.

* * * * *

UNITED STATES PATENT AND TRADEMARK OFFICE
CERTIFICATE OF CORRECTION

| | |
|---|---|
| PATENT NO. | : 7,632,507 B2 |
| APPLICATION NO. | : 10/275602 |
| DATED | : December 15, 2009 |
| INVENTOR(S) | : Nakajima et al. |

Page 1 of 1

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 547 days Delete the phrase "by 547 days" and insert -- by 945 days --

Signed and Sealed this

Twenty-fourth Day of August, 2010

David J. Kappos
*Director of the United States Patent and Trademark Office*

SEQUENCE LISTING

<160> NUMBER OF SEQ ID NOS: 7

<210> SEQ ID NO 1
<211> LENGTH: 3374
<212> TYPE: DNA
<213> ORGANISM: Homo sapiens

<400> SEQUENCE: 1

```
gccctttctt atgagcatgc ctgtgttggg ttgacagtga gggtaataat gacttgttgg      60
ttgattgtag atatagggct ctcccttgca aggtaattag gctccttaaa ttacctgtaa     120
gattttcttg ccacagcatc cattctggtt aggctggtga tcttctgagt agtgatagat     180
tggttggtgg tgaggtttac aggtgttccc ttctcttact cctggtgttg gctacaatca     240
ggtggcgtct agagcagcat gggacaggtg ggtaagggga gtcttctcat tatgcagaag     300
tgatcaactt aaatctctgt cagatctacc tttatgtagc ccggcagtcg cgcggattga     360
gcgggctcgc ggcgctgggt tcctggtctc cgggccaggg caatgttccg cacggcagtg     420
atgatggcgg ccagcctggc gctgaccggg gctgtggtgg ctcacgccta ctacctcaaa     480
caccagttct accccactgt ggtgtacctg accaagtcca gccccagcat ggcagtcctg     540
tacatccagg cctttgtcct tgtcttcctt ctgggcaagg tgatgggcaa ggtgttcttt     600
gggcaactga gggcagcaga gatggagcac cttctggaac gttcctggta cgccgtcaca     660
gagacttgtc tggccttcac cgttttccgg gatgacttca gcccccgctt tgttgcactc     720
ttcactcttc ttctcttcct caaatgtttc cactggctgg ctgaggaccg tgtggacttt     780
atggaacgca gccccaacat ctcctggctc tttcactgcc gcattgtctc tcttatgttc     840
ctcctgggca tcctggactt cctcttcgtc agccacgcct atcacagcat cctgacccgt     900
ggggcctctg tgcagctggt gtttggcttt gagtatgcca tcctgatgac gatggtgctc     960
accatcttca tcaagtatgt gctgcactcc gtggacctcc agagtgagaa cccctgggac    1020
aacaaggctg tgtacatgct ctacacagag ctgtttacag gcttcatcaa ggttctgctg    1080
tacatggcct tcatgaccat catgatcaag gtgcacacct tcccactctt tgccatccgg    1140
cccatgtacc tggccatgag acagttcaag aaagctgtga cagatgccat catgtctcgc    1200
cgagccatcc gcaacatgaa caccctgtat ccagatgcca cccagagga gctccaggca    1260 atggacaatg tctgcatcat ctgccgagaa gagatggtga ctggtgccaa gagactgccc    1320
tgcaaccaca ttttccatac cagctgcctg cgctcctggt tccagcggca gcagacctgc    1380
cccacctgcc gtatggatgt ccttcgtgca tcgctgccag cgcagtcacc accacccccg    1440
gagcctgcgg atcaggggcc acccctgcc cccaccccc caccactctt gcctcagccc    1500
cccaacttcc cccagggcct cctgcctcct tttcctccag gcatgttccc actgtggccc    1560
cccatgggcc cctttccacc tgtcccgcct cccccagct caggagaggc tgtggctcct    1620
```

-continued

| | | | | |
|---|---|---|---|---|
| ccatccacca | gtgcagcagc | cctttctcgg | cccagtggag | cagctacaac cacagctgct | 1680 |
| ggcaccagtg | ctactgctgc | ttctgccaca | gcatctggcc | caggctctgg ctctgcccca | 1740 |
| gaggctggcc | ctgcccctgg | tttccccttc | cctcctccct | ggatgggtat gcccctgcct | 1800 |
| ccacccttg | ccttcccccc | aatgcctgtg | cccctgcgg | ctttgctgg gctgacccca | 1860 |
| gaggagctac | gagctctgga | gggccatgag | cggcagcacc | tggaggcccg gctgcagagc | 1920 |
| ctgcgtaaca | tccacacact | gctggacgcc | gccatgctgc | agatcaacca gtacctcacc | 1980 |
| gtgctggcct | ccttggggcc | ccccggcct | gccacttcag | tcaactccac tgaggggact | 2040 |
| gccactacag | ttgttgctgc | tgcctcctcc | accagcatcc | ctagctcaga ggccacgacc | 2100 |
| caaccccag | gagcctcccc | accagcccct | gaaatggaaa | ggcctccagc tcctgagtca | 2160 |
| gtgggcacag | aggagatgcc | tgaggatgga | gagcccgatg | cagcagagct ccgccggcgc | 2220 |
| cgcctgcaga | agctggagtc | tcctgttgcc | cactgacact | gccccagccc agccccagcc | 2280 |
| tctgctcttt | tgagcagccc | tcgctggaac | atgtcctgcc | accaagtgcc agctccctct | 2340 |
| ctgtctgcac | cagggagtag | taccccccagc | tctgagaaag | aggcggcatc ccctaggcca | 2400 |
| agtggaaaga | ggctggggtt | cccatttgac | tccagtccca | ggcagccatg gggatctcgg | 2460 |
| gtcagttcca | gccttcctct | ccaactcttc | agccctgtgt | tctgctgggg ccatgaaggc | 2520 |
| agaaggttta | gcctctgaga | agccctcttc | ttccccacc | cctttccagg agaaggggct | 2580 |
| gccctccaa | gccctacttg | tatgtgcgga | gtcacactgc | agtgccgaac agtattagct | 2640 |
| cccgttccca | agtgtggact | ccagagggc | tggaggcaag | ctatgaactt gctcgctggc | 2700 |
| ccacccctaa | gactggtacc | catttccttt | tcttaccctg | atctccccag aagcctcttg | 2760 |
| tggtggtggc | tgtgccccct | atgccctgtg | gcatttctgc | gtcttactgg caaccacaca | 2820 |
| actcagggaa | aggaatgcct | gggagtgggg | gtgcaggcgg | gcagcactga gggaccctgc | 2880 |
| cccgcccctc | cccccaggcc | cctttcccct | gcagcttctc | aagtgagact gacctgtctc | 2940 |
| acccagcagc | cactgcccag | ccgcactcca | ggcaagggcc | agtgcgcctg ctcctgacca | 3000 |
| ctgcaatccc | agcgcccaag | gaaggccact | tctcaactgg | cagaacttct gaagtttaga | 3060 |
| attggaatta | cttccttact | agtgtctttt | ggcttaaatt | ttgtcttttg aagttgaatg | 3120 |
| cttaatcccg | ggaaagagga | acaggagtgc | cagactcctg | gtctttccag tttagaaaag | 3180 |
| gctctgtgcc | aaggagggac | cacaggagct | gggacctgcc | tgcccctgtc ctttcccctt | 3240 |
| ggttttgtgt | tacaagagtt | gttggagaca | gtttcagatg | attatttaat ttgtaaatat | 3300 |
| tgtacaaatt | ttaatagctt | aaattgtata | tacagccaaa | taaaaacttg cattaacaaa | 3360 |
| aaaaaaaaaa | aaaa | | | | 3374 |

<210> SEQ ID NO 2
<211> LENGTH: 617
<212> TYPE: PRT
<213> ORGANISM: Homo sapiens

<400> SEQUENCE: 2

```
Met Phe Arg Thr Ala Val Met Met Ala Ala Ser Leu Ala Leu Thr Gly
  1               5                  10                  15

Ala Val Val Ala His Ala Tyr Tyr Leu Lys His Gln Phe Tyr Pro Thr
             20                  25                  30

Val Val Tyr Leu Thr Lys Ser Ser Pro Ser Met Ala Val Leu Tyr Ile
         35                  40                  45

Gln Ala Phe Val Leu Val Phe Leu Leu Gly Lys Val Met Gly Lys Val
```

```
           50                  55                  60
Phe Phe Gly Gln Leu Arg Ala Ala Glu Met Glu His Leu Leu Glu Arg
 65                  70                  75                  80

Ser Trp Tyr Ala Val Thr Glu Thr Cys Leu Ala Phe Thr Val Phe Arg
                 85                  90                  95

Asp Asp Phe Ser Pro Arg Phe Val Ala Leu Phe Thr Leu Leu Leu Phe
            100                 105                 110

Leu Lys Cys Phe His Trp Leu Ala Glu Asp Arg Val Asp Phe Met Glu
        115                 120                 125

Arg Ser Pro Asn Ile Ser Trp Leu Phe His Cys Arg Ile Val Ser Leu
    130                 135                 140

Met Phe Leu Leu Gly Ile Leu Asp Phe Leu Phe Val Ser His Ala Tyr
145                 150                 155                 160

His Ser Ile Leu Thr Arg Gly Ala Ser Val Gln Leu Val Phe Gly Phe
                165                 170                 175

Glu Tyr Ala Ile Leu Met Thr Met Val Leu Thr Ile Phe Ile Lys Tyr
            180                 185                 190

Val Leu His Ser Val Asp Leu Gln Ser Glu Asn Pro Trp Asp Asn Lys
        195                 200                 205

Ala Val Tyr Met Leu Tyr Thr Glu Leu Phe Thr Gly Phe Ile Lys Val
    210                 215                 220

Leu Leu Tyr Met Ala Phe Met Thr Ile Met Ile Lys Val His Thr Phe
225                 230                 235                 240

Pro Leu Phe Ala Ile Arg Pro Met Tyr Leu Ala Met Arg Gln Phe Lys
                245                 250                 255

Lys Ala Val Thr Asp Ala Ile Met Ser Arg Arg Ala Ile Arg Asn Met
            260                 265                 270

Asn Thr Leu Tyr Pro Asp Ala Thr Pro Glu Glu Leu Gln Ala Met Asp
        275                 280                 285

Asn Val Cys Ile Ile Cys Arg Glu Glu Met Val Thr Gly Ala Lys Arg
    290                 295                 300

Leu Pro Cys Asn His Ile Phe His Thr Ser Cys Leu Arg Ser Trp Phe
305                 310                 315                 320

Gln Arg Gln Gln Thr Cys Pro Thr Cys Arg Met Asp Val Leu Arg Ala
                325                 330                 335

Ser Leu Pro Ala Gln Ser Pro Pro Pro Glu Pro Ala Asp Gln Gly
            340                 345                 350

Pro Pro Pro Ala Pro His Pro Pro Leu Leu Pro Gln Pro Pro Asn
        355                 360                 365

Phe Pro Gln Gly Leu Leu Pro Pro Phe Pro Gly Met Phe Pro Leu
    370                 375                 380

Trp Pro Pro Met Gly Pro Phe Pro Pro Val Pro Pro Pro Ser Ser
385                 390                 395                 400

Gly Glu Ala Val Ala Pro Pro Ser Thr Ser Ala Ala Leu Ser Arg
                405                 410                 415

Pro Ser Gly Ala Ala Thr Thr Thr Ala Ala Gly Thr Ser Ala Thr Ala
            420                 425                 430

Ala Ser Ala Thr Ala Ser Gly Pro Gly Ser Gly Ser Ala Pro Glu Ala
        435                 440                 445

Gly Pro Ala Pro Gly Phe Pro Phe Pro Pro Trp Met Gly Met Pro
    450                 455                 460

Leu Pro Pro Pro Phe Ala Phe Pro Pro Met Pro Val Pro Pro Ala Gly
465                 470                 475                 480
```

-continued

```
Phe Ala Gly Leu Thr Pro Glu Glu Leu Arg Ala Leu Glu Gly His Glu
                485                 490                 495

Arg Gln His Leu Glu Ala Arg Leu Gln Ser Leu Arg Asn Ile His Thr
            500                 505                 510

Leu Leu Asp Ala Ala Met Leu Gln Ile Asn Gln Tyr Leu Thr Val Leu
        515                 520                 525

Ala Ser Leu Gly Pro Pro Arg Pro Ala Thr Ser Val Asn Ser Thr Glu
    530                 535                 540

Gly Thr Ala Thr Thr Val Val Ala Ala Ser Ser Thr Ser Ile Pro
545                 550                 555                 560

Ser Ser Glu Ala Thr Thr Pro Thr Pro Gly Ala Ser Pro Pro Ala Pro
                565                 570                 575

Glu Met Glu Arg Pro Pro Ala Pro Glu Ser Val Gly Thr Glu Glu Met
            580                 585                 590

Pro Glu Asp Gly Glu Pro Asp Ala Ala Glu Leu Arg Arg Arg Arg Leu
        595                 600                 605

Gln Lys Leu Glu Ser Pro Val Ala His
    610                 615

<210> SEQ ID NO 3
<211> LENGTH: 15
<212> TYPE: PRT
<213> ORGANISM: Artificial Sequence
<220> FEATURE:
<223> OTHER INFORMATION: Synoviolin fragment

<400> SEQUENCE: 3

Ser Leu Ala Leu Thr Gly Ala Val Val Ala His Ala Tyr Tyr Cys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synoviolin fragment

<400> SEQUENCE: 4

Thr Cys Arg Met Asp Val Leu Arg Ala Ser Leu Pro Ala Gln Ser
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synoviolin fragment

<400> SEQUENCE: 5

Gly Ala Ala Thr Thr Thr Ala Ala Gly Thr Ser Ala Thr Ala Cys
1               5                   10                  15

<210> SEQ ID NO 6
<211> LENGTH: 3028
<212> TYPE: DNA
<213> ORGANISM: Homo sapiens

<400> SEQUENCE: 6
gcagtcgcgc ggattgagcg ggctcgcggc gctgggttcc tggtctccgg gccagggcaa     60
tgttccgcac ggcagtgatg atggcggcca gcctggcgct gaccgggget gtggtggctc    120
```

```
acgcctacta cctcaaacac cagttctacc ccactgtggt gtacctgacc aagtccagcc      180
ccagcatggc agtcctgtac atccaggcct ttgtccttgt cttccttctg ggcaaggtga      240
tgggcaaggt gttctttggg caactgaggg cagcagagat ggagcacctt ctggaacgtt      300
cctggtacgc cgtcacagag acttgtctgg ccttcaccgt ttttcgggat gacttcagcc      360
cccgctttgt tgcactcttc actcttcttc tcttcctcaa atgtttccac tggctggctg      420
aggaccgtgt ggactttatg gaacgcagcc ccaacatctc ctggctcttt cactgccgca      480
ttgtctctct tatgttcctc ctgggcatcc tggacttcct cttcgtcagc cacgcctatc      540
acagcatcct gacccgtggg gcctctgtgc agctggtgtt tggctttgag tatgccatcc      600
tgatgacgat ggtgctcacc atcttcatca agtatgtgct gcactccgtg gacctccaga      660
gtgagaaccc ctgggacaac aaggctgtgt acatgctcta cacagagctg tttacaggct      720
tcatcaaggt tctgctgtac atggccttca tgaccatcat gatcaaggtg cacaccttcc      780
cactctttgc catccggccc atgtacctgg ccatgagaca gttcaagaaa gctgtgacag      840
atgccatcat gtctcgccga gccatccgca acatgaacac cctgtatcca gatgccaccc      900
cagaggagct ccaggcaatg gacaatgtct gcatcatctg ccgagaagag atggtgactg      960
gtgccaagag actgccctgc aaccacattt tccataccag ctgcctgcgc tcctggttcc     1020
agcggcagca gacctgcccc acctgccgta tggatgtcct tcgtgcatcg ctgccagcgc     1080
agtcaccacc acccccggag cctgcggatc aggggccacc ccctgccccc accccccac      1140 cactcttgcc tcagcccccc aacttccccc agggcctcct gctcctttt cctccaggca      1200 tgttcccact gtggcccccc atgggcccct ttccacctgt cccgcctccc cccagctcag     1260
gagaggctgt ggctcctcca tccaccagtg cagccctttc tcggcccagt ggagcagcta     1320
caaccacagc tgctggcacc agtgctactg ctgcttctgc cacagcatct ggcccaggct     1380
ctggctctgc cccagaggct ggccctgccc ctggtttccc cttccctcct ccctggatgg     1440
gtatgcccct gcctccaccc tttgccttcc ccccaatgcc tgtgcccct gcgggctttg      1500 ctgggctgac cccagaggag ctacgagctc tggagggcca tgagcggcag cacctggagg     1560
cccggctgca gagcctgcgt aacatccaca cactgctgga cgccgccatg ctgcagatca     1620
accagtacct caccgtgctg gcctccttgg ggccccccg gcctgccact tcagtcaact      1680
ccactgaggg gactgccact acagttgttg ctgctgcctc ctccaccagc atccctagct     1740
cagaggccac gaccccaacc ccaggagcct ccccaccagc ccctgaaatg gaaaggcctc     1800
cagctcctga gtcagtgggc acagaggaga tgcctgagga tggagagccc gatgcagcag     1860
agctccgccg gcgccgcctg cagaagctgg agtctcctgt tgcccactga cactgcccca     1920
gcccagcccc agctctgct cttttgagca gccctcgctg aacatgtcc tgccaccaag       1980 tgccagctcc ctctctgtct gcaccaggga gtagtacccc cagctctgag aaagaggcgg     2040 catccctag gccaagtgga aagaggctgg ggttcccatt tgactccagt cccaggcagc      2100
catggggatc tcgggtcagt tccagccttc ctctccaact cttcagccct gtgttctgct     2160
ggggccatga aggcagaagg tttagcctct gagaagccct tcttccccc accccttttc     2220 caggagaagg ggctgcccct ccaagcccta cttgtatgtg cggagtcaca ctgcagtgcc     2280
gaacagtatt agctcccgtt cccagtgtg actccagag gggctggagg caagctatga      2340
acttgctcgc tggcccaccc ctaagactgg tacccattc cttttcttac cctgatctcc      2400
ccagaagcct cttgtggtgg tggctgtgcc cctatgccc tgtggcattt ctgcgtctta      2460
ctggcaacca cacaactcag ggaaaggaat gcctgggagt gggggtgcag gcgggcagca    2520
```

-continued

```
ctgagggacc ctgccccgcc cctcccccca ggccccttc ccctgcagct tctcaagtga    2580
gactgacctg tctcacccag cagccactgc ccagccgcac tccaggcaag ggccagtgcg    2640
cctgctcctg accactgcaa tcccagcgcc caaggaaggc cacttctcaa ctggcagaac    2700
ttctgaagtt tagaattgga attacttcct tactagtgtc ttttggctta aattttgtct    2760
tttgaagttg aatgcttaat cccgggaaag aggaacagga gtgccagact cctggtcttt    2820
ccagtttaga aaggctctg tgccaaggag ggaccacagg agctgggacc tgcctgcccc     2880 tgtccttcc ccttggtttt gtgttacaag agttgttgga gacagtttca gatgattatt     2940
taatttgtaa atattgtaca aattttaata gcttaaattg tatatacagc caaataaaaa    3000
cttgcattaa caaaaaaaaa aaaaaaaa                                        3028
```

<210> SEQ ID NO 7
<211> LENGTH: 616
<212> TYPE: PRT
<213> ORGANISM: Homo sapiens

<400> SEQUENCE: 7

```
Met Phe Arg Thr Ala Val Met Met Ala Ala Ser Leu Ala Leu Thr Gly
  1               5                  10                  15

Ala Val Val Ala His Ala Tyr Tyr Leu Lys His Gln Phe Tyr Pro Thr
             20                  25                  30

Val Val Tyr Leu Thr Lys Ser Ser Pro Ser Met Ala Val Leu Tyr Ile
         35                  40                  45

Gln Ala Phe Val Leu Val Phe Leu Leu Gly Lys Val Met Gly Lys Val
     50                  55                  60

Phe Phe Gly Gln Leu Arg Ala Ala Glu Met Glu His Leu Leu Glu Arg
 65                  70                  75                  80

Ser Trp Tyr Ala Val Thr Glu Thr Cys Leu Ala Phe Thr Val Phe Arg
                 85                  90                  95

Asp Asp Phe Ser Pro Arg Phe Val Ala Leu Phe Thr Leu Leu Leu Phe
            100                 105                 110

Leu Lys Cys Phe His Trp Leu Ala Glu Asp Arg Val Asp Phe Met Glu
        115                 120                 125

Arg Ser Pro Asn Ile Ser Trp Leu Phe His Cys Arg Ile Val Ser Leu
    130                 135                 140

Met Phe Leu Leu Gly Ile Leu Asp Phe Leu Phe Val Ser His Ala Tyr
145                 150                 155                 160

His Ser Ile Leu Thr Arg Gly Ala Ser Val Gln Leu Val Phe Gly Phe
                165                 170                 175

Glu Tyr Ala Ile Leu Met Thr Met Val Leu Thr Ile Phe Ile Lys Tyr
            180                 185                 190

Val Leu His Ser Val Asp Leu Gln Ser Glu Asn Pro Trp Asp Asn Lys
        195                 200                 205

Ala Val Tyr Met Leu Tyr Thr Glu Leu Phe Thr Gly Phe Ile Lys Val
    210                 215                 220

Leu Leu Tyr Met Ala Phe Met Thr Ile Met Ile Lys Val His Thr Phe
225                 230                 235                 240

Pro Leu Phe Ala Ile Arg Pro Met Tyr Leu Ala Met Arg Gln Phe Lys
                245                 250                 255

Lys Ala Val Thr Asp Ala Ile Met Ser Arg Arg Ala Ile Arg Asn Met
            260                 265                 270

Asn Thr Leu Tyr Pro Asp Ala Thr Pro Glu Glu Leu Gln Ala Met Asp
```

-continued

```
                275                 280                 285
Asn Val Cys Ile Ile Cys Arg Glu Glu Met Val Thr Gly Ala Lys Arg
    290                 295                 300
Leu Pro Cys Asn His Ile Phe His Thr Ser Cys Leu Arg Ser Trp Phe
305                 310                 315                 320
Gln Arg Gln Gln Thr Cys Pro Thr Cys Arg Met Asp Val Leu Arg Ala
            325                 330                 335
Ser Leu Pro Ala Gln Ser Pro Pro Pro Glu Pro Ala Asp Gln Gly
            340                 345                 350
Pro Pro Pro Ala Pro His Pro Pro Leu Leu Pro Gln Pro Pro Asn
        355                 360                 365
Phe Pro Gln Gly Leu Leu Pro Pro Phe Pro Pro Gly Met Phe Pro Leu
    370                 375                 380
Trp Pro Pro Met Gly Pro Phe Pro Pro Val Pro Pro Pro Ser Ser
385                 390                 395                 400
Gly Glu Ala Val Ala Pro Pro Ser Thr Ser Ala Ala Leu Ser Arg Pro
                405                 410                 415
Ser Gly Ala Ala Thr Thr Thr Ala Ala Gly Thr Ser Ala Thr Ala Ala
            420                 425                 430
Ser Ala Thr Ala Ser Gly Pro Gly Ser Gly Ser Ala Pro Glu Ala Gly
            435                 440                 445
Pro Ala Pro Gly Phe Pro Phe Pro Pro Pro Trp Met Gly Met Pro Leu
    450                 455                 460
Pro Pro Pro Phe Ala Phe Pro Pro Met Pro Val Pro Pro Ala Gly Phe
465                 470                 475                 480
Ala Gly Leu Thr Pro Glu Glu Leu Arg Ala Leu Glu Gly His Glu Arg
            485                 490                 495
Gln His Leu Glu Ala Arg Leu Gln Ser Leu Arg Asn Ile His Thr Leu
                500                 505                 510
Leu Asp Ala Ala Met Leu Gln Ile Asn Gln Tyr Leu Thr Val Leu Ala
            515                 520                 525
Ser Leu Gly Pro Pro Arg Pro Ala Thr Ser Val Asn Ser Thr Glu Gly
        530                 535                 540
Thr Ala Thr Thr Val Val Ala Ala Ser Ser Thr Ser Ile Pro Ser
545                 550                 555                 560
Ser Glu Ala Thr Thr Pro Thr Pro Gly Ala Ser Pro Ala Pro Glu
            565                 570                 575
Met Glu Arg Pro Pro Ala Pro Glu Ser Val Gly Thr Glu Glu Met Pro
            580                 585                 590
Glu Asp Gly Glu Pro Asp Ala Ala Glu Leu Arg Arg Arg Arg Leu Gln
        595                 600                 605
Lys Leu Glu Ser Pro Val Ala His
    610                 615
```